(12) United States Patent
Canter et al.

(10) Patent No.: US 6,265,151 B1
(45) Date of Patent: Jul. 24, 2001

(54) APPARATUS AND METHOD FOR INFECTIOUS DISEASE DETECTION

(75) Inventors: Joseph M. Canter, Lexington; Yongwu Yang, Belmont; Wanglong Zhou, Reading, all of MA (US)

(73) Assignee: SerOptix, Inc., Woburn, MA (US)

( * ) Notice: Subject to any disclaimer, the term of this patent is extended or adjusted under 35 U.S.C. 154(b) by 0 days.

(21) Appl. No.: 09/224,141

(22) Filed: Dec. 31, 1998

Related U.S. Application Data

(60) Provisional application No. 60/079,556, filed on Mar. 27, 1998.

(51) Int. Cl.$^7$ .............................. C12Q 1/00; C12Q 1/70; G01N 33/53; G01N 33/567; G01N 33/569

(52) U.S. Cl. .................................. 435/5; 435/4; 435/7.1; 435/7.2; 435/7.21; 435/7.22; 435/7.32; 435/7.92; 436/171; 436/172

(58) Field of Search ............................ 435/5, 4, 7.1, 7.2, 435/7.21, 7.22, 7.32, 7.92; 436/171, 172

(56) References Cited

U.S. PATENT DOCUMENTS

| 4,731,324 | 3/1988 | Huang et al. ............................. 435/5 |
| 5,262,526 | * 11/1993 | Sasamoto et al. .................... 435/551 |
| 5,459,317 | 10/1995 | Small et al. ........................... 250/341 |
| 5,708,957 | 1/1998 | Chuang et al. .......................... 422/82 |
| 6,081,612 | 6/2000 | Gutkowicz-Krusin et al. ..... 382/128 |

OTHER PUBLICATIONS van den Biesen, et al., "Yield of Fluorescence from Indocyanine Green in Plasma and Flowing Blood", Annals of Biomedical Eng. vol. 23, pp. 475–481 (1995).
Reyderman, et al., "Quantitative Determination of Short Single–Stranded Oligonucleotides from Blood Plasma Using Capillary Elecrtophoresis with Laser–Induced Fluorescence Detection," Anal. Chem. 69, pp. 3218–3232 (1997).
Kiang, et al., "Determination of Femtomole/Milliliter Concentrations of Enprostil Acid in Human Plasma Using High- -Performance Liquid Chromatography–Laser–Induced Fluorescence Detection," J. of Chromotography, 567:pp. 195–212 (1991).
M. Goldberg, et al., "Studies and comparison of pterin patterns in the plasma of dogs and cats and their alterations in various neoplasias and virus infections.,"Zentralbl Veterinarmed A, Jun. 1996; 43(4):201–209 (Abstract only).
A. Bakir, et al., "A study of xanthopterin in chronic renal failure," Am J Nephrol, 1992; 12(4):224–8 (Abstract only).
H.J.Zeitler, et al., "Evaluation of pteridines in patients with different tumors," Cancer Detect Prev, 1987; 10(1–2):71–9 Abstract only).

Andondonskaja–Renz B., et al., "Separation of pteridines from blood cells and plasma by reverse–phase high–performance liquid chromatograph," Anal Biochem, Aug. 1983; 133(1):68–78 (Abstract only).
B. Stea, et al., "Separation of unconjugated pteridines by high–pressure cation–exchange liquid chromatgraphy," J Chromatogr, Jan. 21, 1979, 168(2):385–93 (Abstract only).
M. Irikura et al., "7–Alkylaminocoumarin–4–acetic acids as fluorescent probe for studies of drug–binding sites on human serum albumin," Chem Pharm Bull (Tokyo), Mar. 1991, 39(3):724–8 (Abstract only).
F. Moreno, et al., "Binding of the Promen Fluorescent probe to human serum albumin: a fluorescence spectroscopic study," Chem Biol Interact, Aug. 1, 1999, 121(3):237–52 (Abstract only).
L. Costantino, et al., "Heteroarylalkanoic acids with possible antiinflammatory activities, Note IX. The binding to human serum albumin," Boll Chim Farm, Oct. 1989, 128(10):315–8 (Abstract only).
M. Otagiri, et al., "Binding of pirprofen to human serum albumin studied by dialysis and spectroscopy techniques," Biochem. Pharmacol, Jan. 1, 1989, 38(1):1–7 (Abstract only).
E. Ochoa De Aspuru, et al., "Usefulness of difference spectroscopy in the study of the binding of uracil derivatives to human serum albumin," J Biochem Biophys Methods, Sep. 27, 1993, (2):87–94 (Abstract only).
Fields et al.; Fields Virology 3rd Ed; vol. 1; pp. 755–758, 1996.*
Longworth; A new component in protein fluorescence; Annals of New York Academy of Sciences; vol. 366; abstract, 1981.*

* cited by examiner

Primary Examiner—Brett L. Nelson
(74) Attorney, Agent, or Firm—Pennie & Edmonds LLP

(57) ABSTRACT

A process for detecting HIV infection, Hepatitis A, B and C, and other similar infections in a plasma sample, wherein the process involves the use of an excitation laser source to irradiate upon the plasma sample an excitation laser beam to obtain a fluorescence emission spectrum of the plasma sample. The invention uses an excitation laser wavelength of about 355 nanometers. Detection of the fluorescence is made in the wavelength range from about 380 to 600 nanometers. The resulting spectrum of the sample is compared with the spectrum of a control which is free from infection. Analysis of the parameters of the emission spectra including, but not limited to, peak intensity wavelength, amplitude at the peak intensity, area ratio of left and right portions of the emission spectra, and shifts of the peak intensity wavelength, allows determination of HIV infection, Hepatitis A, B and C, and other similar infection in the plasma. Selective absorbents, such as C-M Affi Gel Blue and activated charcoal, may be used to treat the samples before fluorescence measurements, which is found to improve discrimination of infected and uninfected samples. The present invention is capable of detecting HIV infection at the stage when it is still undetectable by conventional diagnosis methods.

21 Claims, 46 Drawing Sheets

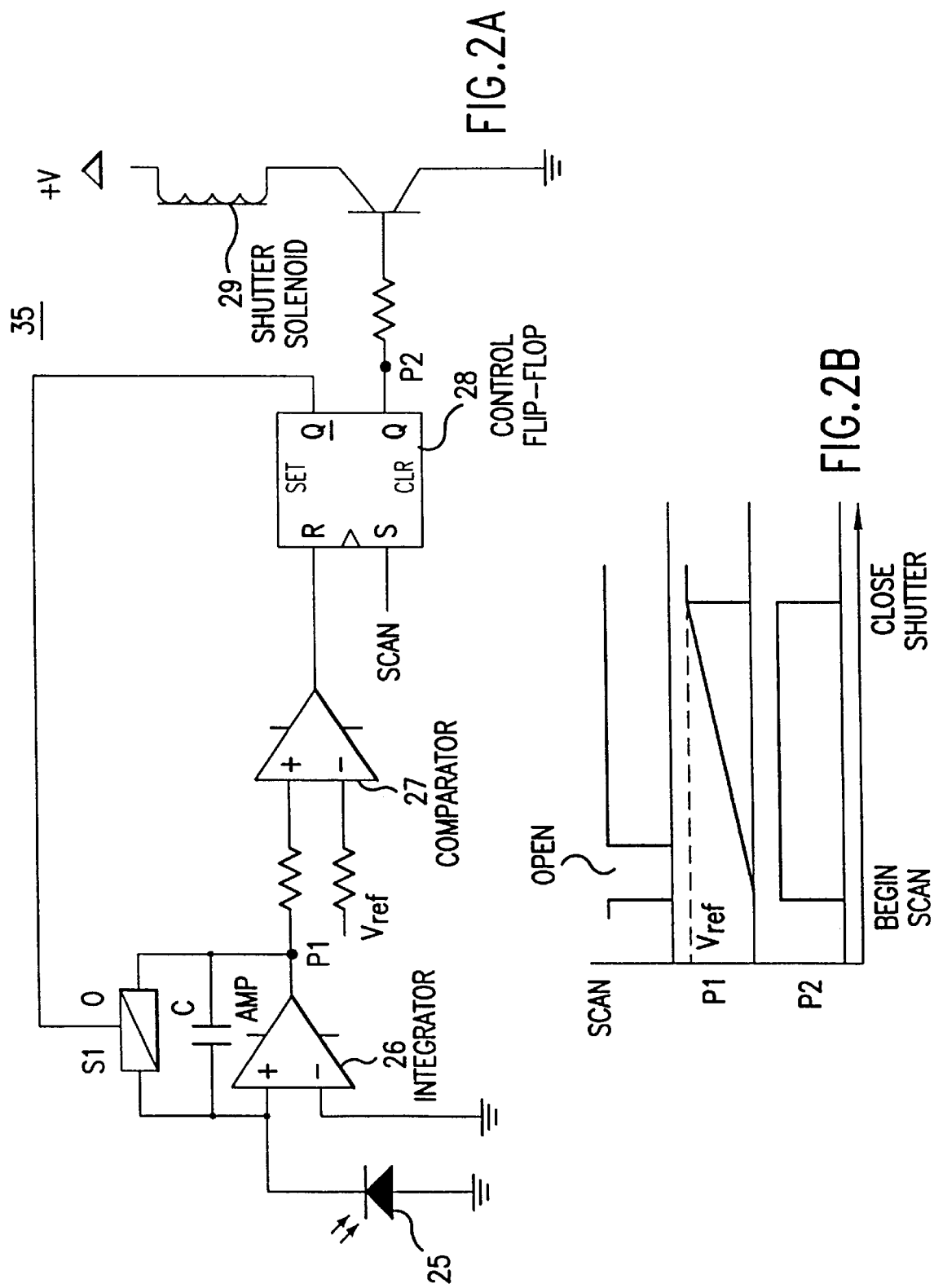

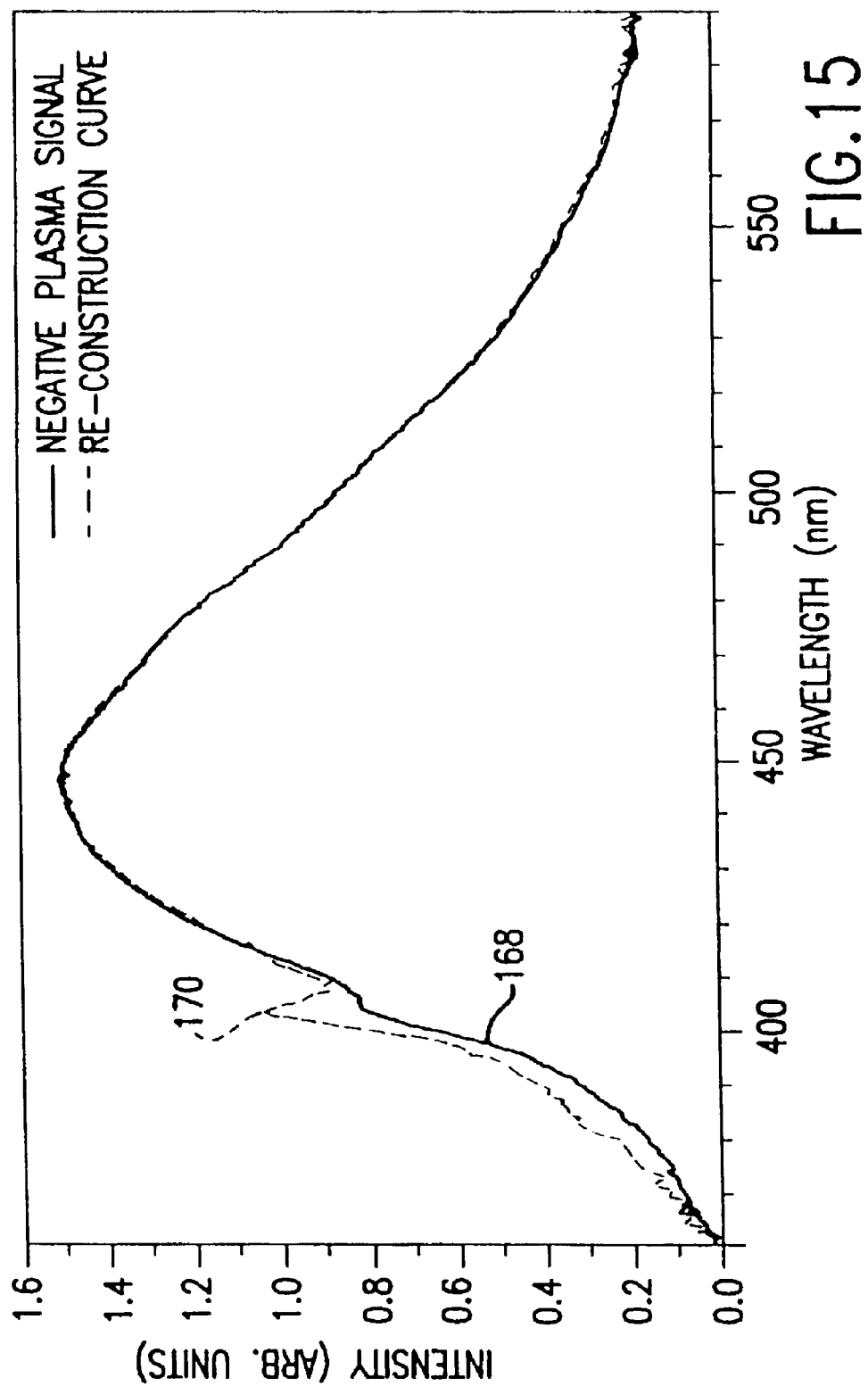

| LMC RUN # | DAYS SINCE FIRST BLEED | ELISA METHOD | CLINICAL DIANOSIS |
|---|---|---|---|
| 1 | 0* | .3 | NEG |
| 2 | 3 | .3 | NEG |
| 3 | 13 | .5 | NEG |
| 4 | 27 | .4 | NEG |
| 5 | 34 | 3.3 | POS |
| 6 | 50 | 3.4 | ↓ |
| 7 | 78 | 2.4 | |
| 8 | 163 | 2.4 | |
| 9 | 194 | 3.0 | |

*THIS MEANS LESS THAN 24-36 HOURS.

FIG.28

APPARATUS AND METHOD FOR INFECTIOUS DISEASE DETECTION

This application claims the benefit of U.S. Provisional Application No. 60/079,556, filed Mar. 27, 1998.

FIELD OF THE INVENTION

The present invention relates to the detection of the presence of infectious disease and more particularly to detection of the presence of HIV infection, Hepatitis A, B and C infection, and other similar infections by optical means.

BACKGROUND OF THE INVENTION

Optical systems have been used to determine chemical compositions of matters. Such optical systems include lasers which have long provided impetus to a wide range of spectroscopic investigations. The many advantages of lasers, such as their monochromaticity (ability to operate within a very narrow wavelength range), very high intensity compared to diffuse light sources, such as mercury lamps, and availability of inexpensive laser sources, are allowing many types of experiments and measurements not previously possible. Nowadays, the use of lasers in experiments or tests, such as absorbance or fluorescence measurements in chemical analysis, is routine.

Experiments or measurements based on the absorption or emission of light upon illumination of a sample by a light source have long been used to determine the nature of a sample's various components. The principle is based on the fact that given a high enough resolution for the measuring spectroscopic apparatus, every chemical component will give rise to a different absorption or emission (referred to hereinafter as fluorescence) spectrum which is a plot of the intensity of light absorbed or emitted by a sample measured at various wavelengths of the incident or emitted light. The absorption or fluorescence spectrum therefore corresponds to a fingerprint of a given chemical component, allowing its discrimination from other components present in the same sample.

Absorption or fluorescence spectroscopy has been an important technique for identification of unknown biological substances in aqueous (water-based) solutions. An absorption or fluorescence spectrum, of an aqueous solution, however, may be complicated by the fact that absorption bands of the various biological substances in the solution sometimes overlap, particularly in the case of large molecules, such as biomolecules, making assignments of their origins difficult. There is, in addition to absorption or fluorescence signals originating from a component of interest, a large amount of background noise generated by water and other constituents present in biological samples, such as blood or plasma.

Currently, a number of simple-to-operate, non-optical based analyzers for detection of certain infectious diseases, such as HIV infection, are commercially available. Examples of such analyzers are EKTACHEM DT 60, EKTACHEM 700P, REFLOTRON, AND SERALYZER. These systems allow tests to be performed in settings outside traditional laboratories, e.g., outpatient clinics, physicians' offices, and even shopping malls, schools, or churches. In addition, these systems offer the advantage of being economical, compact, lightweight, easy-to-operate, convenient, and requiring only a small amount of test sample. Some of these analyzers also have the potential for providing test accuracy precision similar to those obtained from more sophisticated analyzers used in large clinical laboratories. However, none of these commercially available analyzers are understood to be optical-based. Moreover, these systems are not suitable for analysis of a large number of samples. In addition, no such simple-to-operate system exists for detecting Hepatitis A, B or C infection.

Another drawback of available analyzers for detecting HIV infection is that they are not sufficiently sensitive and thus incapable of detecting HIV infection at the early stage of the infection. Only when the infection has occurred for some time such that the antibody or antigens of the HIV viruses in the blood sample reach detectable level, can the HIV infection be detected by conventional analyzers.

U.S. Pat. No. 5,267,152 to Yang et al. discloses an optical technique for a noninvasive measurement of blood glucose concentration using a near-infrared photodiode laser. Yang et al. determines the blood glucose concentration using an algorithm based upon the characteristic translational, vibrational and rotational motions of the molecules in the blood resulting from the excitation of the sample with a diode laser, and then comparing the optical signal from light reflected off the blood constituents with a calibration curve previously stored in the memory of a microprocessor. However, Yang et al. does not measure changes in the emission spectra of biological samples as a result of changes in the amounts of certain metabolites in the samples.

U.S. Pat. No. 5,258,788 to Furuya discloses an optical method for measuring the protein composition and concentration of the aqueous humor of the eye which, in addition to proteins, also contains blood cells. However, Furuya does not measure the emission of light by the constituents of a sample as a result of irradiation of the sample with a laser beam. Instead, it measures the scattering of incident light off the sample molecules rather than on the emission of light by the molecules themselves as a result of irradiation with a laser beam.

U.S. Pat. Nos. 5,238,810 and 5,252,493 both to Fujiwara et aL disclose an optical-based immunoassay method in which antigens or antibodies are labeled with microparticles of a magnetic substance to form a magnetic labeled body, thus allowing determination of minute amounts of the antigen or antibody. It would be desirable if viruses could be optically detected without the use of magnetic particles.

It is therefore an object of the present invention to provide identification of a wavelength range of an excitation laser beam within which the fluorescence spectrum of the sample will provide information that can be used to detect and identify any infectious disease present in the sample. Also the present invention provides for identification of a fluorescence wavelength range within which the fluorescence spectrum of a sample will yield information that may be used to detect and identify any infectious organism contained in the sample. Also various parameters obtained from the fluorescent spectrum of a sample may be used to detect and identify any infectious disease contained in the sample. Thus the present invention provides apparatus and method for detecting HIV infection at an earlier stage when they are yet to be detectable by conventional methods.

SUMMARY OF THE INVENTION

The present invention is directed to detection of presence of an infection in a plasma, which comprises the steps of (a) obtaining the plasma; (b) preparing a sample from the plasma; (c) directing laser light of a predetermined wavelength onto the sample; (d) obtaining an emission spectrum from the sample; and (e) comparing the emission spectrum with a control spectrum to determine presence of the infection in the sample. Preferably, the laser light has a wavelength between about 270 and 400 nanometers and more preferably, between about 310 and 370 nanometers.

In a preferred embodiment, a pulsed laser excitation at a selected wavelength is irradiated onto a plasma sample, and the resultant fluorescence spectra between a particular wavelength range of interest is detected and analyzed. The present invention allows for the differentiation between normal human plasma (uninfected) and plasma from individuals infected with human immunodeficiency viruses (HIV), Hepatitis A, B and C, and other similar infectious diseases.

In accordance with the preferred embodiment of the present invention, an excitation laser wavelength of about 355 nanometers (nm) is selected to generate fluorescence from a human plasma that will yields useful information for infectious disease detection and identification. In addition, a fluorescence wavelength range of about 380 nm to 600 nm is selected for fluorescence detection, because within this wavelength range, the fluorescence spectrum of the samples is found to provide useful information for infectious disease detection and identification.

In the preferred embodiment, excitation of human plasma is at approximately 355 nm, which elicits an emission spectrum attributed to a set of relatively lipophilic molecules associated with the metabolic status of the individual, such relatively lipophilic molecules being in large part bound to albumin and to low and very low density lipoproteins ("LDL"). Several parameters of these spectra have been identified which clearly differentiate HIV positive plasma from HIV negative plasma, or plasma infected with Hepatitis A, B or C from normal uninfected plasma. These parameters includes, but not limited to, the wavelength at which the peak emission intensity is obtained; the amplitude of the peak emission; and the area ratio of the left and right portions of the emission spectra (defined in detailed below). In addition, HIV positive and negative plasmas may be distinguished by using an algorithm having one or more of these parameters as variables.

In the present invention, plasma samples may be first treated with selective absorbents, such as C-M Affi Gel Blue or activated charcoal, to improve the discrimination of these parameters for infected and uninfected samples. For example, it is found that C-M Affi Gel Blue significantly shifts the peak wavelength of an emission toward a lower wavelength. Advantageously, this peak wavelength shift is significantly greater for HIV positive samples than for HIV negative (normal) samples, thus allowing improved discrimination of the HIV positive and negative samples on the basis of the peak wavelengths of the samples.

In addition, for samples treated with C-M Affi Gel Blue, it is also found that the intensity of the fluorescence peak is reduced more in HIV negative samples than in HIV positive samples,. This improves the discrimination of the HIV positive samples from HIV negative samples on the basis of intensity or amplitude of the emission peak. Further, it is found that HIV positive samples treated with activated charcoals exhibit a smaller shift of the emission band than in HIV negative samples treated with activated charcoal, which enhances the discrimination of the infected and uninfected samples on the basis of peak wavelengths.

The present invention provides a more sensitive detection of HIV infection particularly at the early stage of the infection than conventional diagnosis methods. For example, in instances where samples from an individual infected with HIV viruses at the early stage when the infection is still undetectable by conventional diagnosis, it is detected by using the method and apparatus of the present invention.

BRIEF DESCRIPTION OF THE DRAWINGS

These and other features, objects, and advantages of the present invention will become more apparent from the following detailed description in conjunction with the appended drawings in which:

FIG. 2a is a schematic circuit diagram of a detector/exposure control portion of the disease detection system;

FIG. 2b illustrates shutter and voltage waveforms of the detector/exposure control of FIG. 2a;

FIG. 15 illustrates the fluorescence spectrum of an HIV negative sample and a reconstructed spectrum;

FIG. 28 illustrates a table setting forth time and test results of the same samples of FIGS. 26A–C tested by conventional methods;

DETAILED DESCRIPTION OF THE INVENTION

Figure 1:
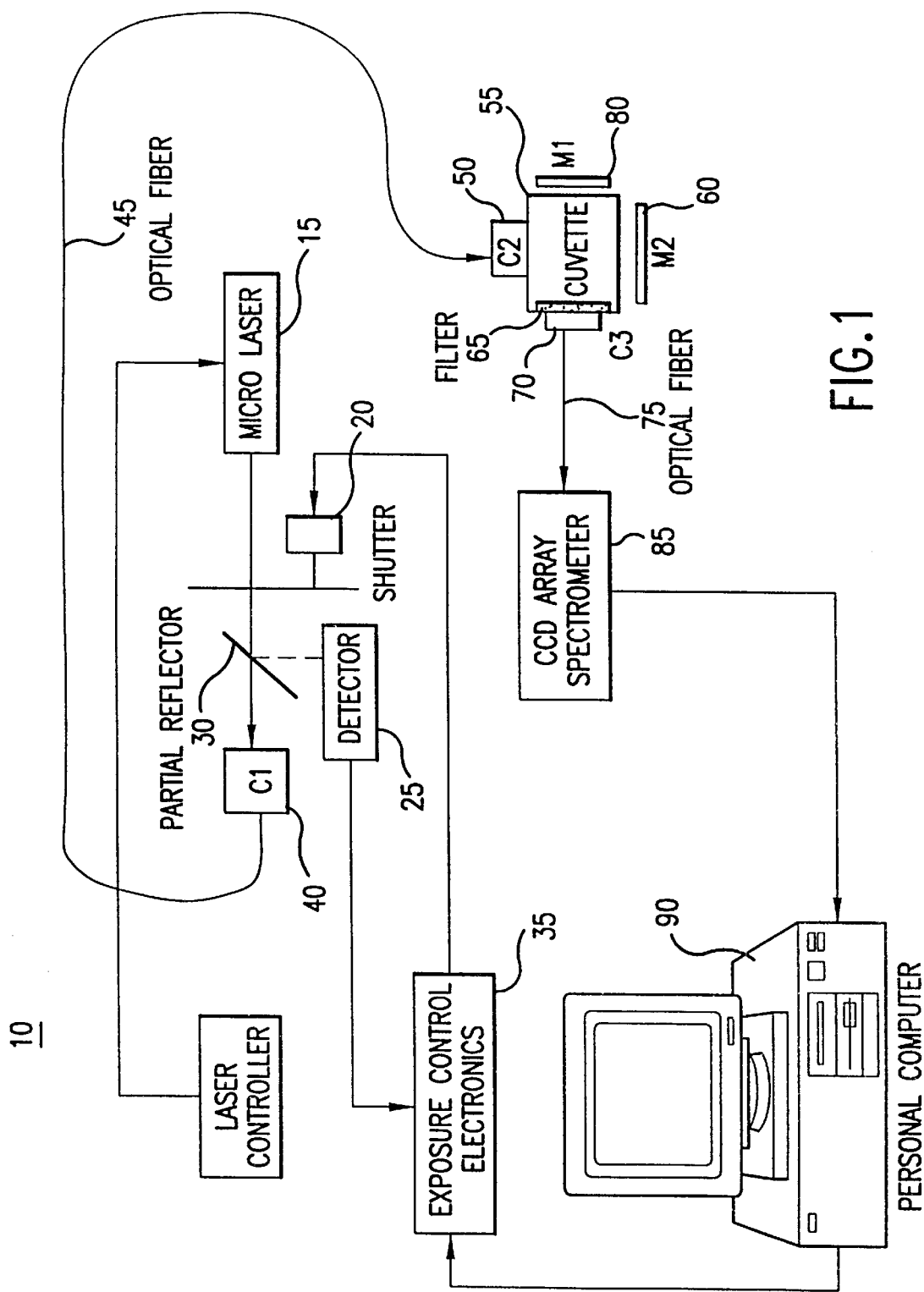
FIG. 1 is a schematic block diagram of an infectious disease detection system of the present invention.

A detection system 10 according to the present invention, in reference to FIG. 1, utilizes the bundling of a laser input (L), biologic phenomena (B) and signal recognition (S), which is referred hereinafter as an LBS system. This system provides for detecting infectious diseases and will be referred herein as an "Infectious Disease LBS". The System 10 uses a pulsed laser to excite human plasma at a selected wavelength and provides an analysis of parameters in the resultant fluorescence spectra about a particular wavelength range of interest. The Infectious Disease LBS of the present invention allows for the differentiation between normal human plasma and plasma from individuals infected with human immunodeficiency viruses (HIV), Hepatitis A, B and C, as well as other similar infectious diseases.

In accordance with the present invention, an excitation laser wavelength between about 270 nm and about 400 nm is selected to generate fluorescence from a human plasma that yields useful information that can be used for disease detection and identification. More preferably, the excitation laser wavelength is between about 310 nm and 370 nm. In the preferred embodiment described herein, an excitation laser wavelength of 355 nm is selected. This wavelength (i.e., 355 nm) is selected within the preferred excitation laser wavelength range (i.e., between about 270 nm and 400 nm) mainly because it is easily available from the particular laser source used by applicants; other wavelengths within the preferred wavelength range between about 310 nm and about 370 nm, such as 340 nm or 360 nm, may also be used for infectious disease identification and detection. Thus, in this respect, it should be understood that the present invention is not limited to the excitation laser wavelength of 355 nm as described herein. Applicants found that if the excitation laser wavelength is less than 270 nm or greater than 400 nm, the background fluorescence signal from human plasma that is not believed to significantly contribute to infectious disease detection becomes so great that signals useful for infectious disease detection are not easily distinguishable from this background signal. In addition, according to the present invention, a fluorescence wavelength range of about 380 nm to about 600 nm is identified by applicants as the fluorescence wavelength range that provides useful information for disease detection and identification.

An important aspect of the present invention is that excitation of human plasma by a laser excitation having a wavelength within the range of about 270 nm to 400 nm, and more preferably within the range of about 310 nm to 370 nm, and such as 355 nm, elicits an emission spectrum which is attributed to a set of relatively lipophilic molecules associated with the metabolic status of the individual, such relatively lipophilic molecules being in large part bound to albumin and to low and very low density lipoproteins. As will be detailed below, several parameters of these spectra have been identified which clearly differentiate HIV positive plasmas from HIV negative plasmas; or plasmas infected with Hepatitis A, B or C and normal, uninfected plasmas. According to the present invention, HIV positive and negative plasmas are distinguished by their respective wavelengths ($\lambda_{max}$) at which their respective emission intensity profile exhibit maximum emission intensities (or amplitudes), and by the relative values of such the maximum intensities ($I_{max}$) (or amplitude which is proportional to the square root of intensity). In addition, according to the present invention, additional parameters, beside $\lambda_{max}$ and $I_{max}$, for distinguishing HIV positive plasmas from HIV negative plasmas are also provided. One of such parameters is the so-called area ratio, $A_r$, which will be defined in detail.

In accordance with the preset invention, chromatography of the plasma through certain absorbents differentially alter these parameters in HIV positive plasma and HIV negative plasma samples, allowing a greater identification and distinction of an HIV positive sample. These absorbents include C-M Affi Gel Blue (hereinafter also referred to as "CM-AGB") and activated charcoal. It is found that the emission spectra of a plasma sample, after it is treated with CM-AGB, exhibit a significant shift in wavelength towards lower wavelength. Advantageously, this shift is significantly greater for HIV positive samples (about 12–18 nm) than for HIV negative (normal) samples (about 4–8 nm). This effect helps to more clearly discriminate the HIV positive samples and HIV negative samples. It is also found that the intensity of the fluorescence peak, $I_{max}$, is reduced more in HIV negative plasma samples than in HIV positive plasma samples by C-M Affi Gel Blue treatment.

Applicants also found that activated charcoal treatment of the plasma samples results, advantageously, in a relatively smaller shift (towards shorter wavelengths) of the emission band for HIV positive samples (about 1–2 nm) than for HIV negative samples (about 5–8 nm).

Referring to FIG. 1, in a preferred embodiment, an Infectious Disease LBS system 10 of the present invention includes a frequency-tripled NdYag laser 15 having an emission wavelength of about 355 nm, an average power of about 2 milliwatts, and pulsed at a high repetition rate (e.g., 10 Hz or 20 Hz) by a mechanical shutter 20. When shutter 20 is open, a small portion of the laser beam emitted by laser 15 is reflected into a silicon detector 25 by a beam splitter 30 as input to a beam monitor 35. A schematic circuit diagram of beam monitor 35 is depicted in FIG. 2A. Beam monitor 35 monitors the total amount of light irradiated onto the sample to ensure that each sample under test is irradiated with the same amount of light. More specifically, an diode detector 25 detects the portion of light reflected by mirror 30. A circuit including a pre-amplifier 26 measures the total amount of light irradiated on detector 25 and when it reaches a predetermined level, a comparator 27 triggers a control flip flop to control a shutter solenoid 29 to turn off the shutter. FIG. 2B illustrates the waveforms of the shutter and voltages at P1 and P2 of the monitor circuit The remainder of the laser beam, after passing beam splitter 30, goes into a focusing lens 40 which focuses the beam into an optical fiber 45, the output of which is connected to a lens 50. Lens 50 collimates the laser beam before providing it into a quartz cuvette 55 containing a sample to be tested (analyte). A mirror 60 is used to approximately double the effective excitation energy. When the laser beam is irradiated onto the sample contained in cuvette 55, an optical emission is produced by the sample, which passes through a high-pass optical filter 65 to cut off any scattered light of a wavelength of 355 nm (the input laser wavelength) from the laser source, thereby ensuring that the scattered light from the input excitation beam does not interfere with the emission originating from the sample. The sample emission is then collected by another focusing lens 70, which focuses and provide the sample emission into another optical fiber 75. Another reflective mirror 80 is used to effectively approximately double the sample fluorescence collection efficiency. The output of optical fiber 75 is connected to a CCD (charge-coupled device) array spectrometer 85 which collects the fluorescence spectrum of the emission from the sample. The output signal from CCD spectrometer 85 is provided to a personal computer 90 which is used to initiate the data collection sequence, collect data from the spectrometer, and perform the analysis as detailed below.

In accordance with the present invention, the fluorescence spectrum of human plasma of a person is used to determine if that person is infected with certain infectious diseases, such as HIV, Hepatitis A, B and C, or other similar infectious disease. Human plasma contains as many as 100 to 125 proteins, many of which, such as albumin and the lipoproteins, serve as carriers for smaller metabolically important molecules, as well as their metabolites. Applicants of the present invention discovered that the emission spectrum between about 380 nm and about 600 nm can be ascribed to a limited number of these constituents, and these constituents, when present in different relative concentrations, result in a spectrum in which the total fluorescence and emission maximum is shifted to relatively shorter wavelengths for HIV positive plasmas, and to longer wavelengths for HIV negative plasmas.

Figure 3A:
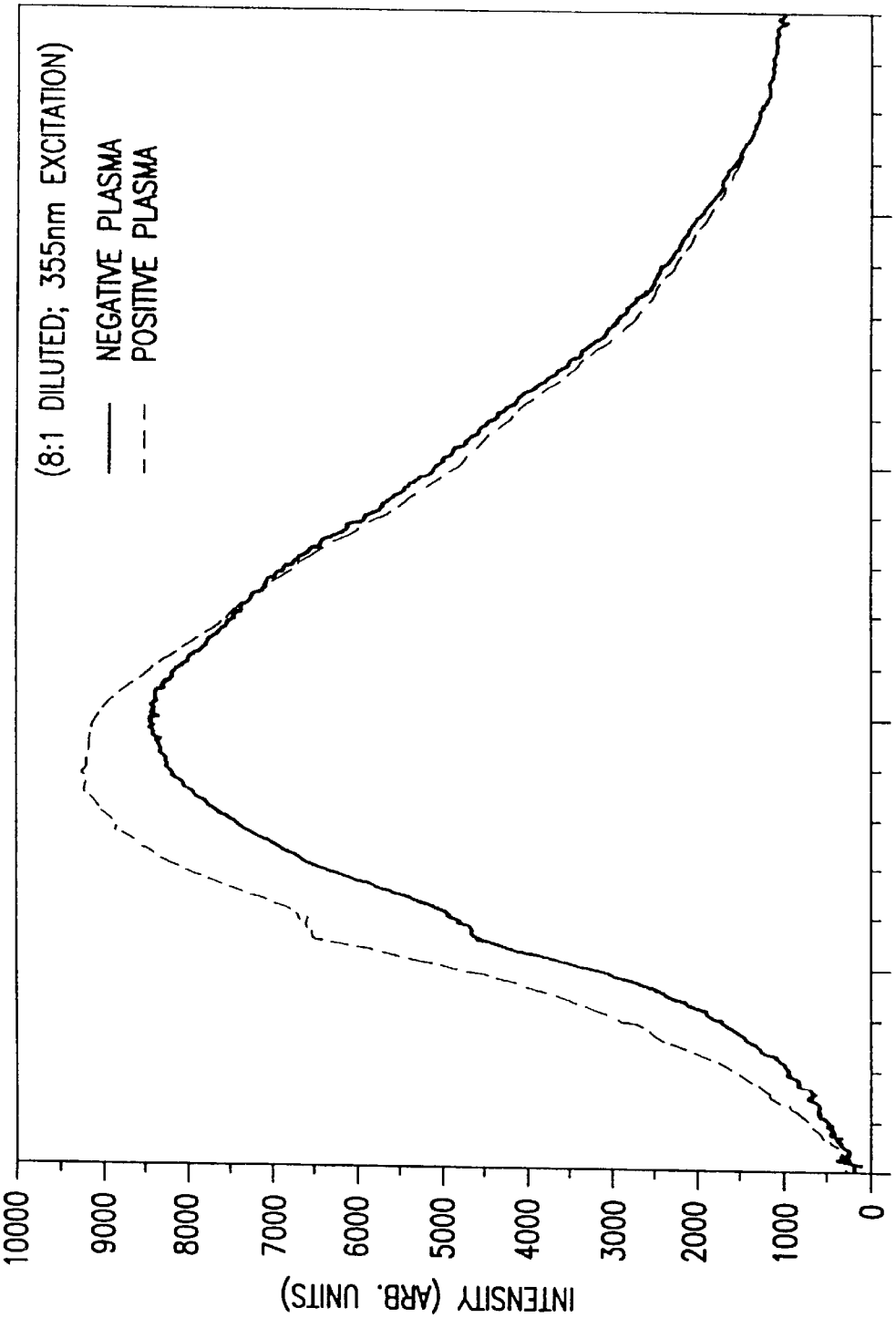
FIG. 3A shows fluorescence spectrums of an HIV negative plasma sample and HIV positive plasma sample produced at an excitation wavelength of 355 nm and detected within the wavelength range of 350 nm to 600 nm.
Figure 3B:
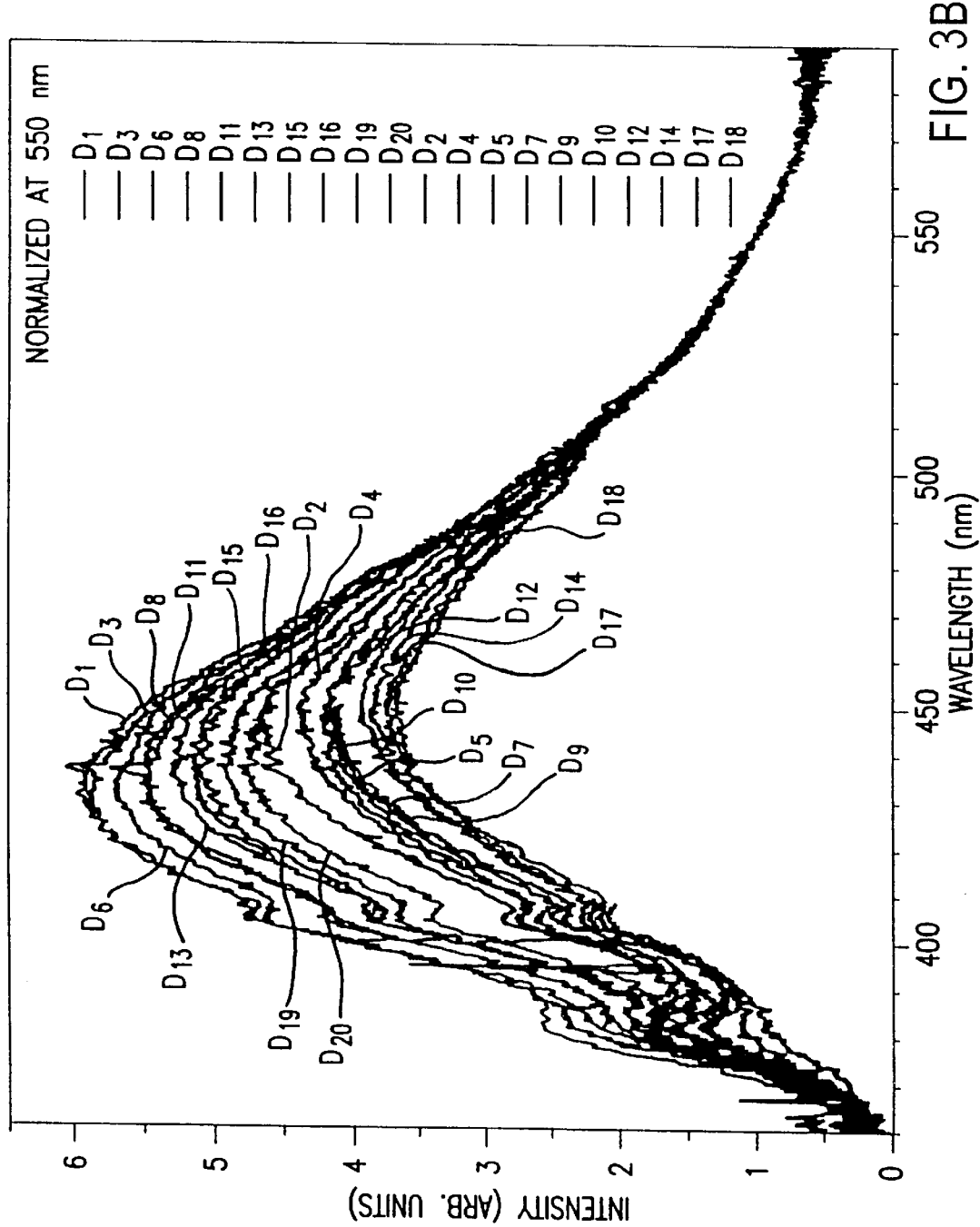
FIG. 3B shows fluorescence spectrums of a group of HIV positive plasma samples and a group pf HIV negative plasma samples.

Referring to FIG. 3, which shows the emission spectra of HIV negative (a solid line) and positive (a broken line) whole plasma samples, it is demonstrated that the fluorescence spectrums for the HIV negative plasma and HIV positive plasma exhibit difference peak locations (i.e., wavelength maxima) at which the spectrums exhibit a maximum intensity and different relative intensity (i.e., amplitude). This is further demonstrated by the emission spectrums of HIV positive plasmas (D1, D3, D6, D8, D11, D13, D15, D16, D19 and D20) and emission spectrums of HIV negative samples (D2, D4, D5, D7, D9, D10, D12, D14, D17 and D18) shown in FIG. 3A. There is a clear separation between the HIV positive spectra group and the HIV negative spectra group.

In accordance with the present invention, methods are provided to alter both the amplitude and wavelength maxima of the plasma spectrum to further discriminate HIV positive and negative samples. It is believed that these methods alter the relative concentration of the contributing fluorophores (the constituents that give rise to the observed fluorescence), which results in the shift in the amplitude and wavelength maxima of the samples. These findings are supported by the following experiments or tests conducted by applicants.

Figure 4:
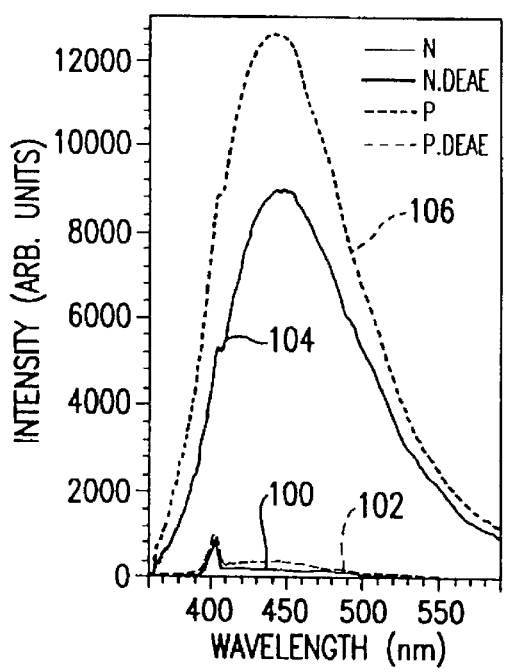
FIG. 4 illustrates the fluorescence spectrums of HIV negative and positive samples as well as such samples treated with DEAE-Affi Gel Blue.

Referring to FIG. 4, the fluorescence emission of eluates obtained by chromatographic absorption of plasma on DEAE-Affi Gel Blue (BioRad Laboratories) (which essentially represent purified immunoglobulins) shows that it contains less than 2 percent of the fluorescent signal from whole plasma, indicating that the emission profile of the plasma is not due to immunoglobulins. FIG. 4 shows the emission spectrum of eluates made by chromatographic absorption of an HIV negative sample (designated as 100—a thick solid line); the emission spectrum of eluates made by chromatographic absorption of an HIV positive sample (designated as 102—a thick broken line); the emission spectrum of a whole plasma of an HIV negative sample (designated as 104—a thin solid line); and the emission spectrum of a whole plasma of an HIV positive sample (designated as 106—a thin broken line).

Figure 5:
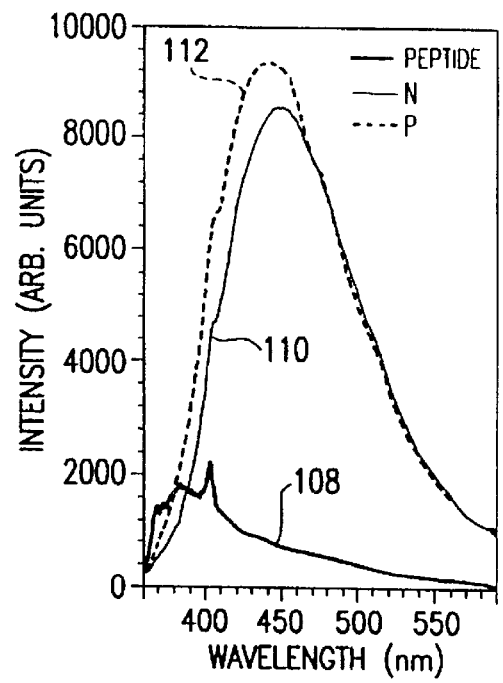
FIG. 5 illustrates the fluorescence spectrums of peptide, HIV positive and negative samples.

Referring to FIG. 5, applicants found that purified synthetic polypeptides containing 18 of the most commonly occurring amino acids, including phenylalanine, tyrosine, proline and tryptophan, fail to give a significant emission spectra, which indicates that the emission profile of whole plasma in the wavelength range of about 350 nm to about 600 nm is not directly due to a protein or polypeptide. FIG. 5 shows the emission spectrum of the purified synthetic polypeptides (designated as 108—a thick solid line); the emission spectrum of an HIV negative whole plasma sample (designated as 110—a thin solid line); and the emission spectrum of an HIV positive whole plasma sample (designated as 112—a broken line).

Figure 6A:
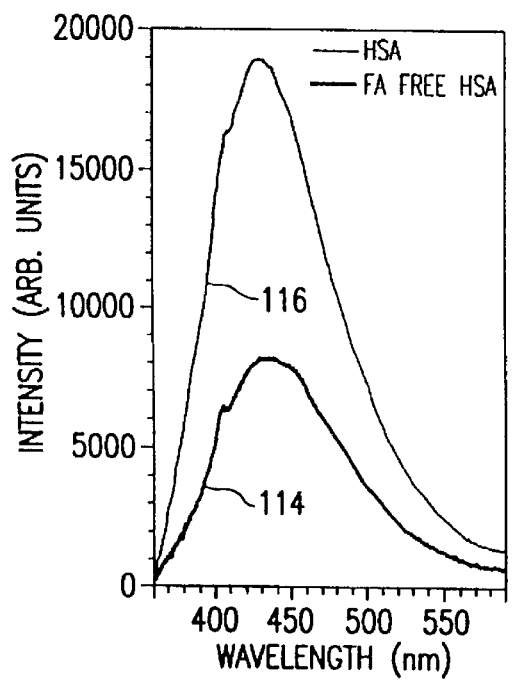
FIG. 6A illustrates the fluorescence spectrums of holo-albumin (HSA) and fatty acid free albumin.
Figure 7:
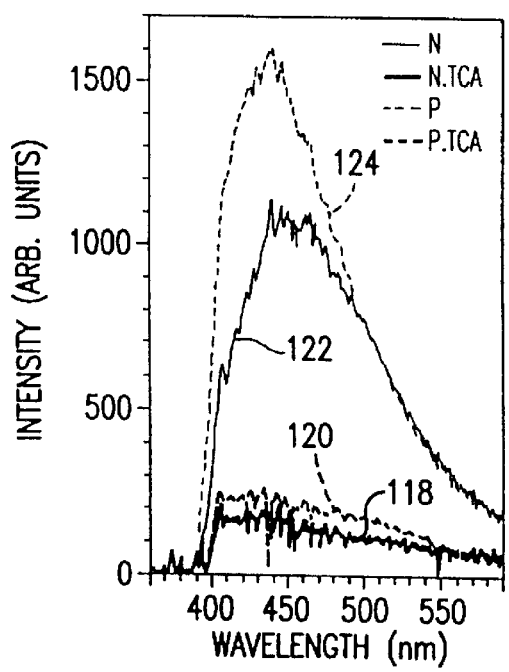
FIG. 7 illustrates the fluorescence spectrums of HIV positive and negative samples as well as such samples treated with TCA.
Figure 6B:
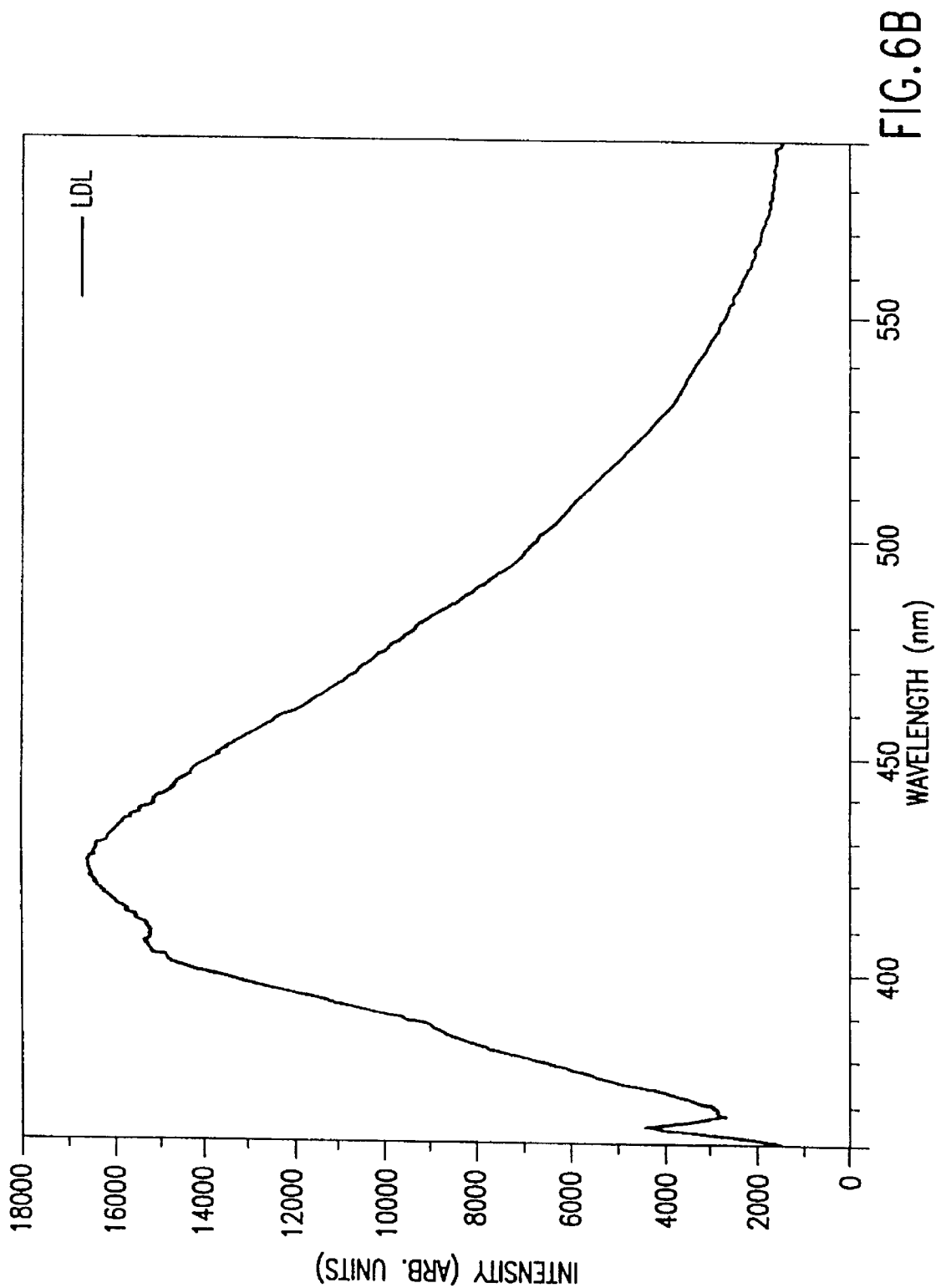
FIG. 6B illustrates the fluorescence spectrum of LDL.

Referring to FIGS. 6A and 6B, analysis of commercially obtained human serum albumin (HSA) (FIG. 6A) and low density lipoprotein ("LDL")(FIG. 6B) shows that each yields an emission profile very similar to that obtained from whole plasma. In FIG. 6A, the emission spectrum designated as 114 (a thick solid line) is obtained from a fatty acid free HSA sample; and the emission spectrum designated as 116 (a thin solid line) is obtained from an HSA sample. Since purified polypeptides yield virtually no emission signal, applicants concluded that the HSA and LDL emission signals result from molecules bound to them, but not due to the protein itself. This is in part confirmed by applicants by taking the fluorescence spectrum of albumin commercially treated with charcoal to remove lipids and other relatively hydrophobic molecules ("essentially fatty acid free albumin")( see emission spectrum designated as 114 of FIG. 6A): the resulting spectrum showed an emission band which has a much reduced intensity relative to that of holo-albumin. From these results, it is concluded that the observed shift in the emission spectra suggests the removal by charcoal of some fluorophores which may contribute to a positive (with HIV viruses) or negative (no detectable HIV viruses) spectra. Similar tests by applicants with LDL adsorbed by charcoal show a significant decrease in total fluorescence as well as a shift in the spectrum, which suggests that charcoal removes mainly those components bound to LDL that contribute to the emission profile. It is therefore concluded by applicants that charcoal shifts negative HIV plasma, but not HIV positive plasma Referring to FIG. 7, plasma in which proteins were precipitated out using trichloroacetic acid ("TCA") yields a fluorescence spectrum showing a significantly reduced emission intensity relative to that of whole plasma. Applicants thus confirmed that the source of the emission spectra in the wavelength range of interest may be bound to proteins including albumin and LDL. In FIG. 7, the emission spectrum designated as 118 (a thick solid line) is obtained from an HIV negative plasma sample treated with TCA; the emission spectrum designated as 120 (a thick broken line) is obtained from an HIV positive plasma sample treated with TCA; the emission spectrum designated as 122 (a thin solid line) is obtained from the HIV negative plasma; and the emission spectrum designated as 124 (a thin broken line) is obtained from the HIV positive plasma sample.

Figure 8:
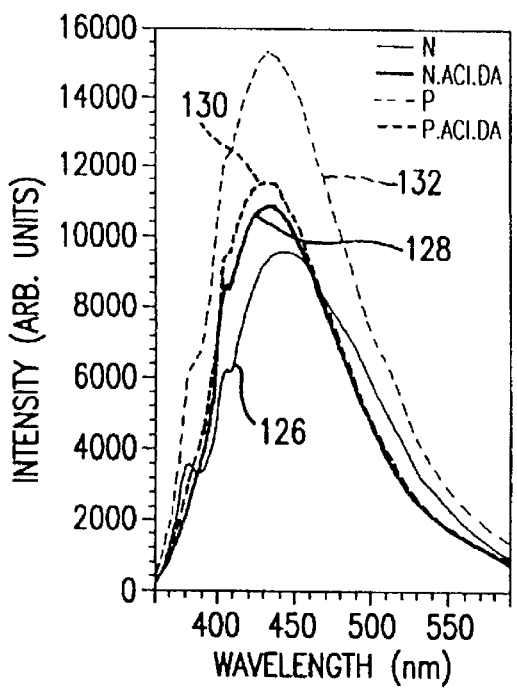
FIG. 8 illustrates the fluorescence spectrums of HIV positive and negative samples as well as such samples acidified and dialyzed.

Referring to FIG. 8, the hydrophobicity of these constituents or the hydrophobic rather than the ionic nature of their binding to a protein was demonstrated by the results of experiments which showed little change in spectra upon changing the charge on plasma proteins with acidification to pH 4.0 and subsequent dialysis using membranes with a molecular weight cutoff of 12 kilodaltons. In FIG. 8, the emission spectrum designated as 126 (a thin solid line) is obtained from an HIV negative plasma sample; the emission spectrum designated as 128 (a thick solid line) is obtained from the same HIV negative plasma sample treated by the above described acidification and dialysis process; the emission spectrum designated as 130 (a thick broken line) is obtained from an HIV positive plasma sample treated by the above described acidification and dialysis process; and the emission spectrum designated as 132 (a thin broken line) is obtained from the same HIV positive plasma sample treated by the above described acidification and dialysis process.

Figure 9A:
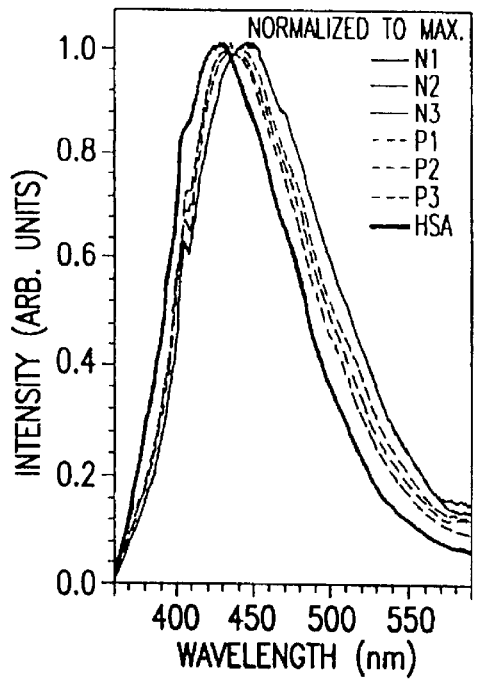
FIG. 9A illustrates the fluorescence spectrums of a group of HIV positive and HIV negative samples and an HSA sample.
Figure 9B:
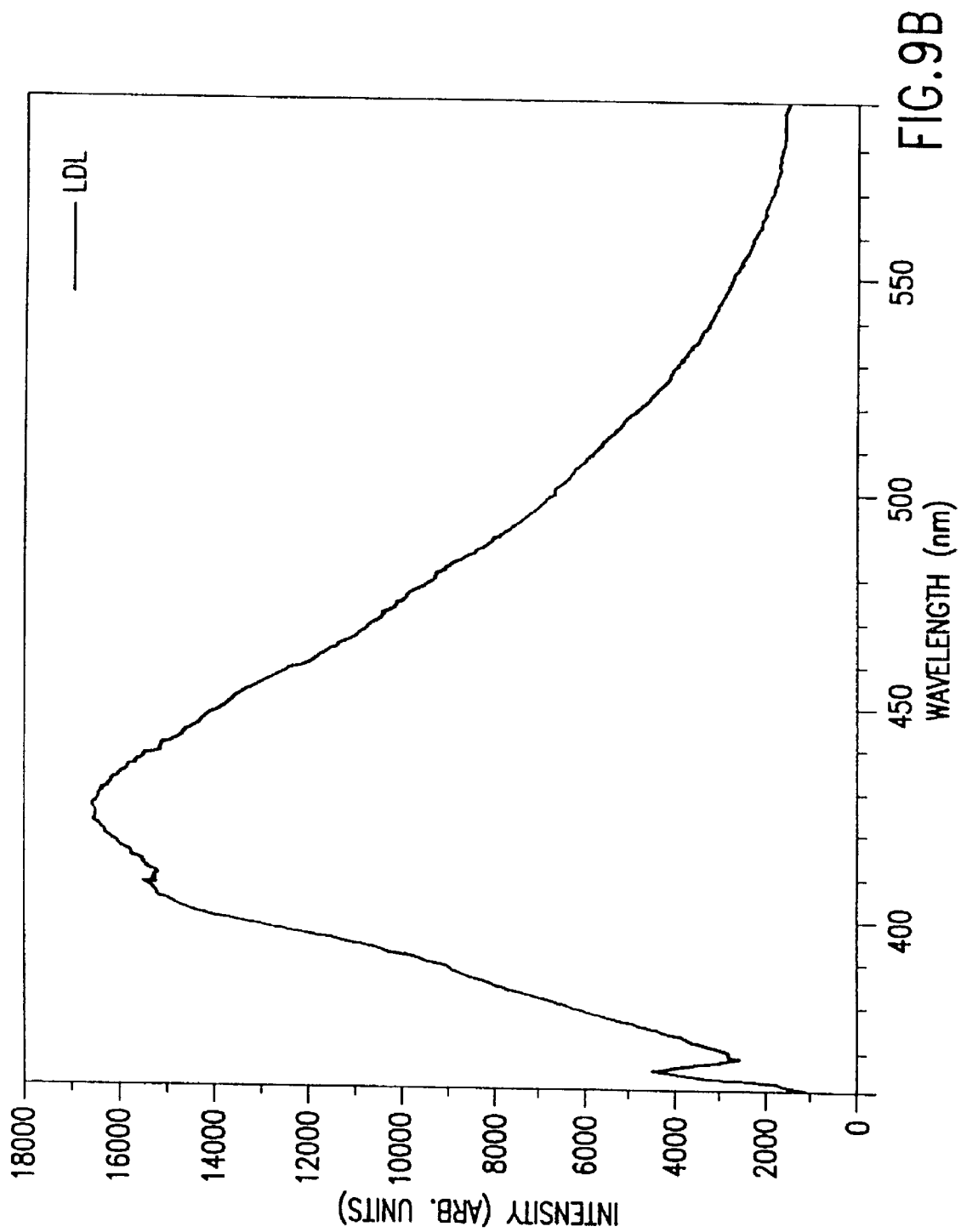
FIG. 9B illustrates the fluorescence spectrum of LDL.

Referring to FIGS. 9A and 9B, the spectra of commercially obtained holo-albumin and LDL closely approximate the spectrum of human plasma. This indicates that a large proportion of the constituents which contribute to the overall emission profile are bound to albumin and LDL.

Figure 10:
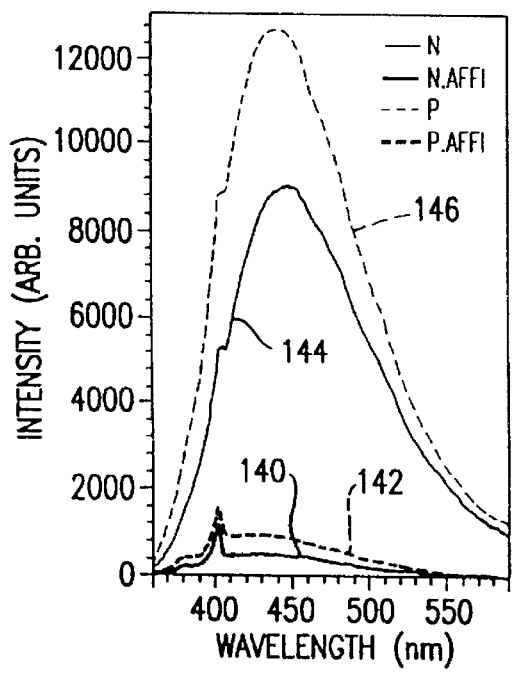
FIG. 10 illustrates the fluorescence spectrums of HIV positive and HIV negative samples, respectively, and such samples treated with CM-Affi Gel Blue (CM-AGB)

Referring to FIG. 10, it has been discovered by applicants that all formulations of CM-Affi Gel Blue (AGB) columns, if used in a high enough ratio relative to plasma, will remove some or all of the fluorescence emission signal. This suggests that this gel has affinity for at least some or all of the fluorophores present in the sample plasma. Cibacrom gels, which contains the same Cibacrom dyes that in CM-AGB, bind other proteins as well, and one common feature of many these proteins is their ability to bind to NADH. It is believed that NADH may acts as a contributing fluorophores in the plasma samples. In FIG. 10, the emission spectrum 140 (a thick solid line) is obtained from an HIV negative sample plasma treated with AGB; the emission spectrum 142 (a thick broken line) is obtained from an HIV positive sample plasma treated with AGB; the emission spectrum 144 (a thin solid line) is obtained from the same HIV negative sample plasma without the AGB treatment; the emission spectrum 146 (a thin broken line) is obtained from the same HIV positive sample plasma without the AGB treatment.

Figure 11:
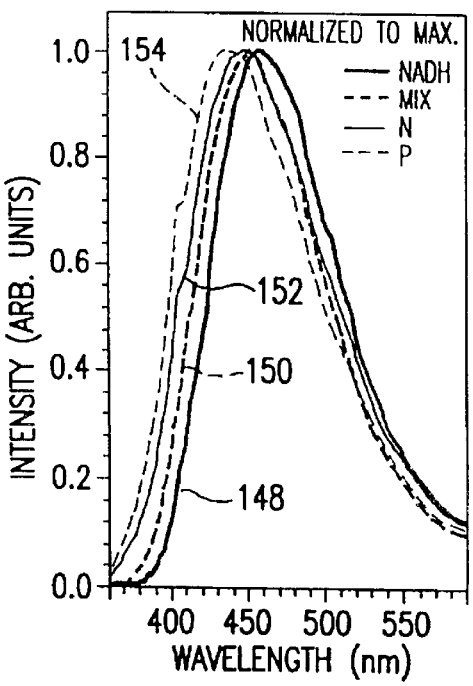
FIG. 11 illustrates the fluorescence spectrums of HIV positive and HIV negative samples, an NADH sample and a sample of a mixture of NADH and HSA.

Referring to FIG. 11, analysis of NADH (reduced nicotinamide adenine dinucleotide) yielded a spectrum which overlaps with the spectrum of whole human plasma derived from a negative plasma, also referred to in this application as a "normal" plasma. Applicants found that the oxidized form, NAD, has no fluorescence in the 380–600 nm wavelength range so that oxidation of a sample resulting in the conversion of NADH to NAD could lead to false positives Subsequent studies mixing NADH with "essentially fatty acid free" (charcoal treated) albumin gave an emission spectrum which even more closely resembled the negative plasma's emission profile. These results indicate that NADH, possibly in a protein bound form, is an important contributor to the plasma's emission profile. In fact, it has been documented that the presence of HIV viruses results in a reduction in niacin and NADH through the effects of interferon gamma's induction of the catabolism of tryptophan, the obligatory precursor to niacin. In FIG. 11, an emission profile designated as 148 (a thick solid line) is obtained from NADH; an emission profile designated as 150 (a thick broken line) is obtained from a mixture of NADH and HSA; an emission profile designated as 152 (a thin solid line) is obtained from an HIV negative sample plasma; and an emission profile designated as 154 (a thin broken line) is obtained from an HIV positive sample plasma.

Figure 12:
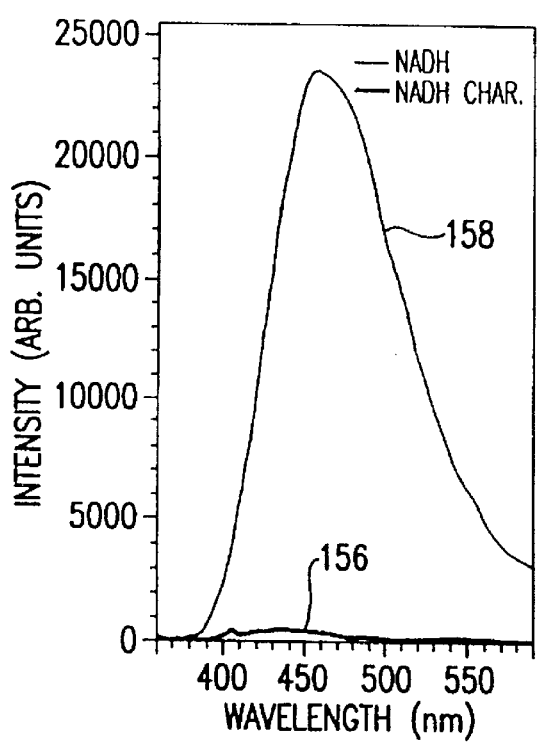
FIG. 12 illustrates the fluorescence spectrums of an NADH sample and such sample treated with activated charcoal.

Referring to FIG. 12, additional studies by applicants have served to reinforce the importance of NADH. Chromatography of plasma through charcoal results in a large reduction in fluorescence while a similar exposure of NADH to charcoal quantitatively removes its signal. In a complex mixture of fluorophores, the relatively selective removal of some fluorophores, such as NADH, results in a shift in the wavelength of maximum absorption of the aggregate emission spectrum. NADH emits on the long wavelength side of the plasma emission maximum. Thus, any treatment that results in the relatively selective removal of NADH is expected to lead to an overall shift of the emission band towards shorter wavelengths. Applicants found this to be true for all plasma treated with activated charcoal. Moreover, applicants found that a charcoal-treated HIV negative plasma exhibits a greater shift of the fluorescence maximum towards shorter wavelengths than a charcoal-treated positive plasma sample, which suggests that NADH or related molecules have a greater contribution to the emission arising from a negative plasma sample than to that arising from a positive. In FIG. 12, an emission profile designated as 156 (a solid thick line) is obtained from a charcoal treated NADH sample; and an emission profile designated as 158 (a thin solid line) is obtained from an NADH sample.

Figure 13:
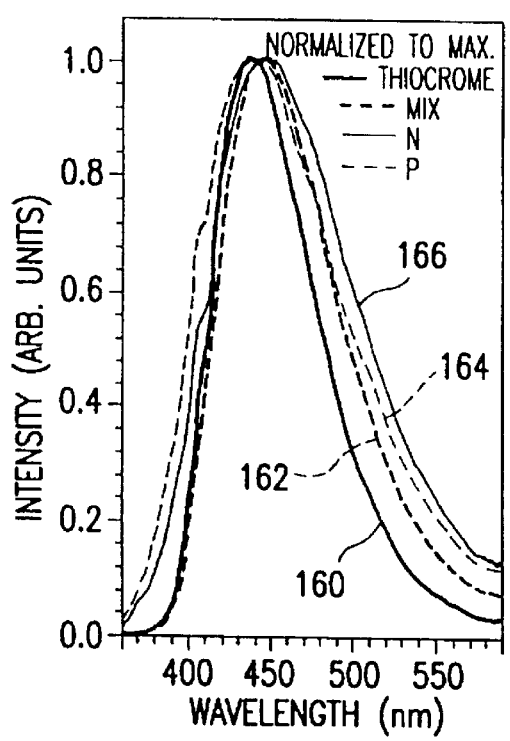
FIG. 13 illustrates the fluorescence spectrums of thiocrome, a mixture of thiocrome, NADH and HSA, and HIV positive and negative samples.
Figure 14A:
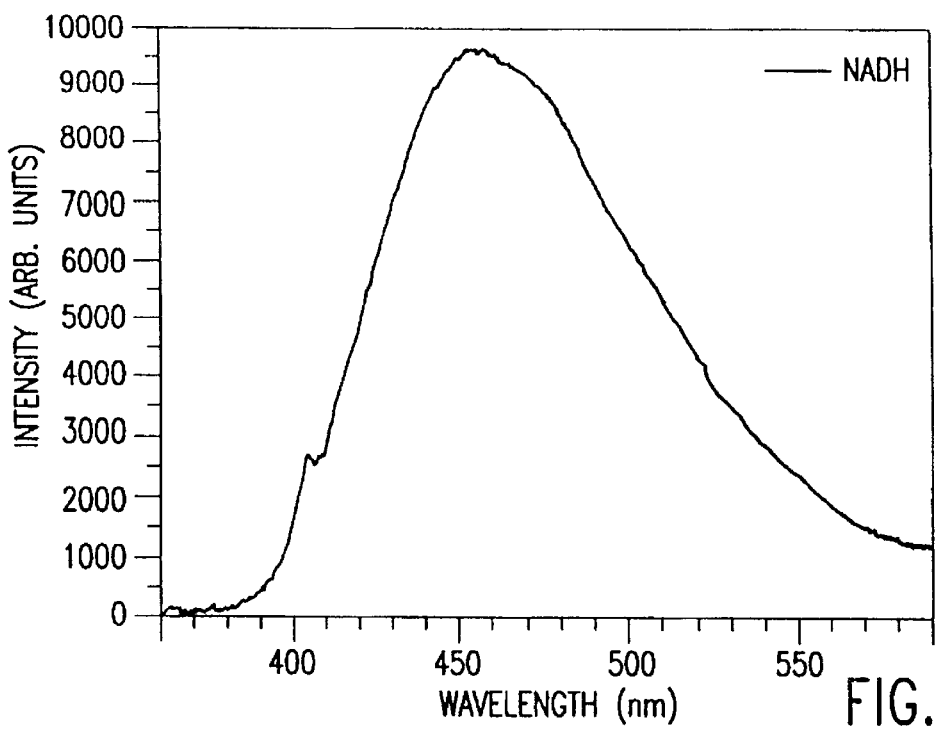
FIGS. 14A–D illustrate the fluorescence spectrums of NADH, thiocrome, riboflamin, and HDL.
Figure 14B:
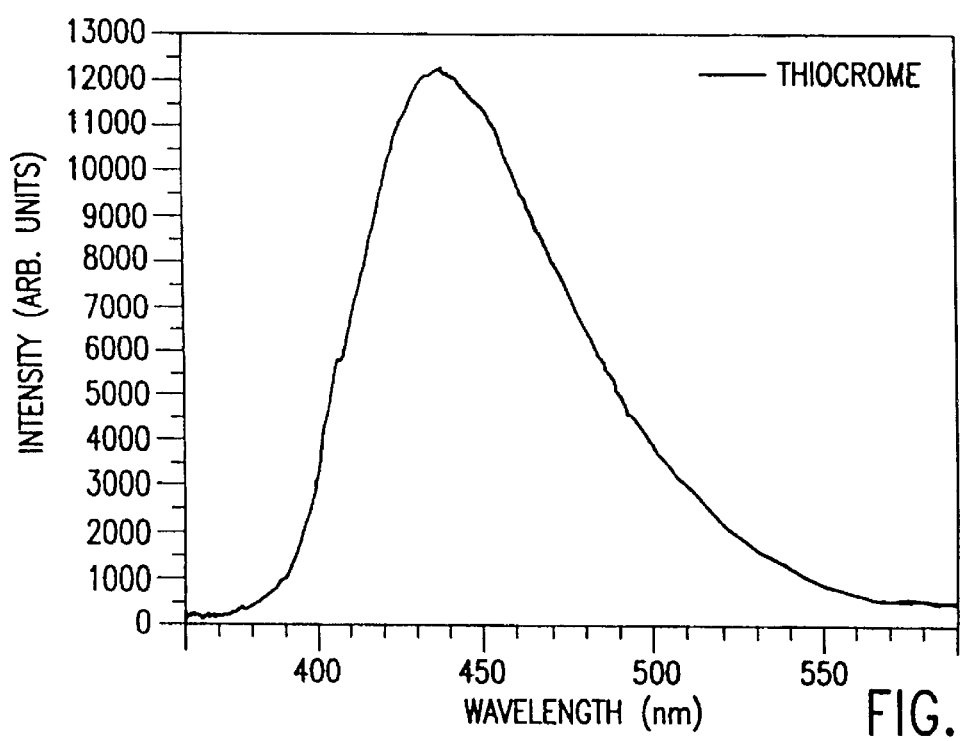
Figure 14C:
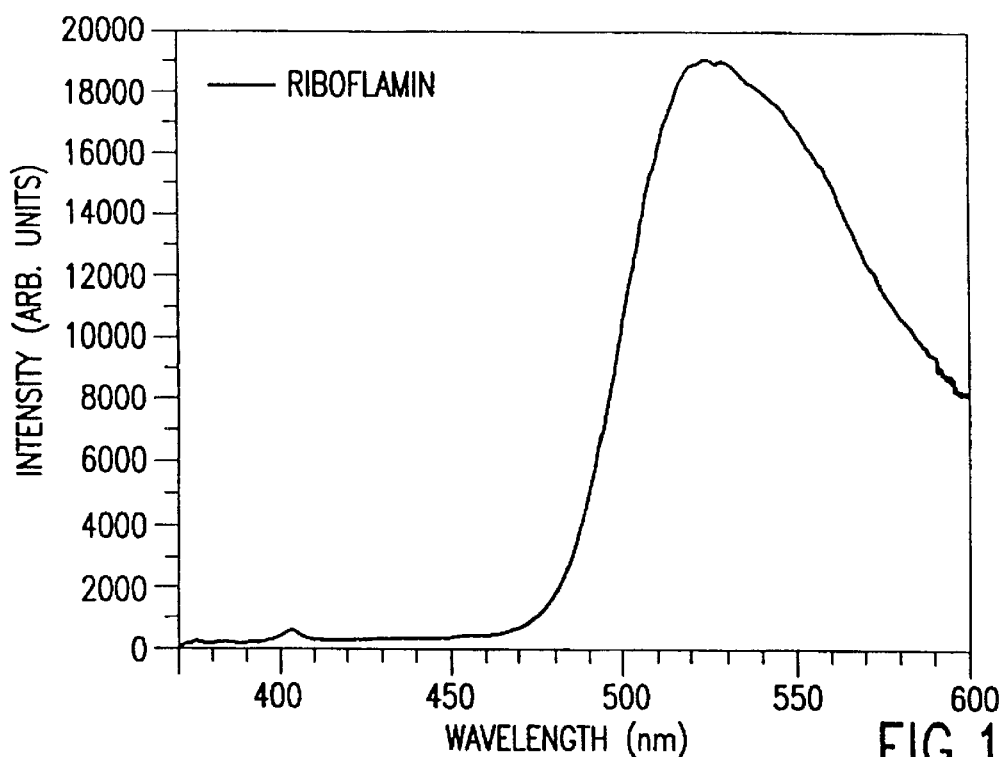
Figure 14D:
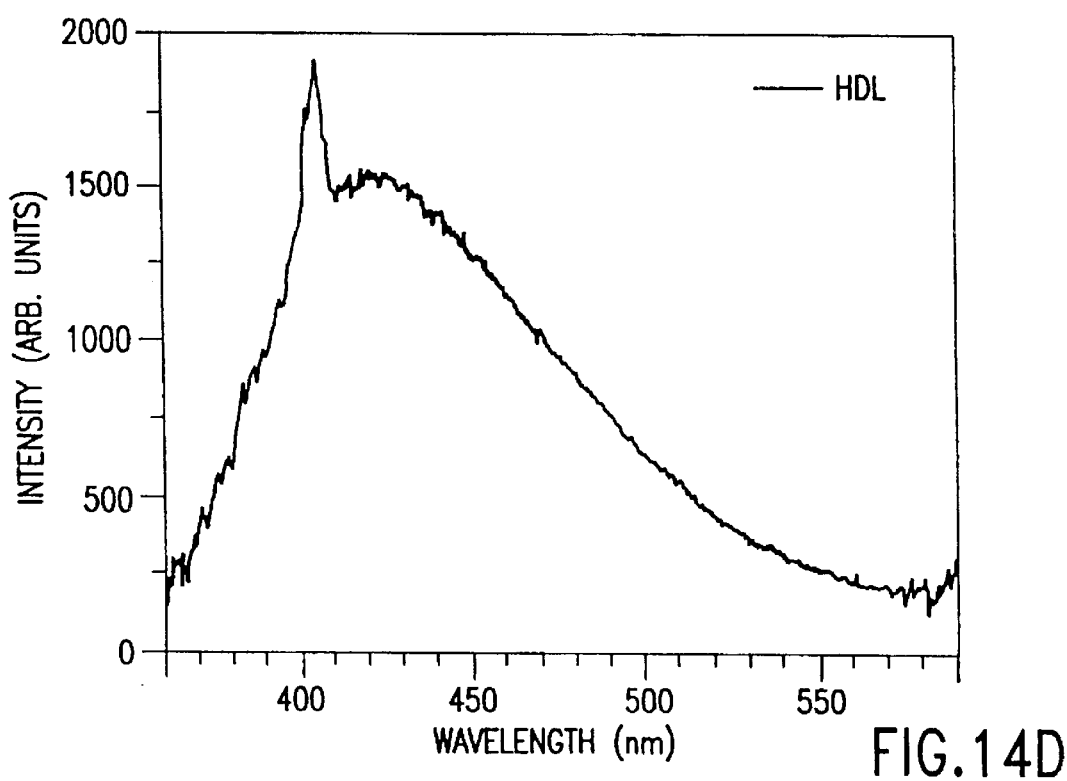

Referring to FIG. 13, analysis of the thiamine metabolite, thiochrome, yielded an emission spectrum with a maximum very similar to those of HIV positive samples. FIG. 13 shows the emission profiles obtained, respectively, from thiochrome (designated as 160, a thick solid line), a mixture of thiochrome, NADH and HSA with certain proportions (designated as 162, a thick broken line), an HIV positive plasma sample (designated as 164, a thin broken line), and an HIV negative plasma sample (designated as 166, a thin solid line). It is shown that the mixed sample containing NADH, thiochrome and albumin yielded a spectrum similar to that of a whole plasma sample. These data suggest that these metabolites (NADH, thiochrome, and albumin), in both free and bound forms, make important contributions to the emission spectrum of a human plasma. For completeness, the emission profiles of samples of NADH, thiochrome, riboflamin and HDL are shown in FIGS. 14A–D, respectively.

In addition, these data allow one to determine dynamic conditions in which an individual's metabolic status can be assessed based on steady state changes in the relative amounts of these metabolites and similar molecules. As an example, alterations in the relative contributions of the aforementioned metabolites may be made to coincide with either HIV positive or negative plasma, the extent of alteration required thus providing an indication of the relative amounts of metabolites present in the HIV positive or negative plasma. FIG. 15 shows the emission profile of an HIV negative plasma sample (designated as 168—a thin solid line), and that of a sample having a mixture of NADH, thiochrome, and albumin having proportions so that its mission profile (designated as 170—a thin broken line) approximately matches that of the negative HIV plasma sample. FIG. 16 shows the emission profile of an HIV positive plasma sample (designated as 172—a thin solid line), and that of a sample having a mixture of NADH, thiochrome, and albumin having proportions so that its mission profile (designated as 174—a thin broken line) approximately matches that of the negative HIV plasma sample.

Figure 16A:
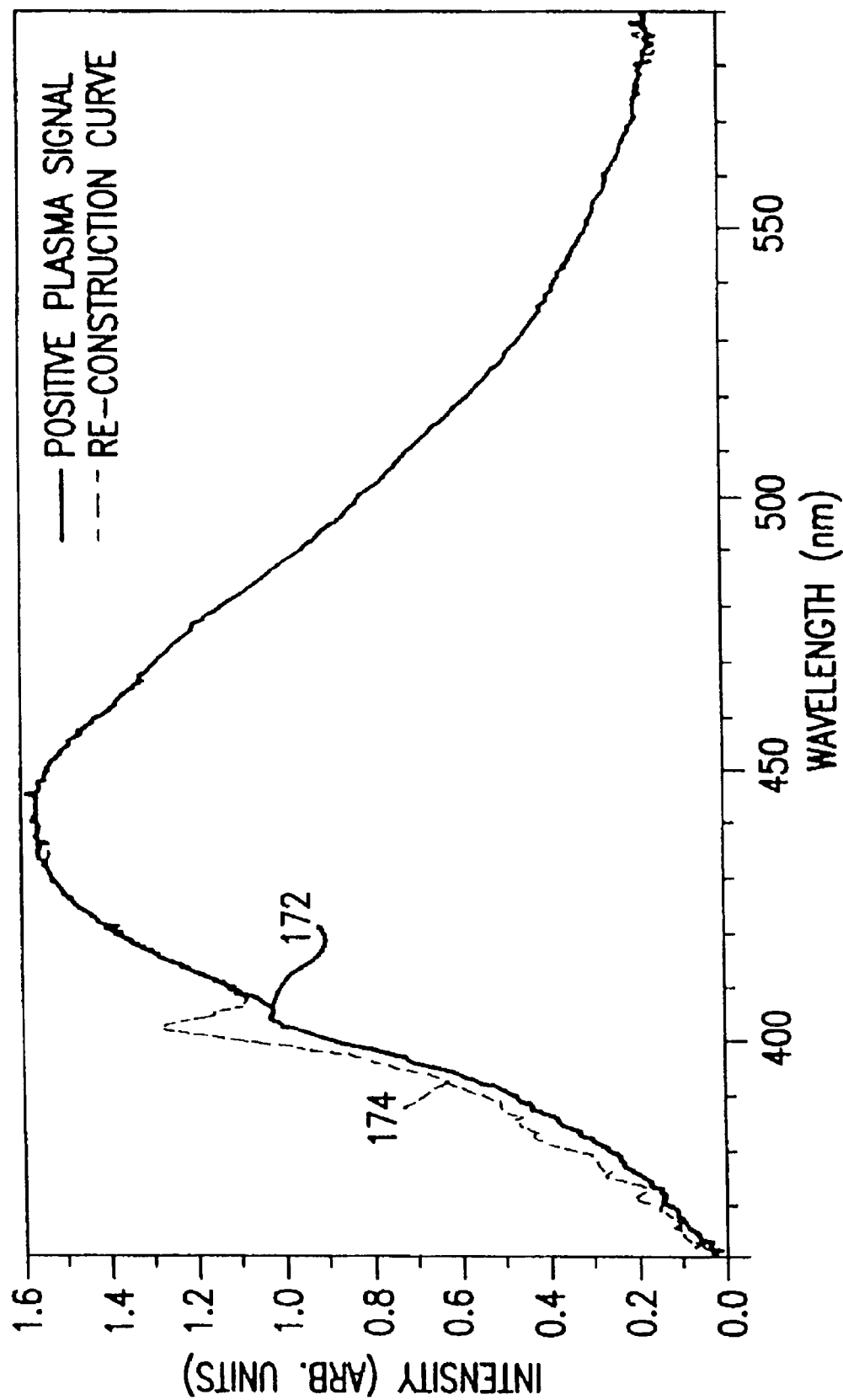
FIG. 16A illustrates the fluorescence spectrum of an HIV positive sample and a reconstructed spectrum.
Figure 16B:
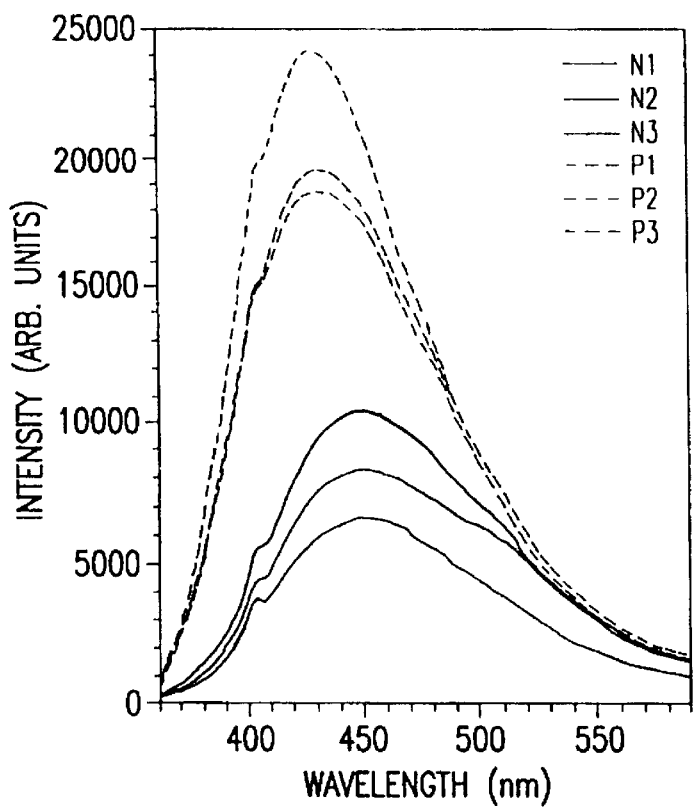
FIG. 16B illustrates the fluorescence spectrums of a group of HIV positive samples and a group of HIV negative samples.
Figure 16C:
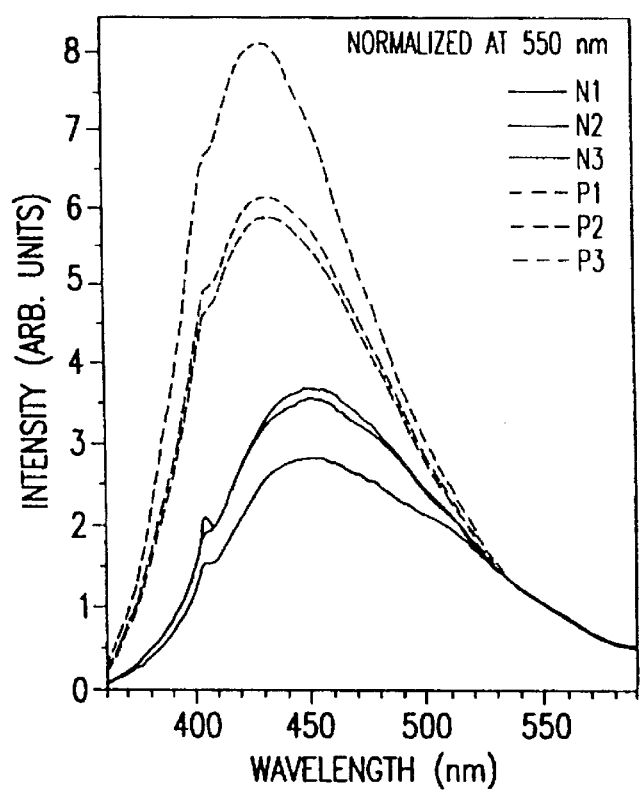
FIG. 16C illustrates the fluorescence spectrums of the HIV positive and HIV negative samples of FIG. 16B but normalized at 550 nm.
Figure 16D:
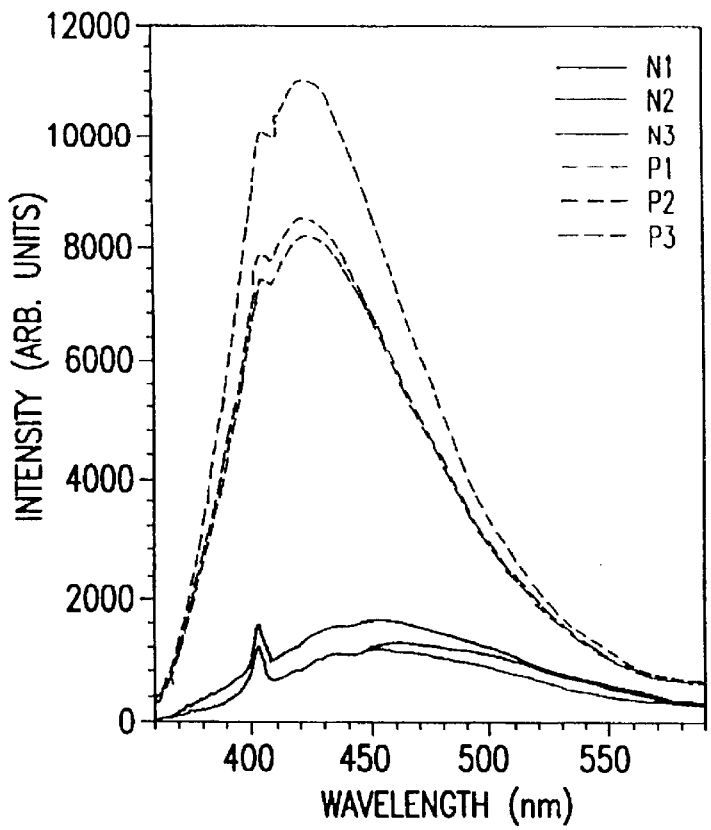
FIG. 16D illustrates the fluorescence spectrums of the HIV positive and HIV negative samples of FIG. 16B treated with CM-AGB.
Figure 16E:
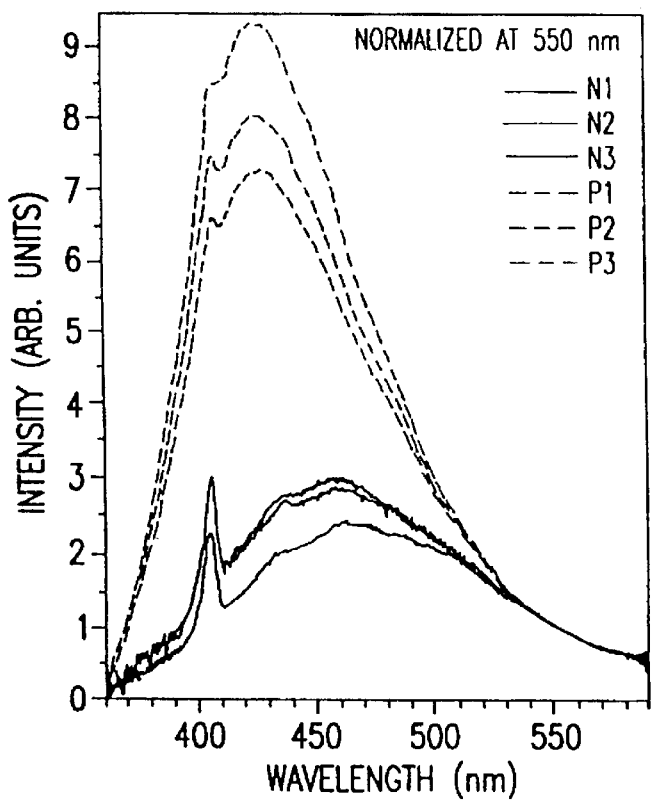
FIG. 16E illustrates the fluorescence spectrums of the CM-AGB treated HIV positive and HIV negative samples of FIG. 16D but normalized at 550 nm.

Referring to FIGS. 16A–D, applicants found that C-M (carboxy-methyl) Affi Gel Blue has a differential effect on HIV positive and negative plasmas. These results are obtained when specific ratios of plasma to C-M Affi Gel Blue are used. More specifically, in preparing CM-ABG treated samples, 0.25 milliliter (ml) of plasma is diluted to 2.0 ml with 20 mM of phosphate buffer and 1.5 ml of CM-AGB, which yields consistent and noticeable shifts in the spectra. For example, FIG. 16A shows the emission profiles of three HIV positive plasma samples (broken lines designated as P1, P2 and P3 sequentially from the top most broken line) and three HIV negative plasma samples (solid lines N1, N2 and N3 from the top most solid line), all of which are whole plasma samples as control samples and are untreated with CM-ABG. FIG. 16B shows the same emission profiles of these samples normalized at 550 nm. In comparison, referring to FIG. 16C, the emission profiles of CM-AGB treated HIV positive plasma samples (broken lines P1, P2 and P3) and that of CM-AGB treated HIV negative plasma samples (solid lines N1, N2 and N3) show much more differentiation between the HIV positive sample emission profiles and HIV negative sample emission profiles. Similarly, referring to FIG. 16D which show emission profiles of HIV positive samples treated with CM-AGB (broken lines P1, P2 and P3) and emission profiles of HIV negative samples (solid lines N1, N2 and N3), all normalized at 550 nm, the emission profiles for the CM-AGB treated samples normalized at 550 nm exhibit more differentiation between the emission profiles of the HIV positive samples and these of HIV negative samples, than that of the HIV positive and negative samples untreated with CM-AGB.

Figure 17A:
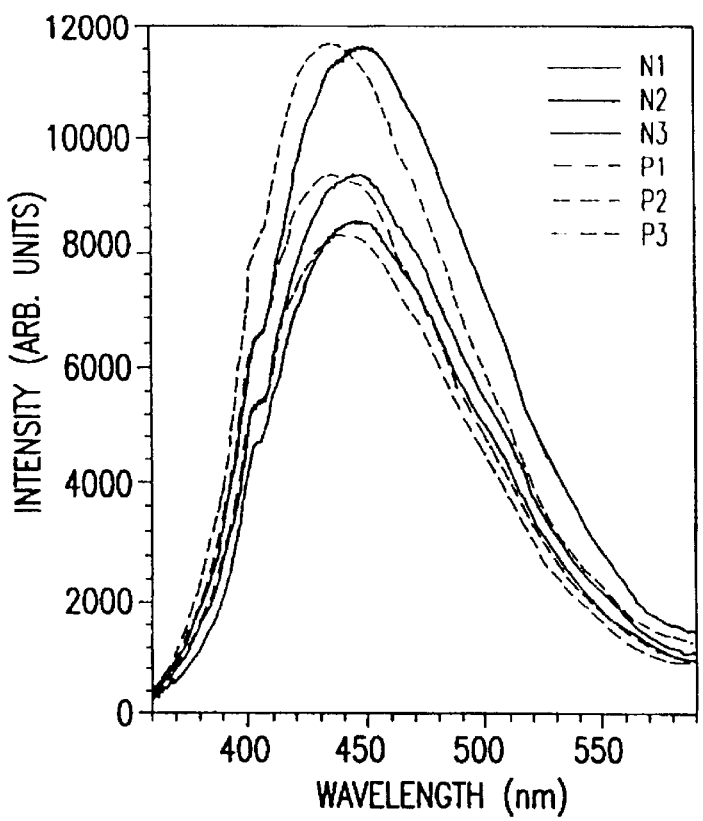
FIG. 17A illustrates the fluorescence spectrums of another group of HIV positive samples and another group of HIV negative samples.
Figure 17B:
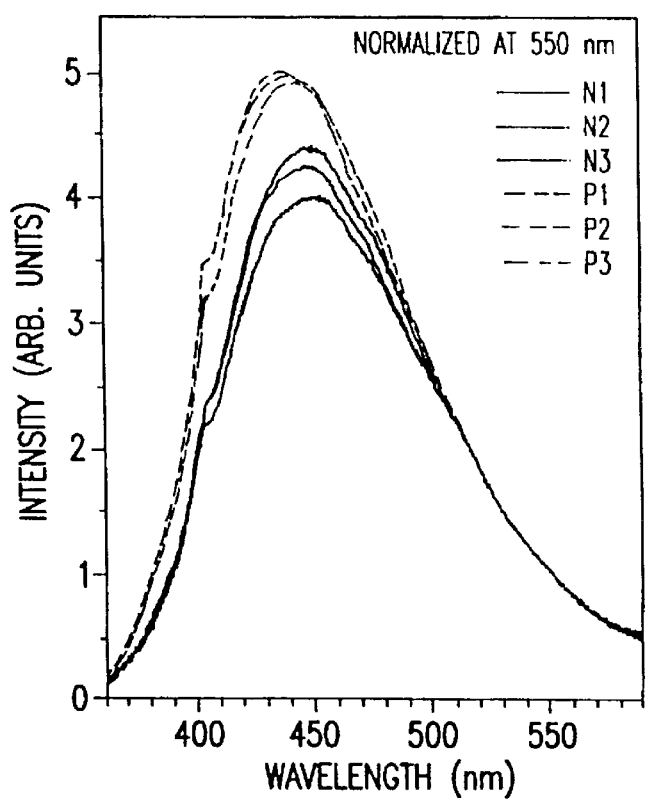
FIG. 17B illustrates the fluorescence spectrums of the HIV positive and HIV negative samples of FIG. 17A but normalized at 550 nm.
Figure 17C:
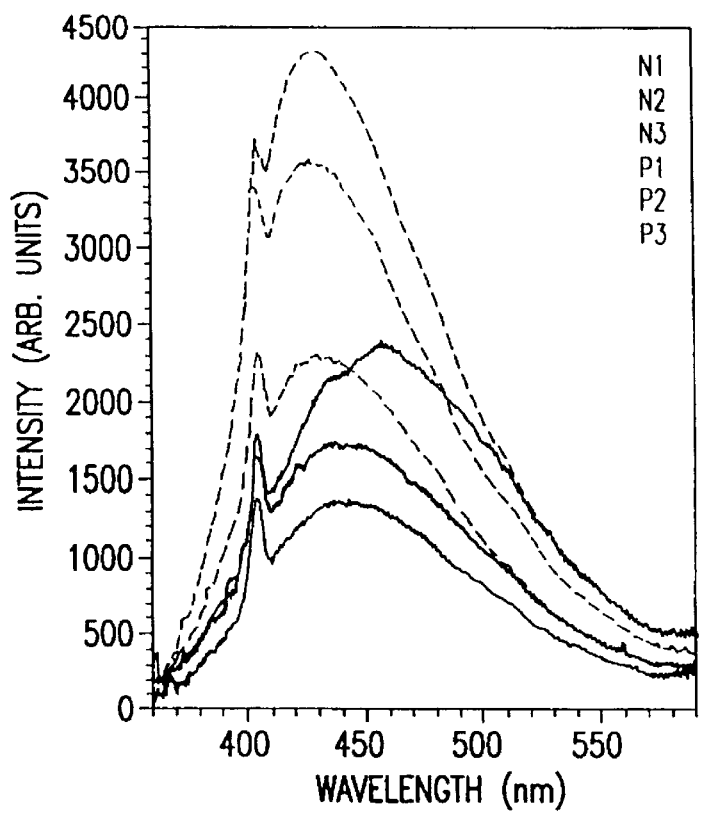
FIG. 17C illustrates the fluorescence spectrums of the HIV positive and HIV negative samples of FIG. 17A treated with CM-AGB.
Figure 17D:
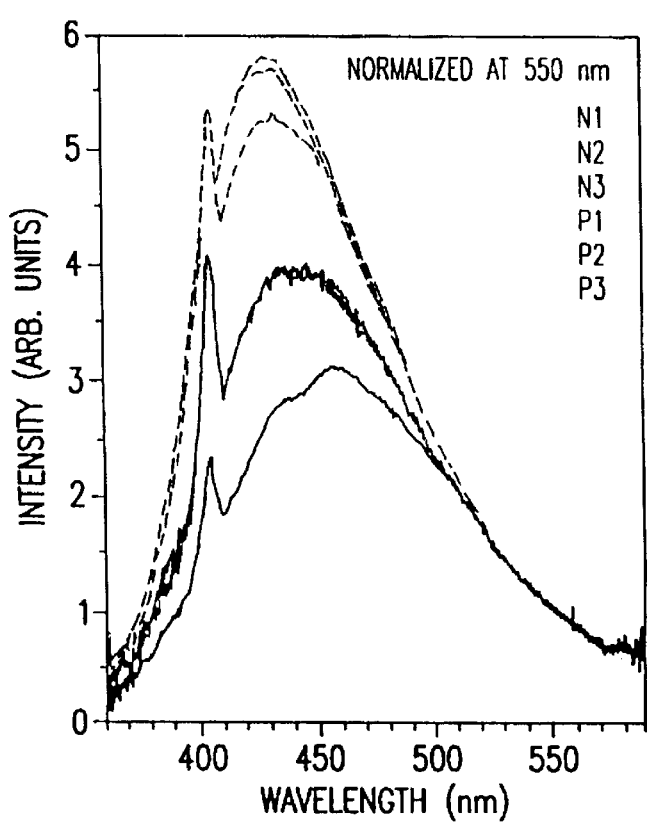
FIG. 17D is the fluorescence spectrums of the CM-AGB treated HIV positive and CM-AGB treated HIV negative samples of FIG. 17C but normalized at 550 nm.

FIGS. 17A–D show emission profiles of another set of six samples, three of which are HIV positive samples and the other three samples are HIV negative samples. FIG. 17A shows the emission profiles of the six samples untreated with CM-AGB (with the three broken lines P1, P2 and P3 for the HIV positive samples, and the three solid lines N1, N2 and N3 for the HIV negative samples). The emission profiles for the same untreated samples normalized at 550 nm are shown in FIG. 17B. The mission profiles for the same samples treated with CM-AGB are shown in FIG. 17C (with the three broken lines P1, P2 and P3 for the HIV positive samples, and three solid lines N1, N2 and N3 for the HIV negative samples). The emission profiles for the same CM-AGB treated samples normalized at 550 nm are shown in FIG. 17D, with the broken lines for the HIV positive samples and solid lines for the HIV negative samples. Again, the emission profiles obtained form the CM-AGB treated samples exhibit a much greater differentiation between the HIV positive and negative samples than that obtained from samples untreated with CM-AGB.

In summary, the differential effects of the CM-AGB on HIV positive and negative plasma suggest different plasma constituents have differential affinities for the CM-AGB gel and that these differences, as will be detailed below, are used as markers for HIV positive plasma.

In accordance with the present invention, a method is provided to treat the plasma samples before obtaining fluorescence emission spectrums from the samples so that the emission spectrums, and more particularly, certain characteristics of the emission spectrums, from the samples infected with an infectious disease (e.g., HIV viruses) are more differentiable from those samples not infected with such disease. In a preferred embodiment for detecting HIV viruses, the samples are prepared using the following procedures and assay conditions.

First, human plasma (0.75 ml) is diluted 1:8 with 20 mM potassium phosphate buffer, pH 7.3. The diluted plasma is then filtered through nylon syringe filters of 0.45 micron ($\mu$m) pore size to remove particulate (protein and free lipid aggregates). The filtered and diluted plasma is divided into three aliquots.

The first aliquot is left untreated and serves as a control sample, designated CT. The second aliquot is chromatographed, preferably using 1.5 ml of carboxymethyl Cibacron Blue (C-M Affi Gel Blue, Bio Rad Laboratories) and is designated AGB. The third aliquot is adsorbed with 0.2 ml of activated charcoal (NORIT A) and designated CH.

Each sample is then analyzed spectrofluorometrically using the system described above and illustrated in FIG. 1. In accordance with the present invention, spectrofluorimetry yields an emission spectra, the parameters of which is subsequently used to analyze each sample of plasma. To ensure the integrity and reproducibility of the emission spectra, applicants employed a beam compensation system which assures that all samples will be excited with identical levels of laser power. The circuit for this beam compensation system which operates to control the total laser power is illustrated in FIGS. 2A and 2B. The scan initiates laser power which increases over time. The shutter on the control device remains open until the power reaches a set point defined as $V_{ref}$ at which point the shutter closes. This enables the Infectious Disease LBS to control the total laser power used to excite the sample, yielding emission spectra which are internally compensated for input power.

In accordance with the present invention, the analysis of a given sample's emission profile is performed using the parameters defined as follows and the algorithm described in detail below. The definitions of the parameters used in the algorithm are as follows:

$\lambda_p$: The wavelength in nanometers at which the peak of fluorescence intensity is obtained. Mathematically, this is when dY/dX=0, where Y is the intensity of fluorescence and X is wavelength of the fluorescence. For example, $\lambda_{p\text{-}CT}$ is the peak wavelength of a control sample.

Am: The amplitude of the peak fluorescence. For example, $Am_{CT}$ corresponds to the amplitude of a control sample.

Figure 18:
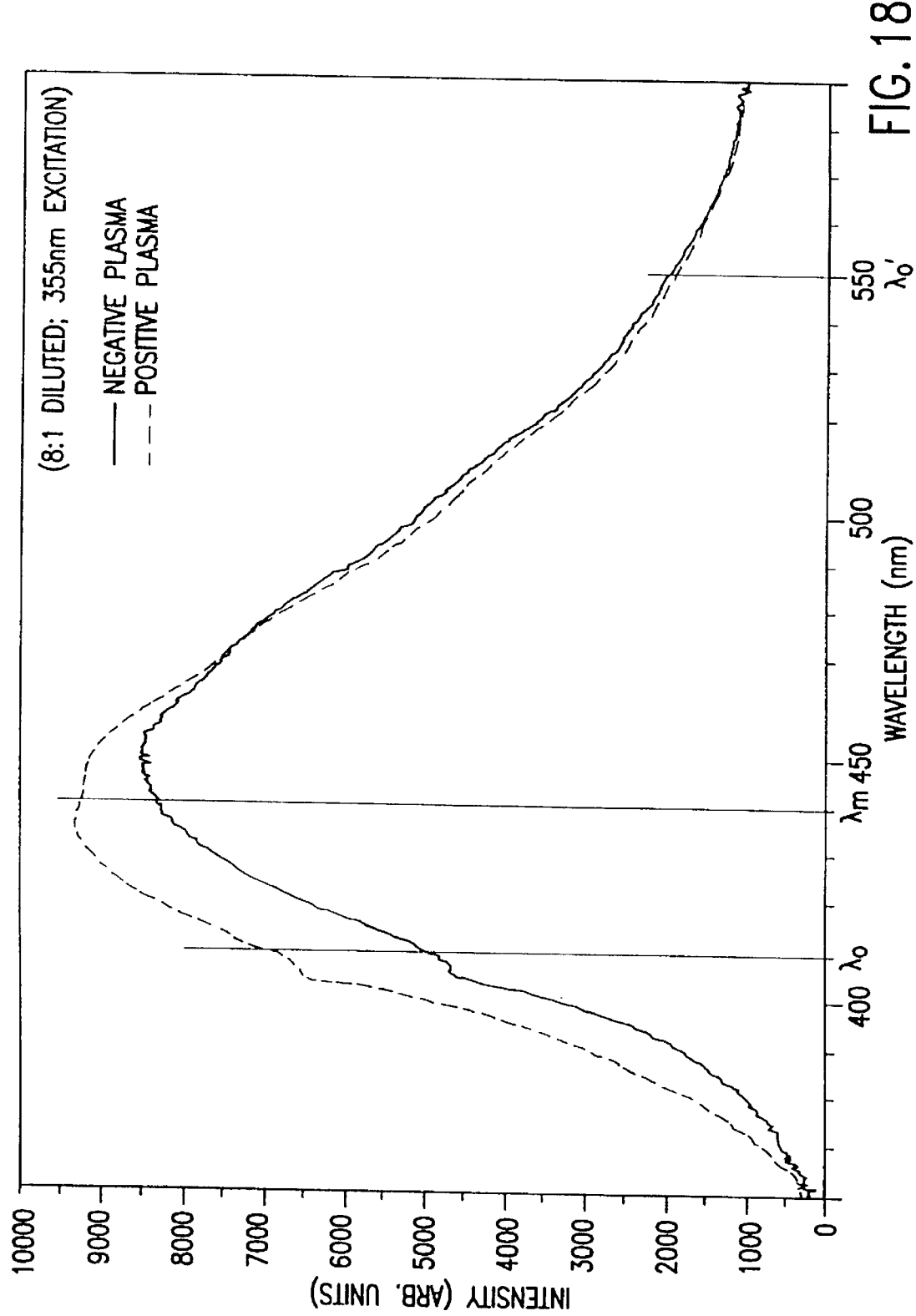
FIG. 18 illustrates the fluorescence spectrums of an HIV positive plasma and an HIV negative plasma samples for demonstrating the definition of an "area ratio" parameter.

Ar: The area ratio. The area ratio is defined as, as depicted in FIG. 18, the area under the emission spectrum extending from a first selected wavelength ($\lambda_0$) to a second selected wavelength ($\lambda_m$), divided by the area under the curve extending the second selected wavelength to a third selected wavelength point($\lambda_0'$). Mathematically this will be calculated as $[\int_{\lambda_0}^{\lambda_m}/\int_{\lambda_m}^{\lambda_0'}]$. In the preferred embodiment as depicted in FIG. 18, 410 nm, 440 nm and 550 nm are selected as the first, second and third selected wavelengths, respectively. They are also used in all of the area ratio data shown herein. It should be understood that different wavelengths may be used, which may be adapted to obtain the same results as described herein.

Figure 19:
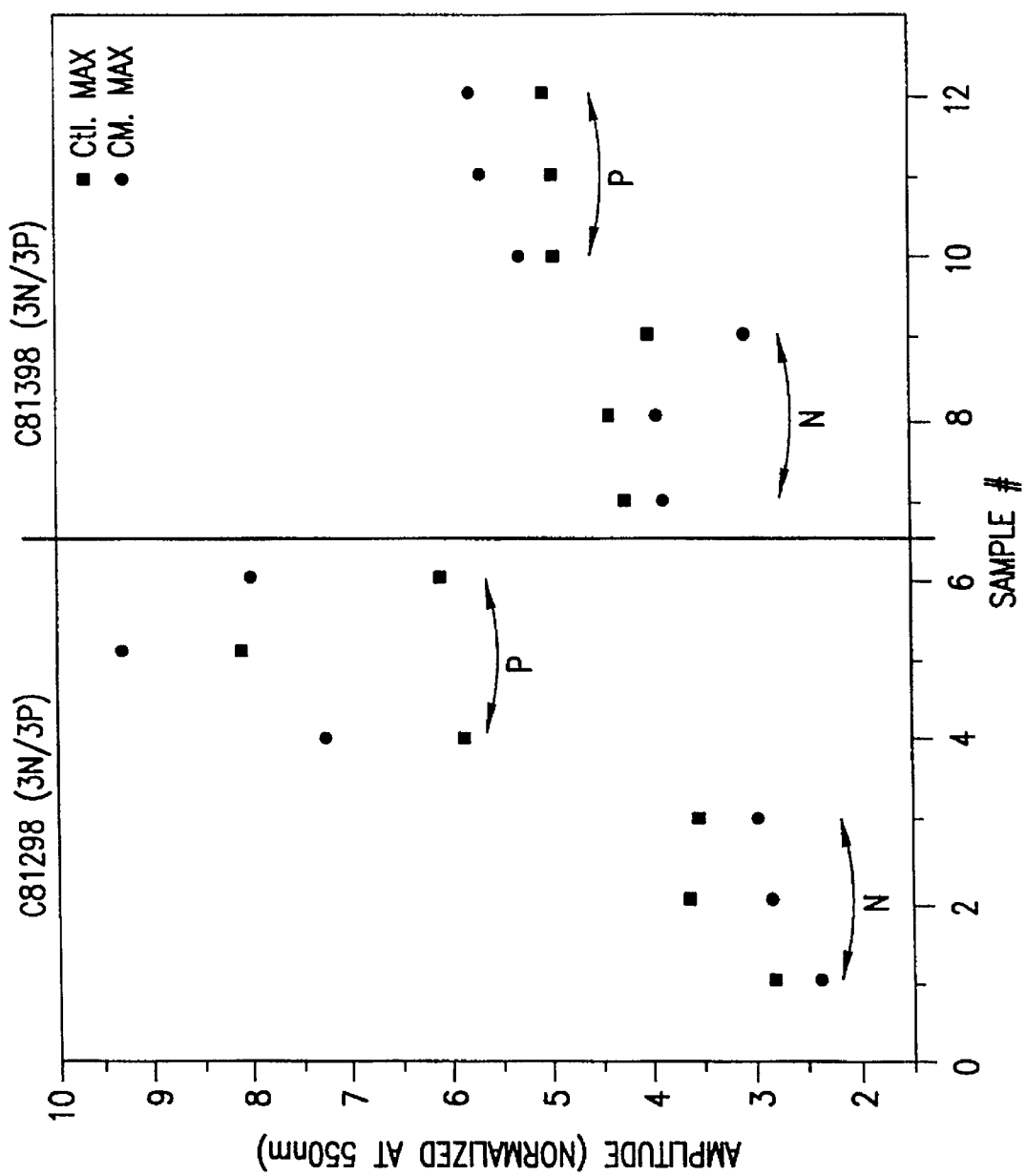
FIG. 19 shows emission peak amplitudes of a group of HIV positive and negative samples normalized at 550 nm with and without CM-AGB treatment.

In accordance with the present invention, one or more of these parameters are used to discriminate samples infected with an infectious disease, such as HIV positive samples, from non-infected samples, such as HIV negative samples. For example, referring to FIG. 19, the amplitude, Am, is used to differentiate the HIV positive samples from the HIV negative samples. In FIG. 19, the x-axis corresponds to the sample number, and the y-axis corresponds to the amplitude, Am, of the samples normalized at 550 nm. For each sample, two measurements of the amplitude are performed and shown in the FIG., one for the untreated sample (i.e., control sample) which is shown as a back square in the FIG., the other for the sample treated with CM-AGB which is shown as a black circle in the FIG. The measurements results designated "N" are obtained from known HIV negative samples, which are determined by commercially available, FDA-approved tests. The measurement results designated "P" are obtained from known HIV positive samples, which are determined by commercially available, FDA-approved tests. As shown in this FIG., sample Nos. 1, 2, 3, 7, 8 and 9 are known HIV negative samples, whereas sample Nos. 4, 5, 6, 10, 11 and 12 are known HIV positive samples.

On the basis of the amplitude measurement results shown in FIG. 19, it is seen that the HIV negative samples and HIV positive samples can be discriminated on the basis of their amplitudes, particularly the amplitudes (indicated as black circles in the FIG.) of the CM-AGB treated samples. For example, if a normalized amplitude value of 5 is used to discriminate the samples treated with CM-AGB (that is, the samples having an amplitude above 5 are deemed to be HIV positive whereas the samples having a normalized amplitude less than 5 are deemed to be HIV negative), it is seen that the six HIV positive samples among the 12 samples tested will be correctly discriminated from the six HIV negative samples. It is noted that the CM-AGB treatment of the samples improves the discrimination of the infected samples from the uninfected samples.

Figure 20:
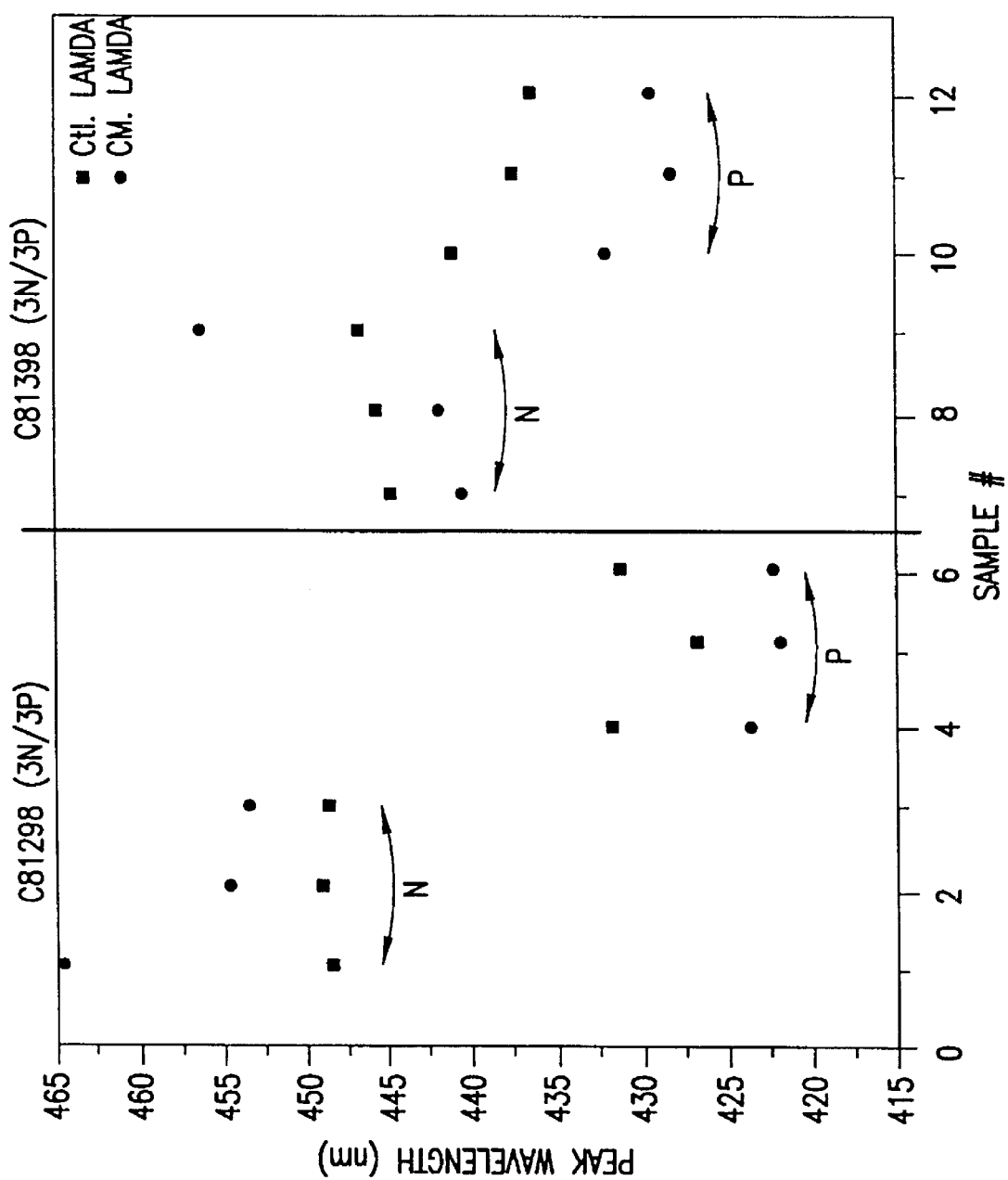
FIG. 20 shows the emission peak wavelengths of the same HIV positive and negative samples of FIG. 19 with and without CM-AGB treatment.

In accordance with the present invention, peak wavelength, $\lambda_p$, is used to discriminate infected samples, such as HIV positive samples, from uninfected samples, such as HIV negative samples. Referring to FIG. 20, which are the peak wavelength measurement results of the same set of samples that are used to obtain the amplitude measurements shown in FIG. 19, and which has the same designations, if a peak wavelength of 435 nm is used to discriminate the CM-AGB treated HIV positive samples from the CM-AGB treated HIV negative samples, it is seen that the six HIV positive samples among the 12 samples tested will be correctly discriminated from the six HIV negative samples. It is also noted that the CM-AGB treatment of the samples improves the discrimination of the infected samples from the uninfected samples for peak wavelength measurement.

Figure 21:
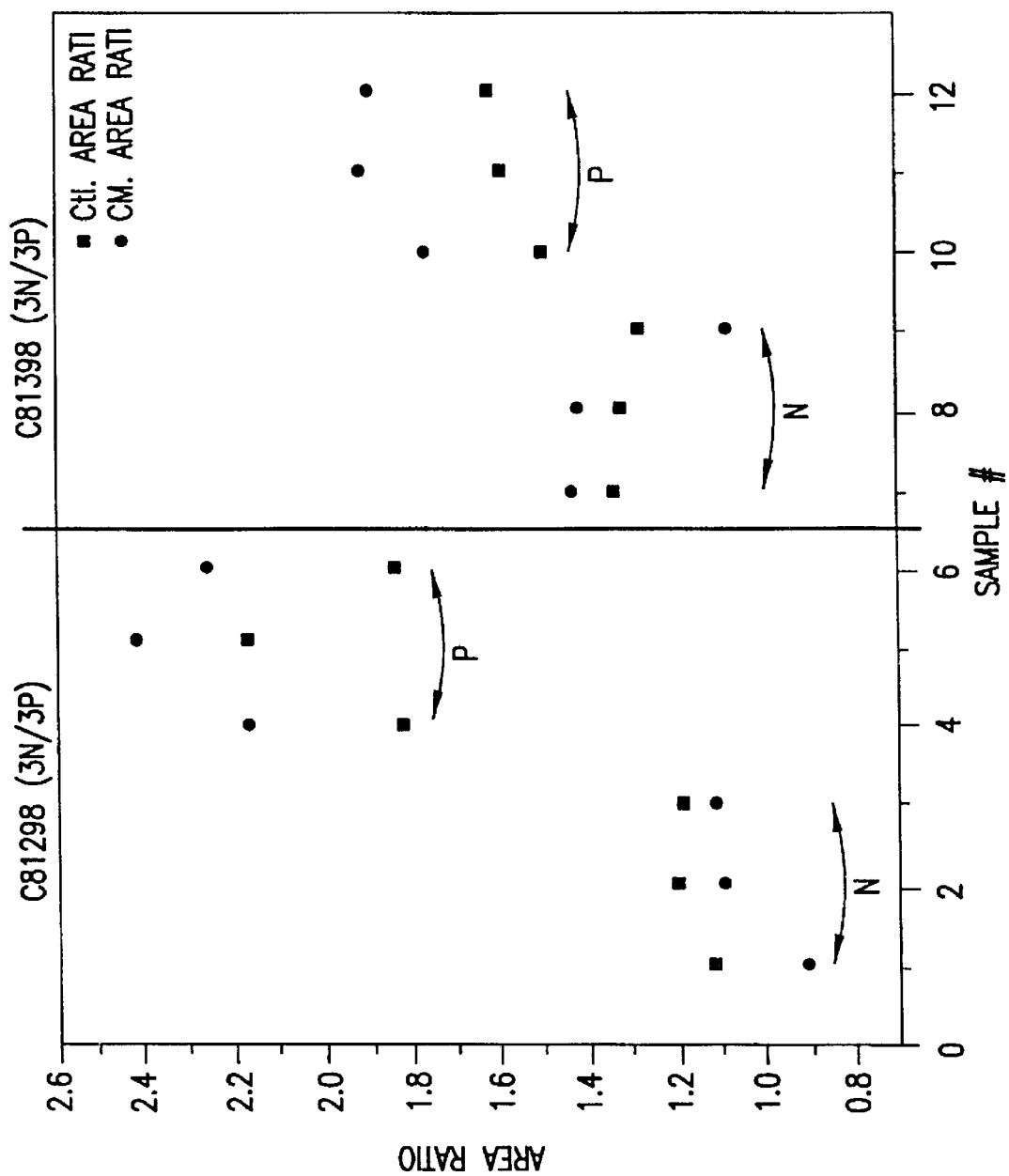
FIG. 21 shows the area ratios of the same HIV positive and negative samples of FIG. 19 with and without CM-AGB treatment.

In accordance with the present invention, area ratio, Ar, is used to discriminate infected samples, such as HIV positive samples, from uninfected samples, such as HIV negative samples. Referring to FIG. 21, which are the area ratio measurement results of the same set of samples that are used to obtain the amplitude measurements shown in FIG. 19, an area ratio of 1.6 is used to discriminate the CM-AGB treated HIV positive samples from the CM-AGB treated HIV negative samples, the six HIV positive samples among the 12 samples tested will be correctly discriminated from the six HIV negative samples. It is clear from the test results that the CM-AGB treatment of the samples improves the discrimination of the infected samples from the uninfected samples.

Figure 22:
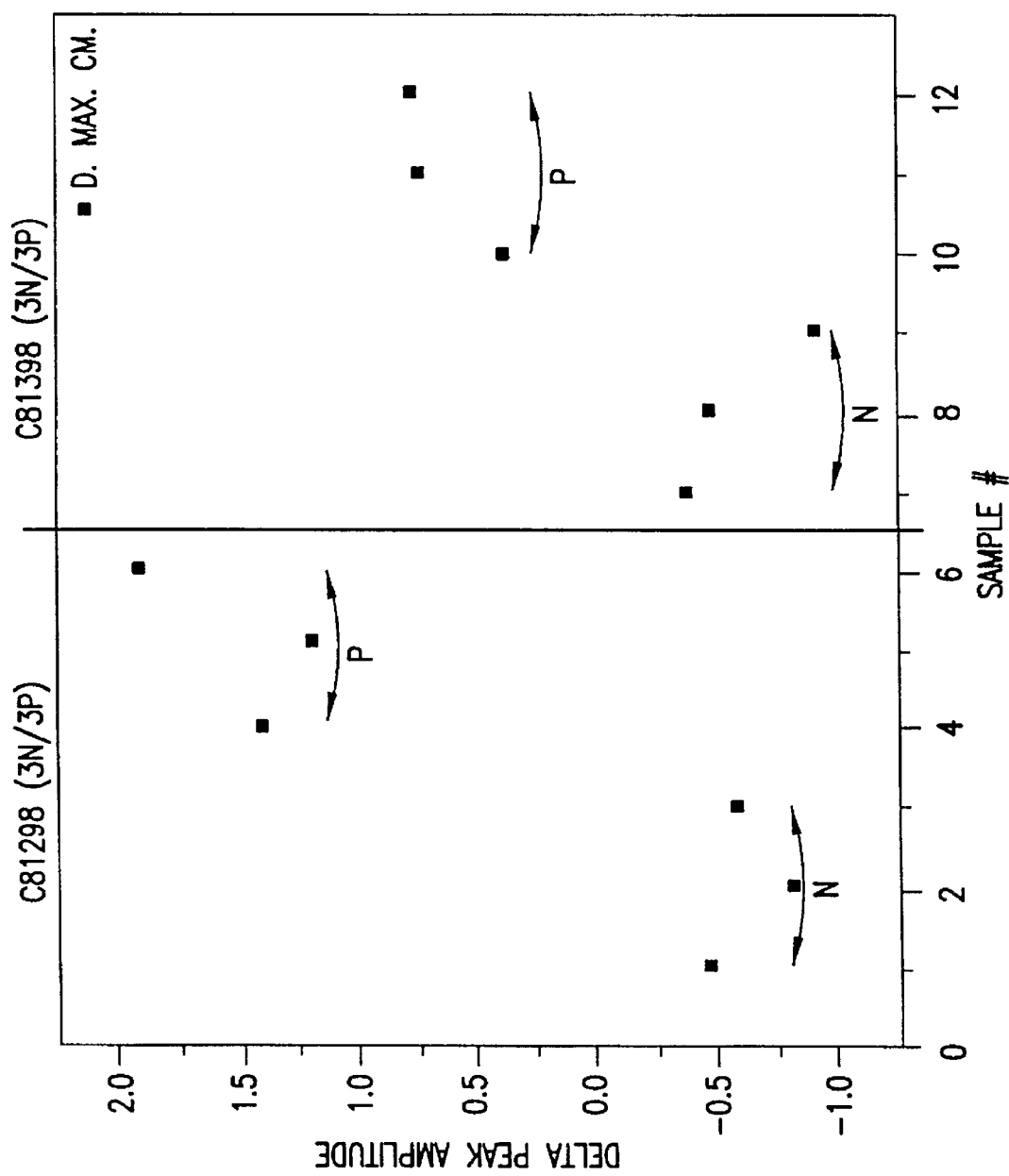
FIG. 22 shows amplitude changes of the same HIV positive and negative samples of FIG. 19 after the CM-AGB treatment.

In accordance with the present invention, changes of the amplitudes of samples, $\Delta Am$, before and after CM-AGB treatment, are used to discriminate infected samples, such as HIV positive samples, from uninfected samples, such as HIV negative samples. Referring to FIG. 22, which shows the amplitude changes for the same set of samples that shown in FIG. 19, if no change of amplitude (i.e., $\Delta Am=0.0$) is used to discriminate the HIV positive samples from the HIV negative samples, it is seen that the six HIV positive samples among the 12 samples tested will be correctly discriminated from the six HIV negative samples.

Figure 23:
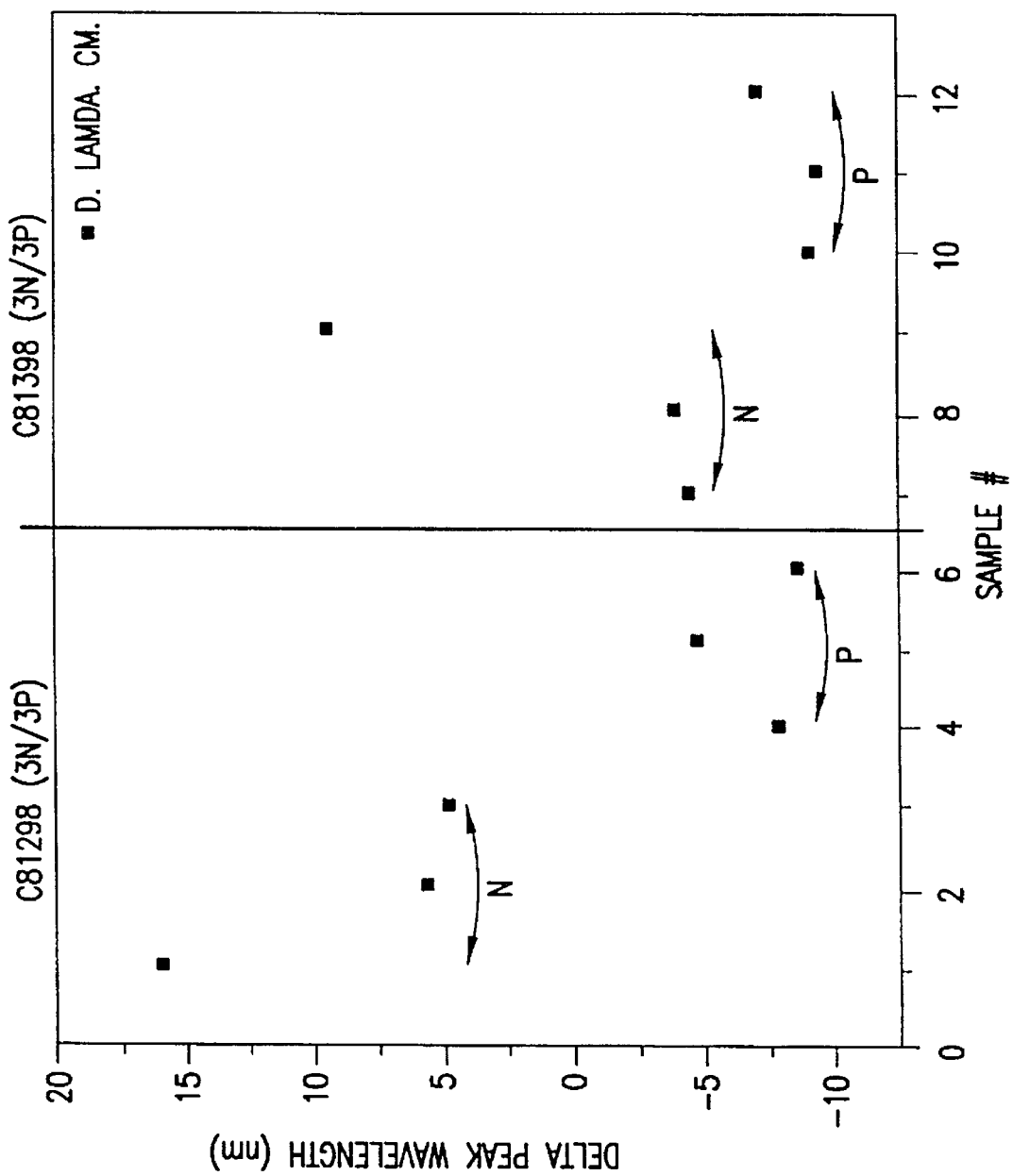
FIG. 23 shows wavelength changes of the same HIV positive and negative samples of FIG. 19 after the CM-AGB treatment.

In accordance with the present invention, changes of the peak wavelengths of samples, $\Delta \lambda_p$, before and after CM-AGB treatment, are used to discriminate infected samples, such as HIV positive samples, from uninfected samples, such as HIV negative samples. Referring to FIG. 23, which shows the amplitude changes for the same set of samples in FIG. 19, if no change of peak wavelength (i.e., $\Delta \lambda_p=0.0$ nm) is used to discriminate the HIV positive samples from the HIV negative samples, it is seen that HIV positive sample Nos. 4, 5, 6, 10, 11 and 12 will be discriminated from HIV negative sample Nos. 1, 2, 3 and 9. However, HIV negative sample Nos. 7 and 8 will not be discriminated from the HIV positive samples.

Figure 24:
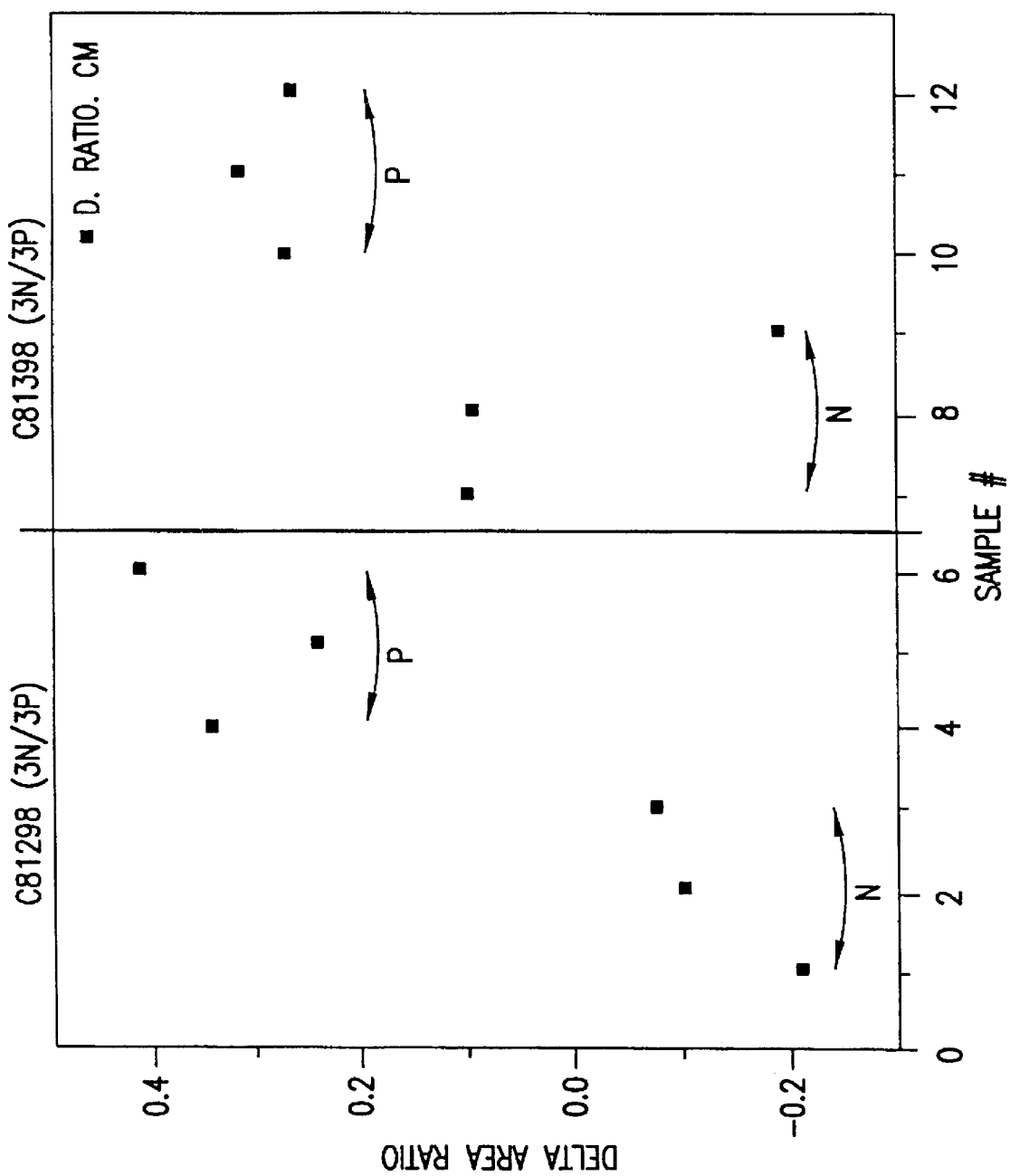
FIG. 24 shows area ratio changes of the HIV positive and negative samples after the CM-AGB treatment.

In accordance with the present invention, changes of area ratios of the of samples, $\Delta Am$, before and after CM-AGB treatment, are used to discriminate infected samples, such as HIV positive samples, from uninfected samples, such as HIV negative samples. Referring to FIG. 24, which shows the area ratio changes for the same set of samples in FIG. 19, if no change of area ratio (i.e., $\Delta Ar=0.0$) is used to discriminate the HIV positive samples from the HIV negative samples, HIV positive sample Nos. 4, 5, 6, 10, 11 and 12 will be discriminated from HIV negative sample Nos. 1, 2, 3 and 9, but HIV negative sample Nos. 7 and 8 will not be discriminated from the HIV positive samples. However, if a change of area ratio of 0.2 (i.e., $\Delta Ar=0.2$) used, all of the HIV positive samples will be discriminated from the HIV negative samples.

In accordance with the present invention, although one of the above-mentioned parameters by itself may not be able to discriminate infected samples from uninfected samples with one hundred percent accuracy, if more than one of the parameters are used, high accuracy may nevertheless be achieved. In addition, proper algorithms using one or more of the above described parameters may be used to discriminate infected samples from non-infected samples.

In accordance with the present invention, various discriminators are provided for discriminating infected samples from non-infected samples.

In a preferred embodiment, a discriminator D1 is constructed from $1/\lambda_p$, Am and Ar, all three of which will be greater for positive samples than negative samples or the mean value from a normal data base. Thus, any additive or multiplicative combination of these parameters from positive samples divided by an identical combination of these parameters from the normal data base will be greater than 1. The value will be closer to 1 or less than 1 for negative samples. Such an analytic function for D1 is expressed as $D1=f(1/\lambda_p, Am, Ar)$.

Another discriminator D2 is provided, which takes advantage of the differential shifts in these parameters ($1/\lambda_p$, Am, Ar) after the sample undergoes chromatography through CM-Affi Gel Blue. After chromatography, $\Delta \lambda_p$ is greater for HIV positive samples than for HIV negative (normal) samples. Because $\Delta Am$ is greater for HIV negative samples than for HIV positive samples, the reciprocal of the difference in Am, $1/\Delta Am$, is greater for positive samples. The parameter $\Delta Ar$ is greater for positive samples. Thus, any additive or multiplicative combination of these parameters from positive samples divided by an identical combination of these parameters from the normal data base will again be greater than 1. This ratio for negative samples will be closer 1 or less than 1. Such an analytic function for D2 is expressed as $D2=f(\Delta \lambda_p, \Delta 1/Am, \Delta Ar)$.

Another discriminator D3 is provided, which will reflect the differential effects of adsorption by charcoal. The parameter $1/\Delta \lambda_p$ will be greater for HIV negative samples than for HIV positive samples, so will be the parameter $1/\Delta Ar$. Thus, any additive or multiplicative combination of these parameters divided by the same combination from the normal data base will be greater than 1 for positive samples and closer to 1 or less than 1 for HIV negative samples. Such an analytic function for D3 is described by $D3=f(\Delta \lambda_p, 1/\Delta Ar)$.

In accordance with the present invention, an aggregate discriminator $D^*=f(iD1, jD2, \ldots, kD3)$ is provided, which will yield values for HIV positive samples greater than for HIV negative samples. The coefficients i through k are weighing factors to be determined empirically. HIV Negative samples will yield a range of $D^*$s, the variance of which within the data base for the normal samples (i.e., HIV negative samples) must be determined. This will be determined from large scale testing by the Infectious Disease LBS of the present invention.

Figure 25:
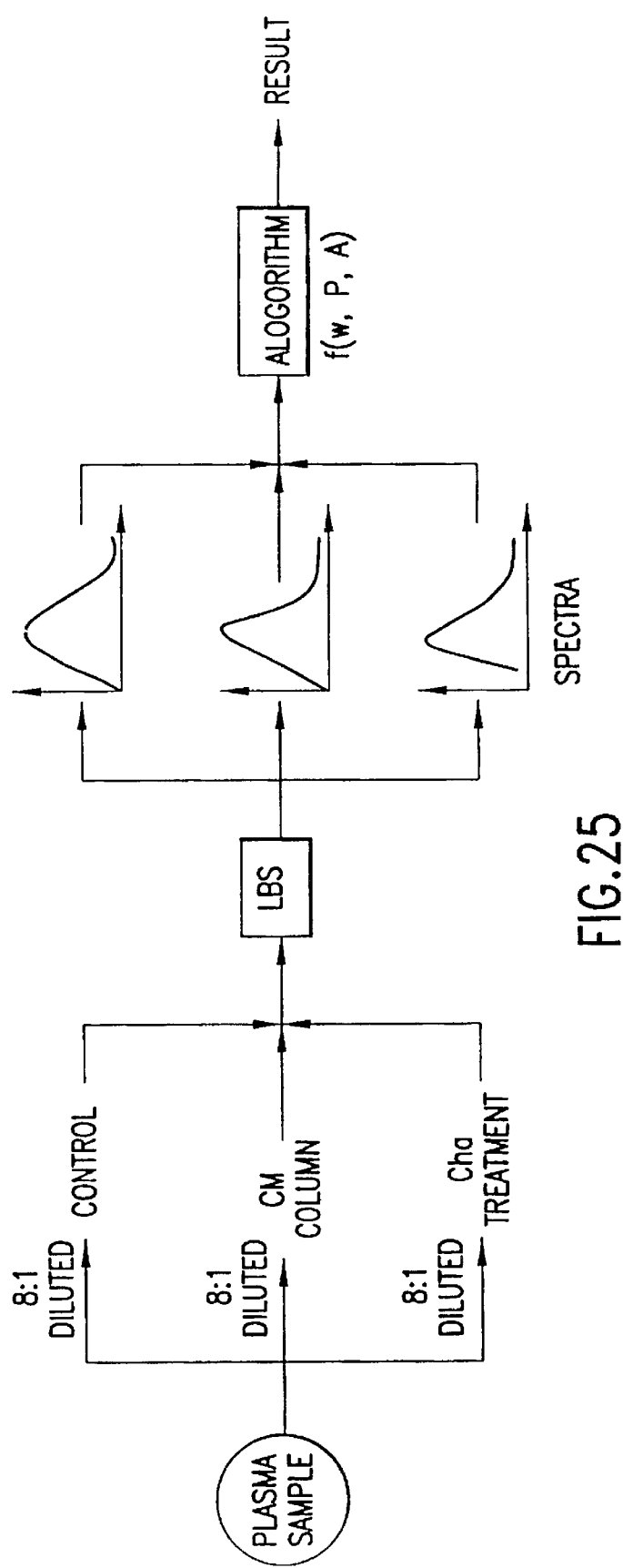
FIG. 25 illustrates a process flow chart according to the present invention.

FIG. 25 illustrates a flow diagram of the infectious disease detection method of the present invention. A plasma blood sample to be tested is first divided into three portions: The first portion is diluted 1:8 with potassium phosphate buffer and will be used as a control sample (referred in the FIG. as "control"); the second portion is also diluted 1:8 with potassium phosphate buffer and then chromatographed through CM-AGB (referred in the FIG. as "CM Column"); and the third portion is treated with activated charcoal (referred in the FIG. as "Cha Treatment"). After that, all three portions are provided to the LBS of the present invention to obtain their fluorospectrum in the desired wavelength band with excitation at a desired wavelength. Their fluorospectrum and characteristics and/or parameters are then used in an algorithm for calculation, which provides a final indicator as to whether or not the sample is infected with certain infectious diseases.

Figure 26A:
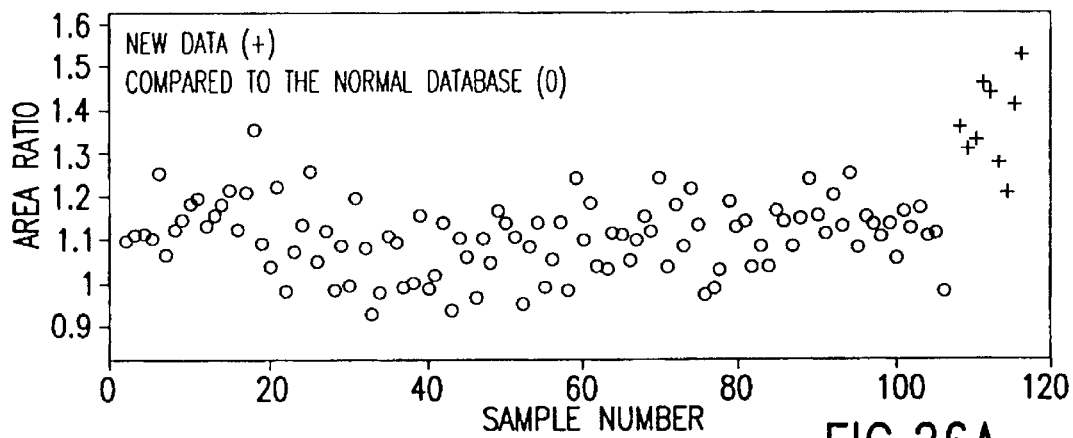
FIGS. 26A–C show early detection of HIV infection of untreated samples as compared with control samples.
Figure 26B:
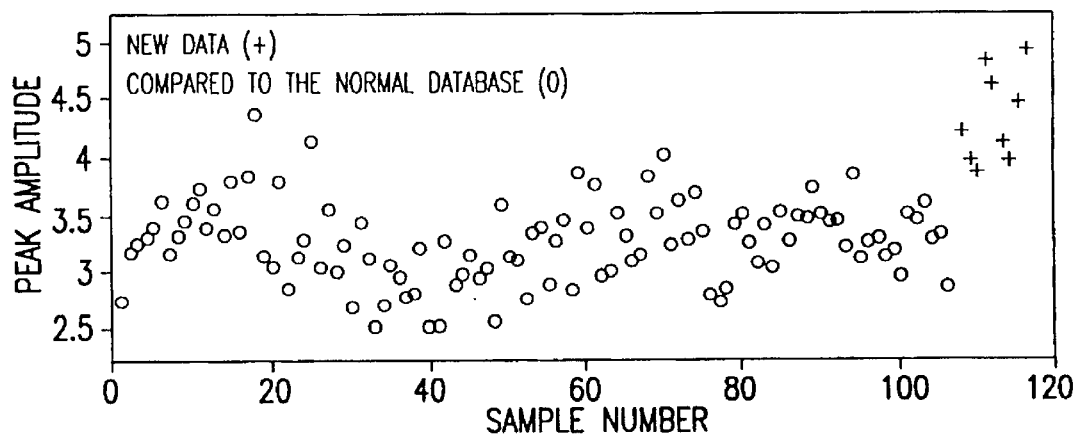
Figure 26C:
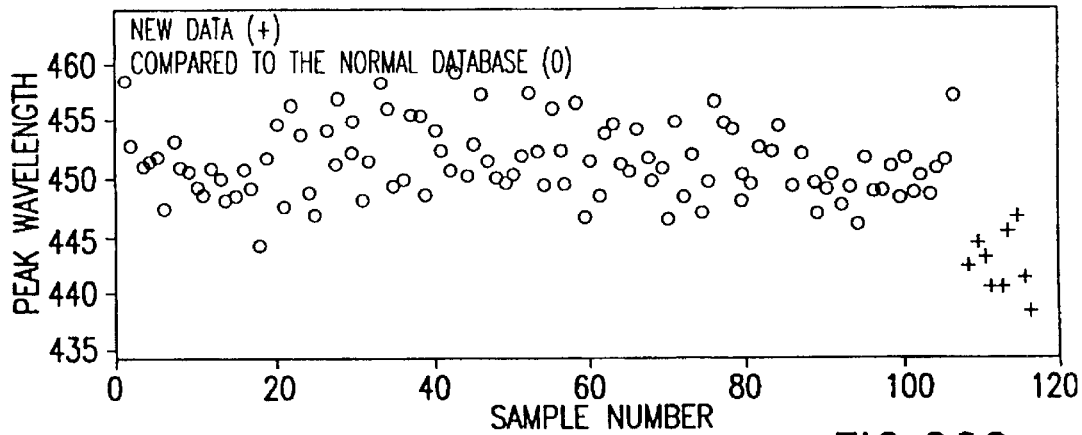

The method and apparatus for infectious disease detection of the present invention may be used to detect HIV infection at a very early stage where it is still not detectable by the widely used enzyme-linked immunosorbent assay method ("the ELISA method") or conventional clinical diagnosis. FIGS. 26A–C show the measurement results of the area ratio, peak amplitude, and peak wavelength, of the normal database (represented as "o" in the FIG.), respectively, and those of blood samples, untreated with CM-AGB or charcoal, (i.e., control samples) from a single individual at difference times at an early stage of HIV infection (represented as "+" in the FIG.). There are nine samples taken from the same individual and tested and their test results are arranged in the FIG. such that the left-most result is from the blood plasma sample first taken in time, and the right-most result from the blood plasma sample last taken in time, and the results in-between are arranged sequentially from the earlier-taken samples to the later-taken samples. As shown in FIGS. 26A–C, the test results of the blood samples from the HIV infected individual are fairly discriminated from those of the normal database.

Figure 27A:
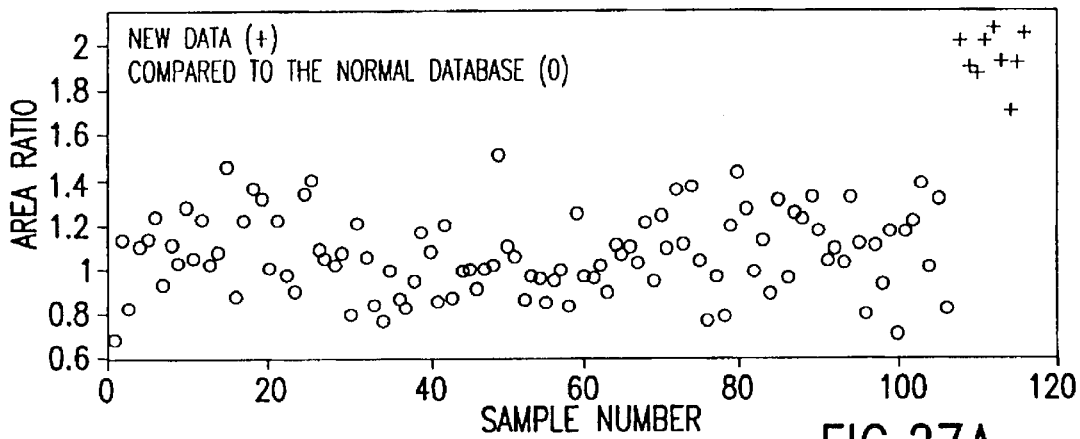
FIGS. 27A–C show early detection of HIV infection using the same samples of FIGS. 26A–C after CM-AGB treatment as compared with control samples.
Figure 27B:
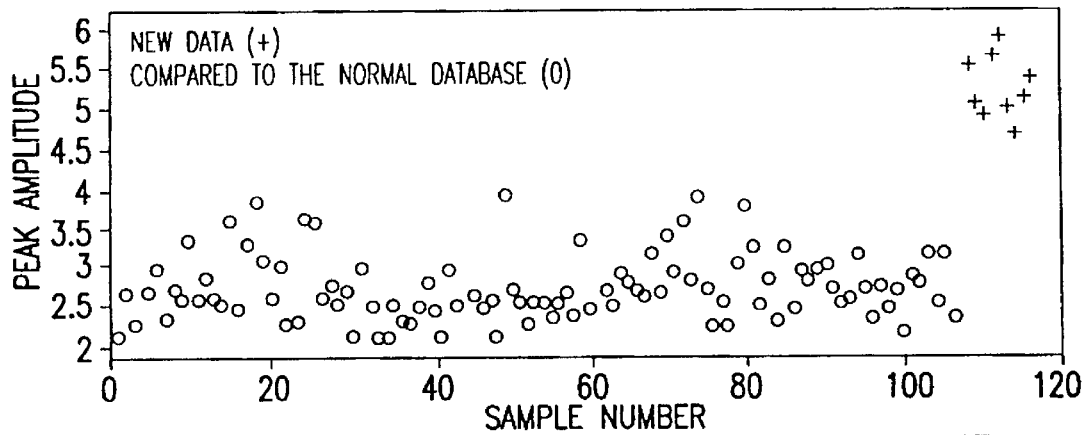
Figure 27C:
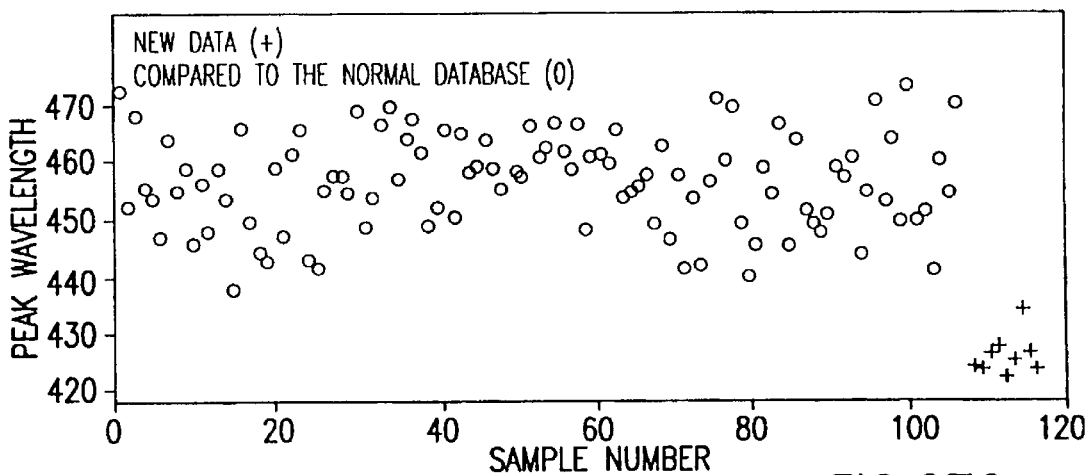

FIGS. 27A–C are the measurement of the same parameters for the same samples after the samples are treated with CM-AGB. As shown, the discrimination between the results of the infected samples and those of the normal database is even more evident than the measurement on the untreated samples; the infected samples are clearly discriminated from the normal database. FIG. 28 is a table listing the sample numbers, the relative time when the samples are taken, and their ELISA method test results, and conventional clinical diagnosis test results. For the first four samples, both the ELISA method and conventional clinical diagnosis fail to detect the HIV viruses. In comparison, as shown in FIGS. 26A–C and 27A–C, these four samples are discriminated from the normal database by using the method and apparatus of the present invention. Accordingly, the infectious disease detection method and apparatus of the present invention provide earlier detection of infection, such as HIV infection, when it is yet to be detectable by conventional detection means.

Figure 29:
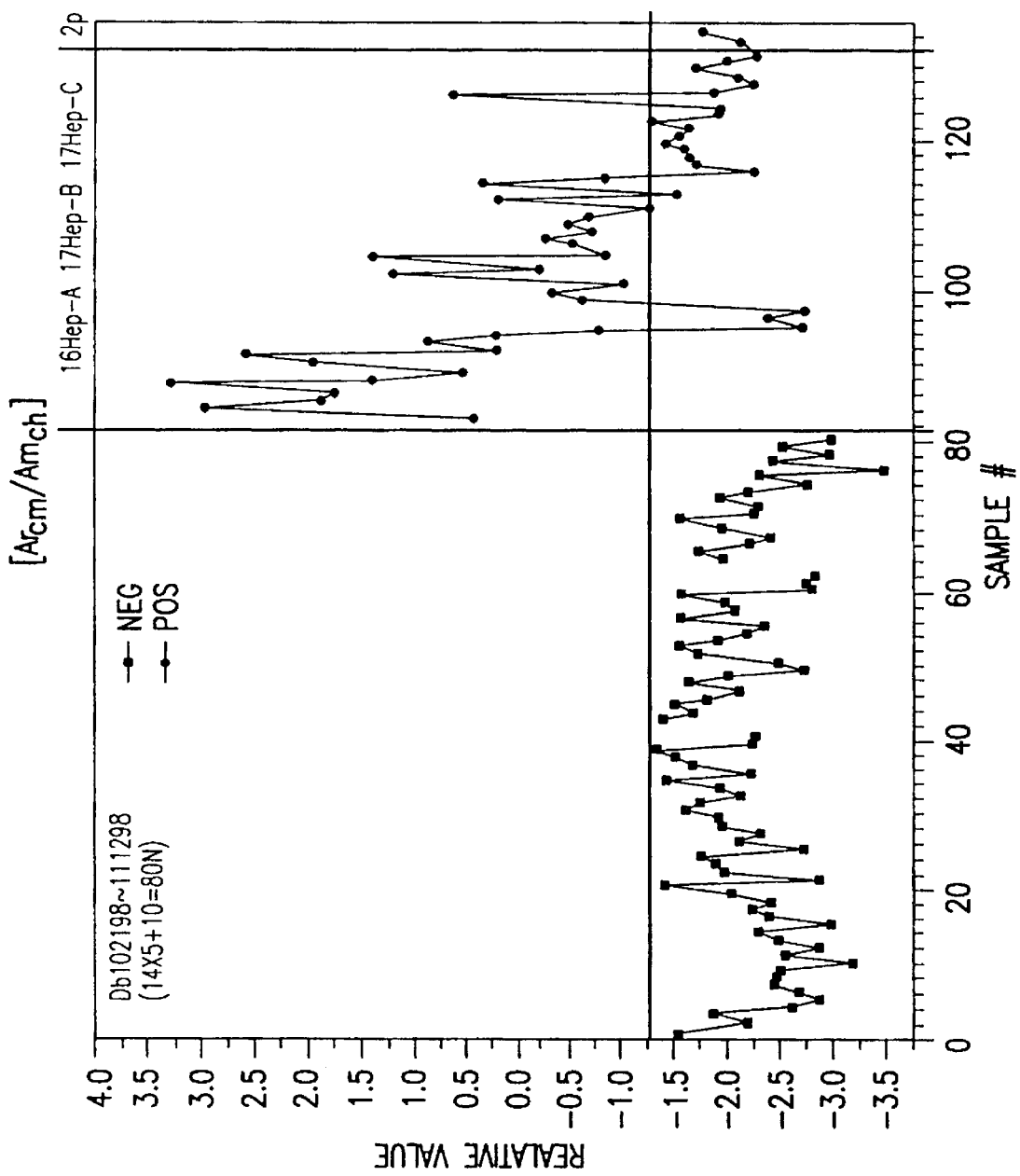
FIG. 29 shows the emission peak amplitude differences of Hepatitis infected samples between the samples treated with CM-AGB and the same samples treated with activated charcoal and their comparison to those of non-Hepatitis infected control samples.

In accordance with the present invention, the infectious disease detection method and apparatus of the present invention are used to discriminate Hepatitis A, B, and C. Referring to FIG. 29, the x-axis is the sample number and the y-axis is $(Am_{BL}-Am_{CH})$, where $Am_{BL}$ is the peak amplitude of the emission spectrum for the AGB-treated sample and $Am_{CH}$ is the peak amplitude of the emission spectrum for the charcoal-treated samples. Sample Nos. 1–80 are samples from the normal database (i.e., Hepatitis negative samples). Sample Nos. 81–100 are samples known to be Hepatitis A positive. Sample Nos. 101–120 are samples known to be Hepatitis B positive. Sample Nos. 121–127 are samples known to be hepatitis C positive. As shown by this FIG., the parameter $(Am_{BL}-Am_{CH})$ is a good discriminator between normal samples and hepatitis A or B positive samples. In addition, this parameter is also a discriminator, although not one hundred percent accurate, between Hepatitis A samples and Hepatitis C samples.

Figure 30:
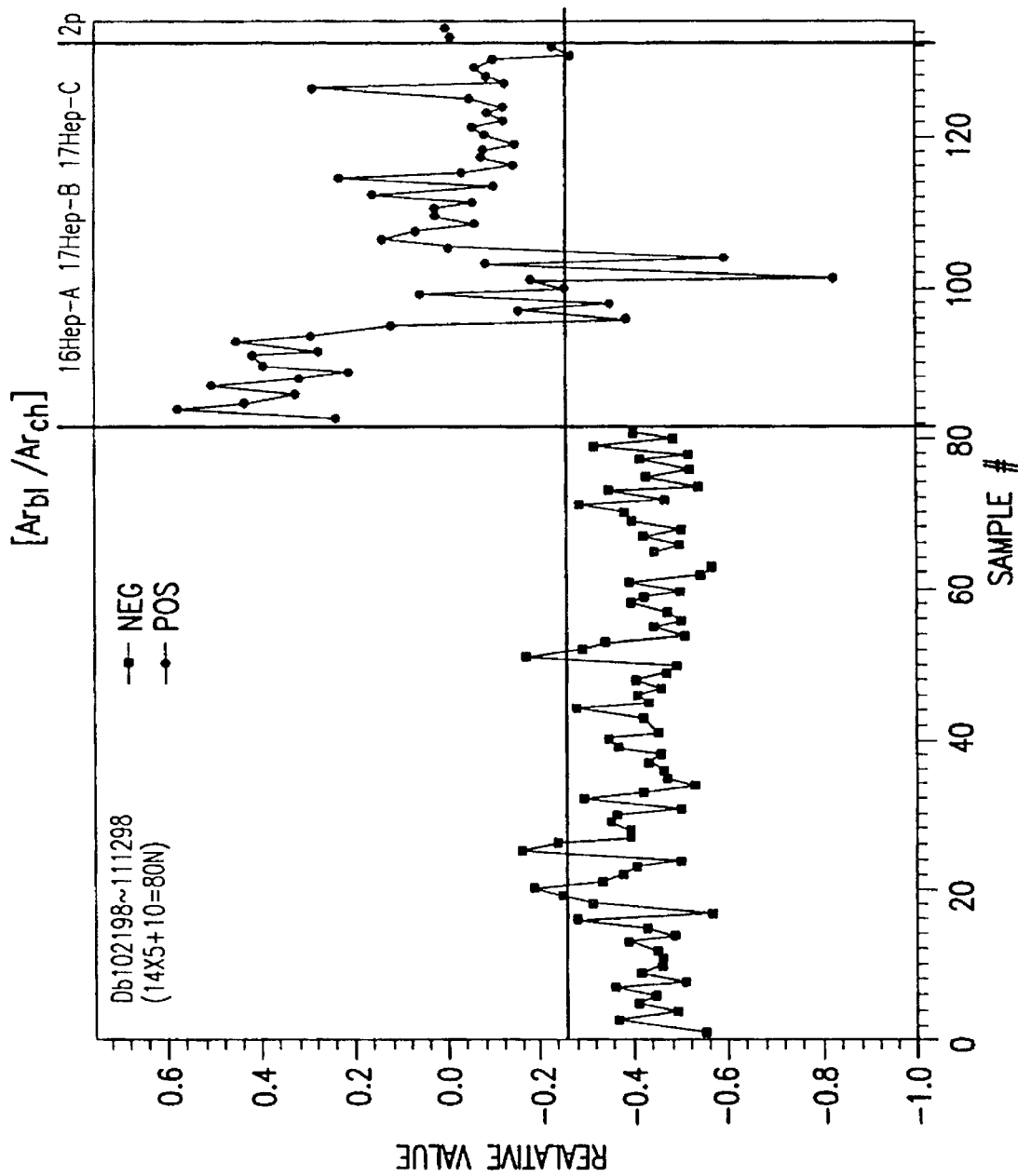
FIG. 30 shows the area ratio differences of the same Hepatitis infected samples of FIG. 29 between the samples treated with CM-AGB and the same samples treated with activated charcoal and their comparison to those of non-Hepatitis infected control samples.

FIG. 30 shows the parameter $(Ar_{BL}-Ar_{CH})$, i.e., area ratio difference between AGB-treated and charcoal-treated samples, for the same set of samples of FIG. 29. It is shown that this parameter discriminates Hepatitis A and hepatitis C from normal samples.

Figure 31:
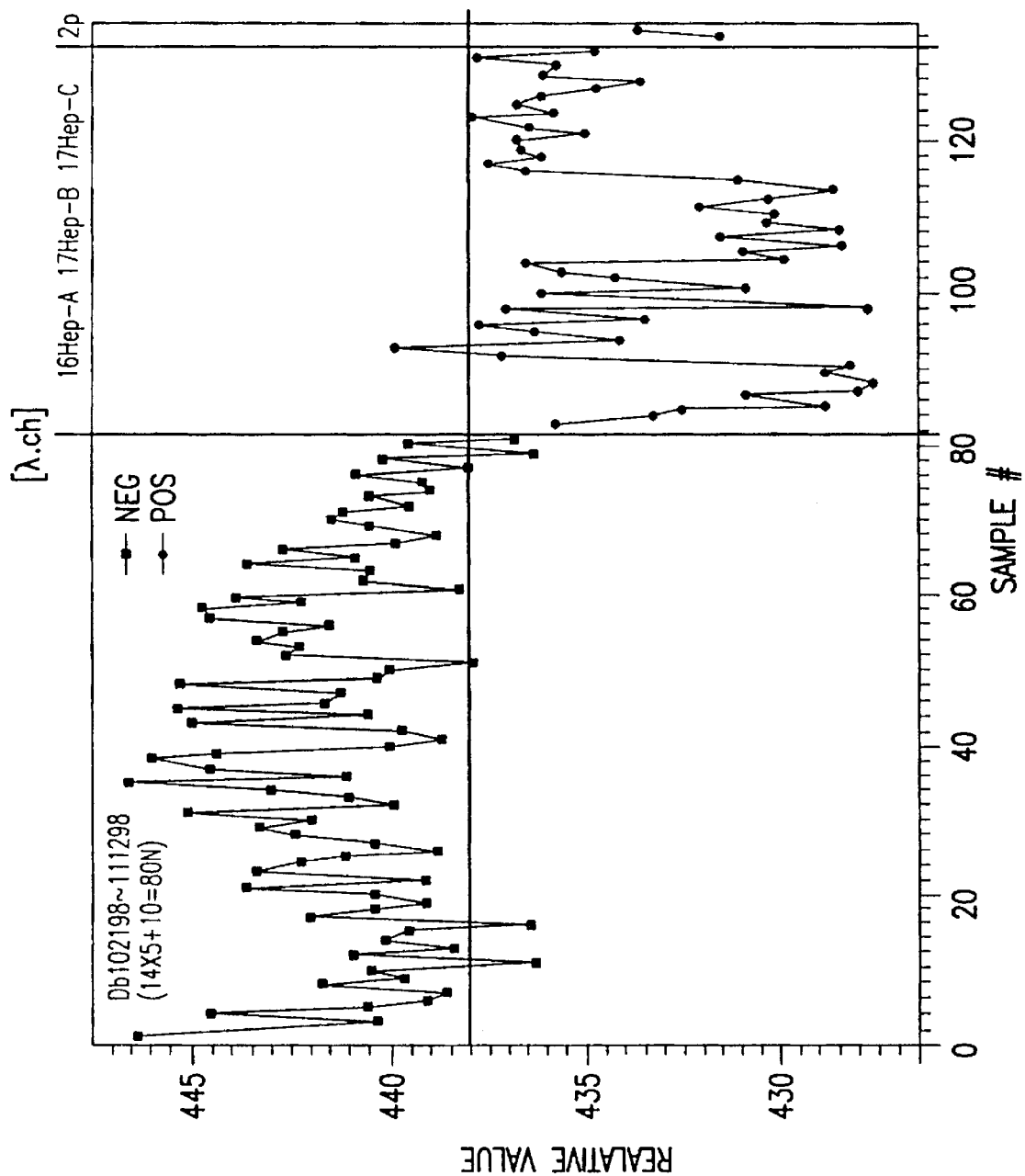
FIG. 31 shows the peak emission wavelengths of the same Hepatitis infected samples of FIG. 29 as compared with those of non-Hepatitis infected control samples.

FIG. 31 shows the peak wavelength, $\lambda_{CH}$, measurement of charcoal-treated samples, which indicates that this parameter discriminates Hepatitis A, B and C, respectively, from the normal samples.

Figure 32:
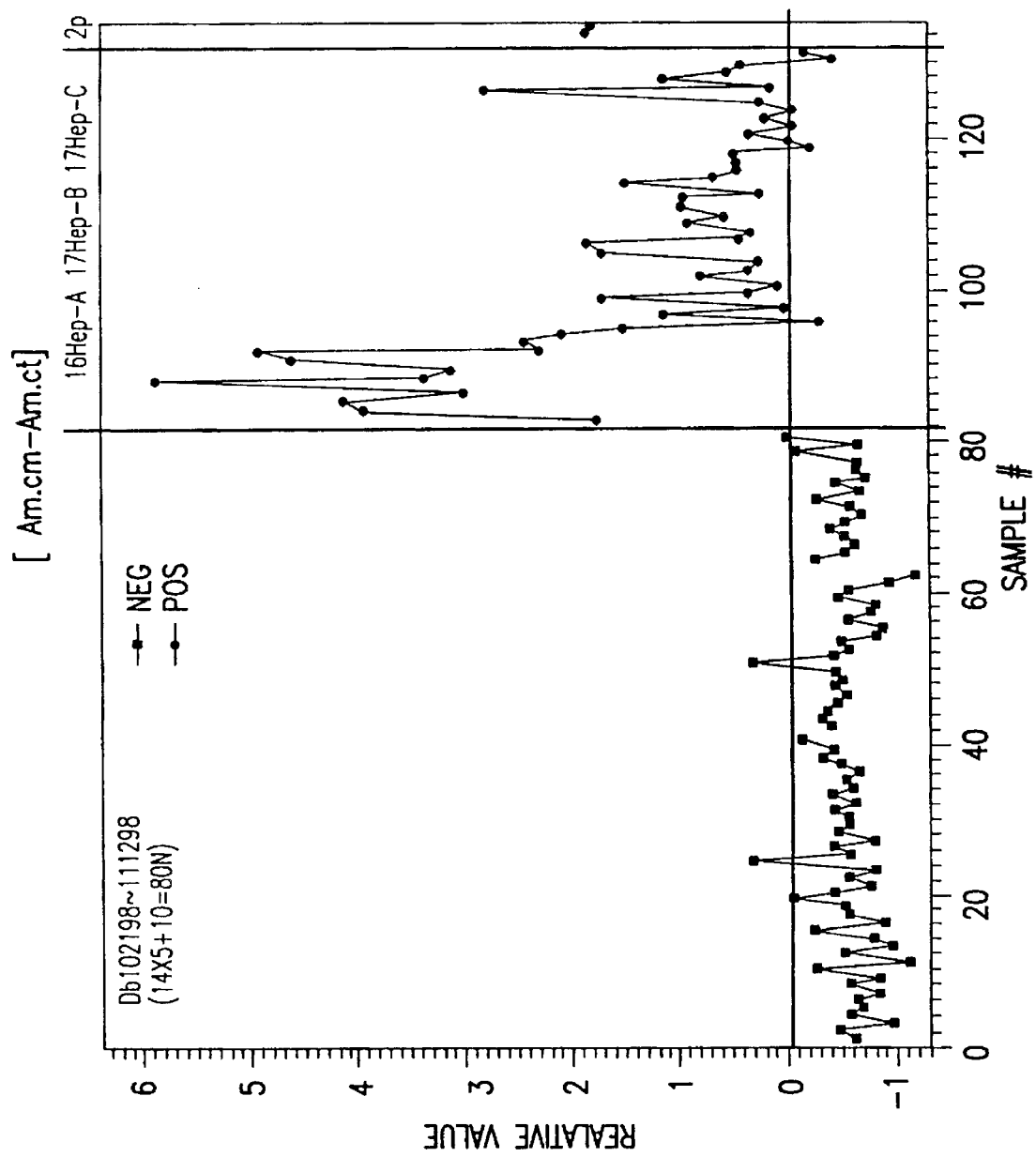
FIG. 32 shows peak emission amplitude differences of the same samples of FIG. 29 between the samples treated with CM-AGB and the same samples treated with activated charcoal and their comparison to those of non-Hepatitis infected control samples.

FIG. 32 shows the parameter $(Am_{CM}-Am_{CT})$, i.e., peak amplitude differences between CM-AGB treated samples and non-treated samples (control samples), which indicate that this parameter discriminates Hepatitis A, B and C, respectively, from the normal samples. Moreover, this parameter can also be used to differentiate Hepatitis A from Hepatitis C.

Figure 33:
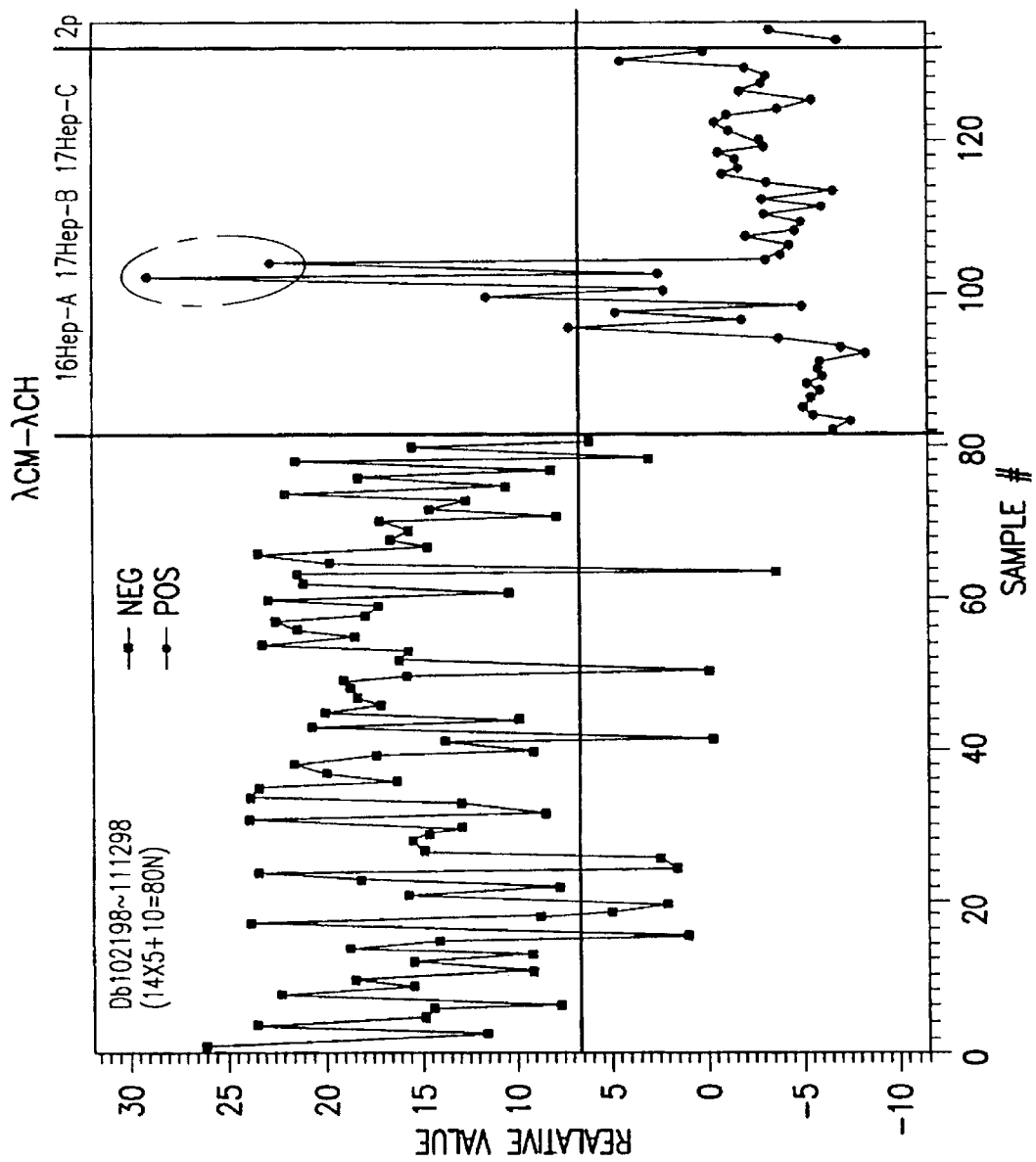
FIG. 33 shows peak emission wavelength differences of the same samples of FIG. 29 between the samples treated with CM-AGB and the same samples treated with activated charcoal and their comparisons to that of non-Hepatitis infected control samples.

FIG. 33 shows the parameter $(\lambda_{CM}-\lambda_{CH})$, i.e., peak wavelength differences between CM-AGB treated samples and charcoal-treated samples, which shows that this parameter distinguishes Hepatitis A and C from normal samples.

Figure 34:
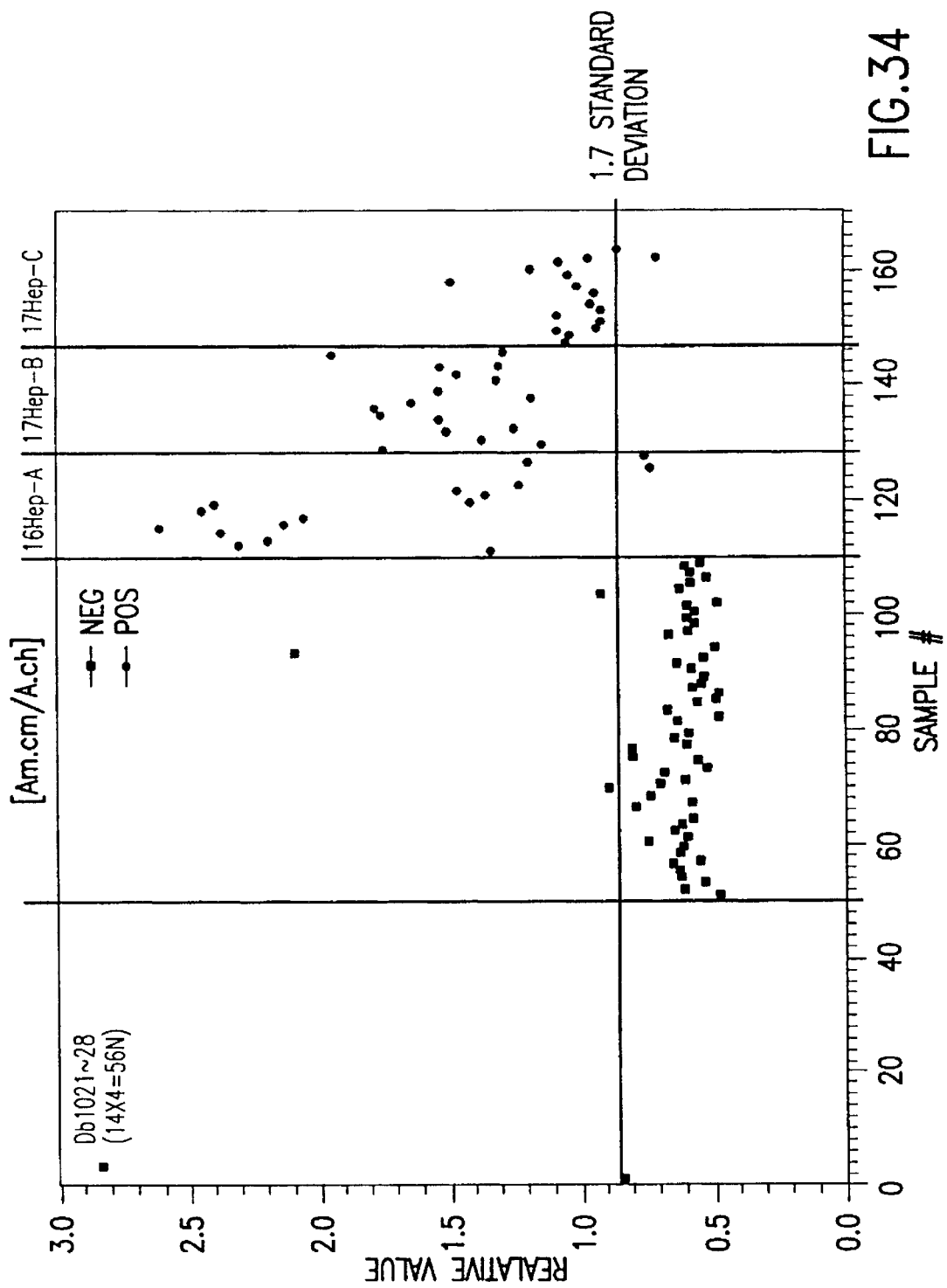
FIG. 34 shows a comparison of the parameters of peak emission amplitude of samples treated with CM-AGB divided by peak emission wavelength of the same sample but treated with activated charcoal between certain Hepatitis infected samples and non-Hepatitis infected control samples.

FIG. 34 shows the parameter $(Am_{CM}/\lambda_{CH})$, i.e., the amplitude of the CM-AGB treated samples divided by the peak wavelength of the charcoal-treated samples, which demonstrate that this parameter is a partial discriminator for Hepatitis A and C from normal samples, and is a good discriminator for Hepatitis B and normal samples.

Figure 35:
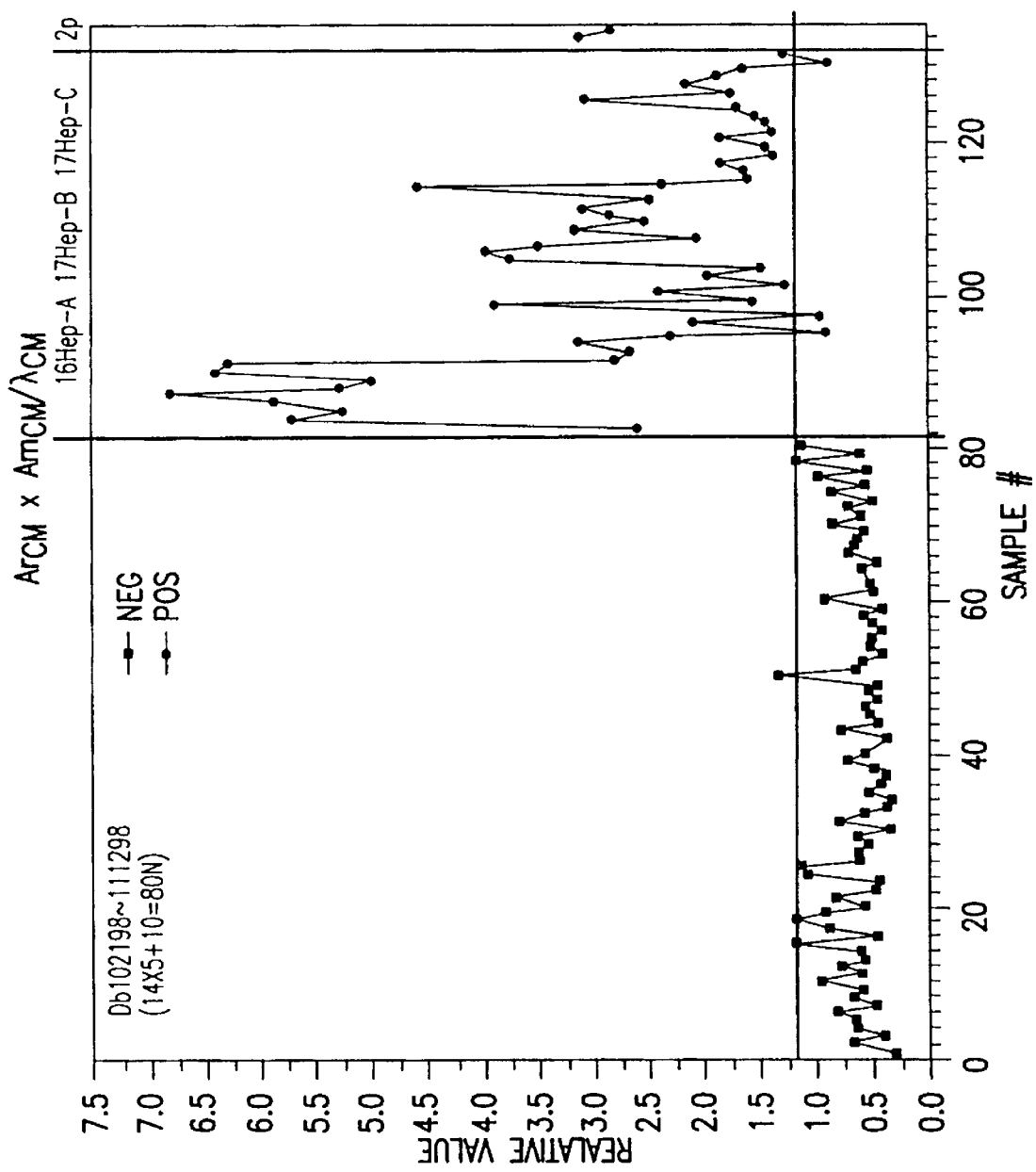
FIG. 35 shows a comparison of the parameters of certain samples for Hepatitis detection.

FIG. 35 shows a composite parameter $(Ar_{CM}*Am_{CM}/\lambda_{CM})$, i.e., the area ratio of the CM-AGB treated samples times the amplitude of such CM-AGB treated samples divided by the peak wavelength of such CM-AGB treated samples, which differentiates Hepatitis A, B, and C from the normal samples.

In all of the above samples, the laser excitation wavelength and the observed spectrum range are the same as that described above for the HIV detection. This demonstrates that the infectious disease detection method and apparatus of the present invention is capable of being adapted for detection of a variety of viruses present in plasma samples, such as HIV viruses, and Hepatitis A, B and C.

It will be apparent to one of ordinary skill in the art that the various other parameters may be adapted in accordance with the present invention, which may be used to discriminate infectious diseases, such as Hepatitis A, B and C. The following examples provides additional parameters for detection of Hepatitis A, B and C.

Figure 36:
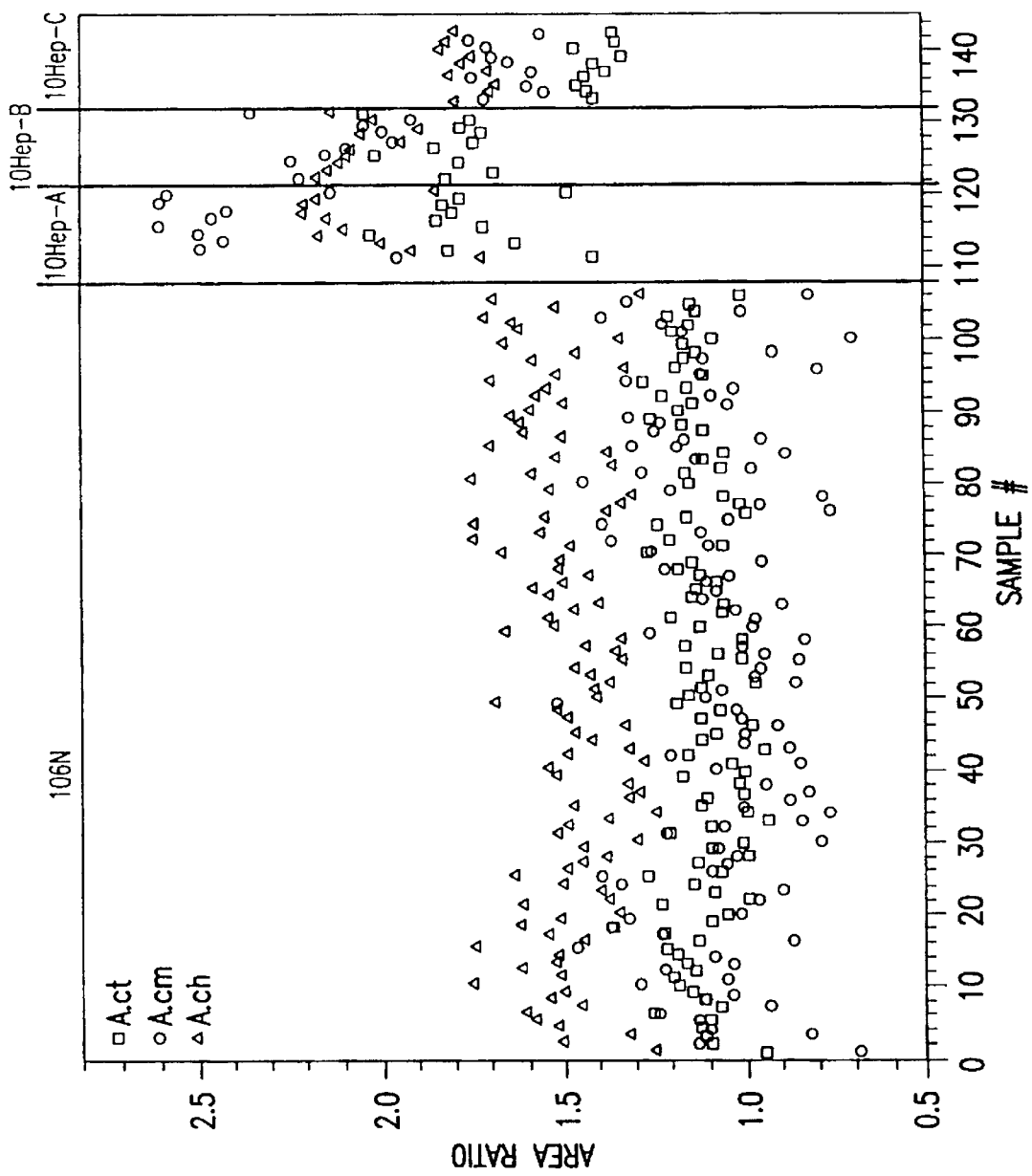
FIG. 36 shows area ratios of certain samples for Hepatitis detection.

FIG. 36 shows the parameter of area ratios, Ar, for control samples, $Ar_{CT}$, (i.e., non-treated samples), represented as small squares in the FIG.; CM-AGB treated samples, $Ar_{CM}$, represented as small circles in the FIG., and charcoal-treated samples, $Ar_{CH}$, represented as small triangles in the FIG. It is shown that the parameter $Ar_{CT}$ is a good discriminator for Hepatitis A, B and C, and the normal samples.

Figure 37:
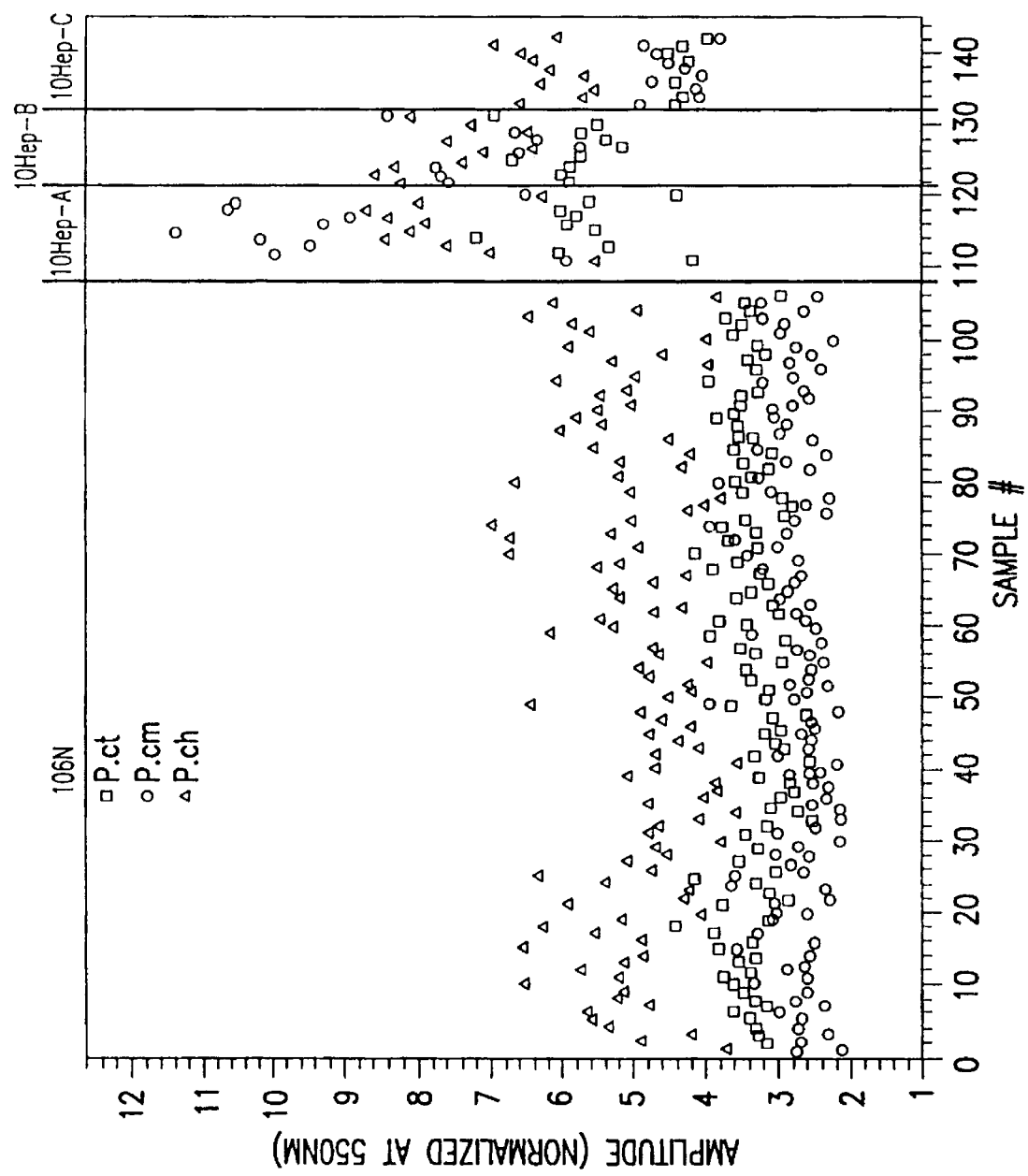
FIG. 37 shows normalized peak amplitude measurement results for Hepatitis detection.

FIG. 37 shows the normalized peak amplitude, Am, for control samples, $Am_{CT}$, (i.e., non-treated samples), represented as small squares in the FIG.; CM-AGB treated samples, $Am_{CM}$, represented as small circles in the FIG., and charcoal-treated samples, $Am_{CH}$, represented as small triangles in the FIG.

Figure 38:
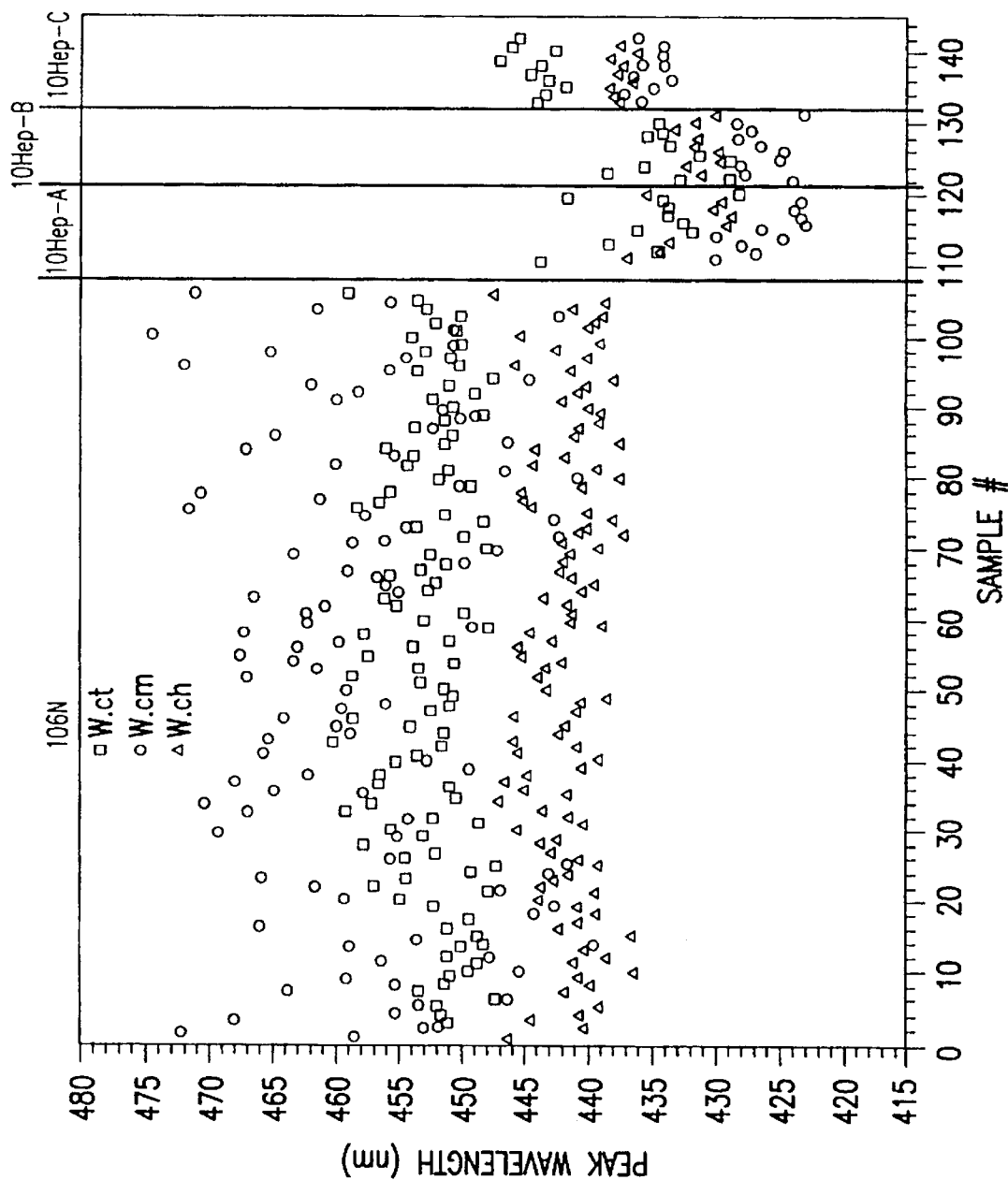
FIG. 38 shows peak wavelength measurement results for Hepatitis detection.

FIG. 38 shows the peak wavelength, $\lambda_p$, for control samples, $\lambda_{CT}$, (i.e., non-treated samples), represented as small squares in the FIG.; CM-AGB treated samples, $\lambda_{CM}$, represented as small circles in the FIG., and charcoal-treated samples, $\lambda_{CH}$, represented as small triangles in the FIG.

Figure 39:
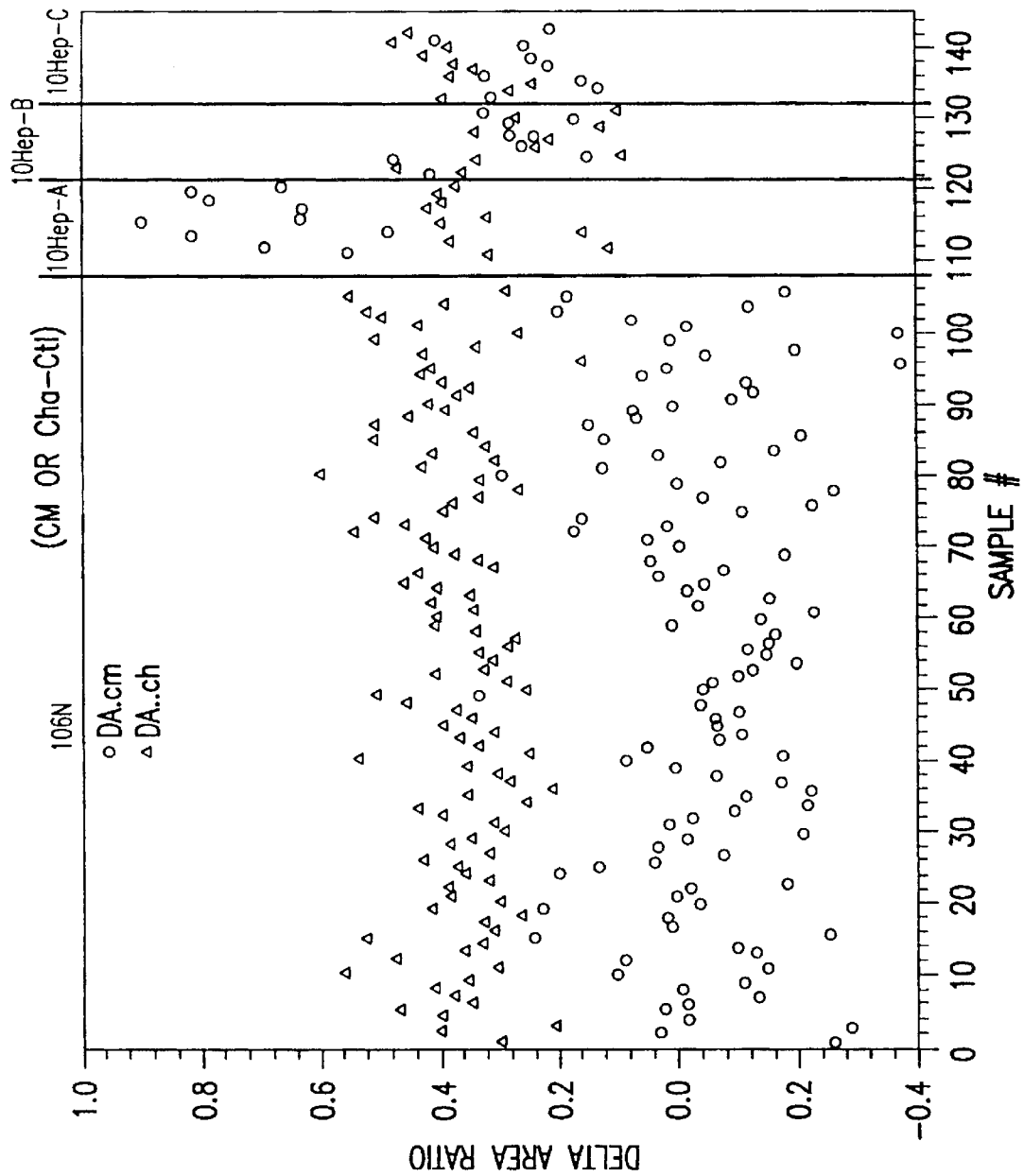
FIG. 39 shows area ratio changes of certain treated samples for Hepatitis detection.

FIG. 39 shows the area ratio changes between CM-AGB treated samples and control samples, $(Ar_{CM}-Ar_{CT})$, represented as small circles in the FIG.; and area ratio changes between charcoal treated samples and control samples, $(Ar_{CH}-Ar_{CT})$, represented as small triangles in the FIG.

Figure 40:
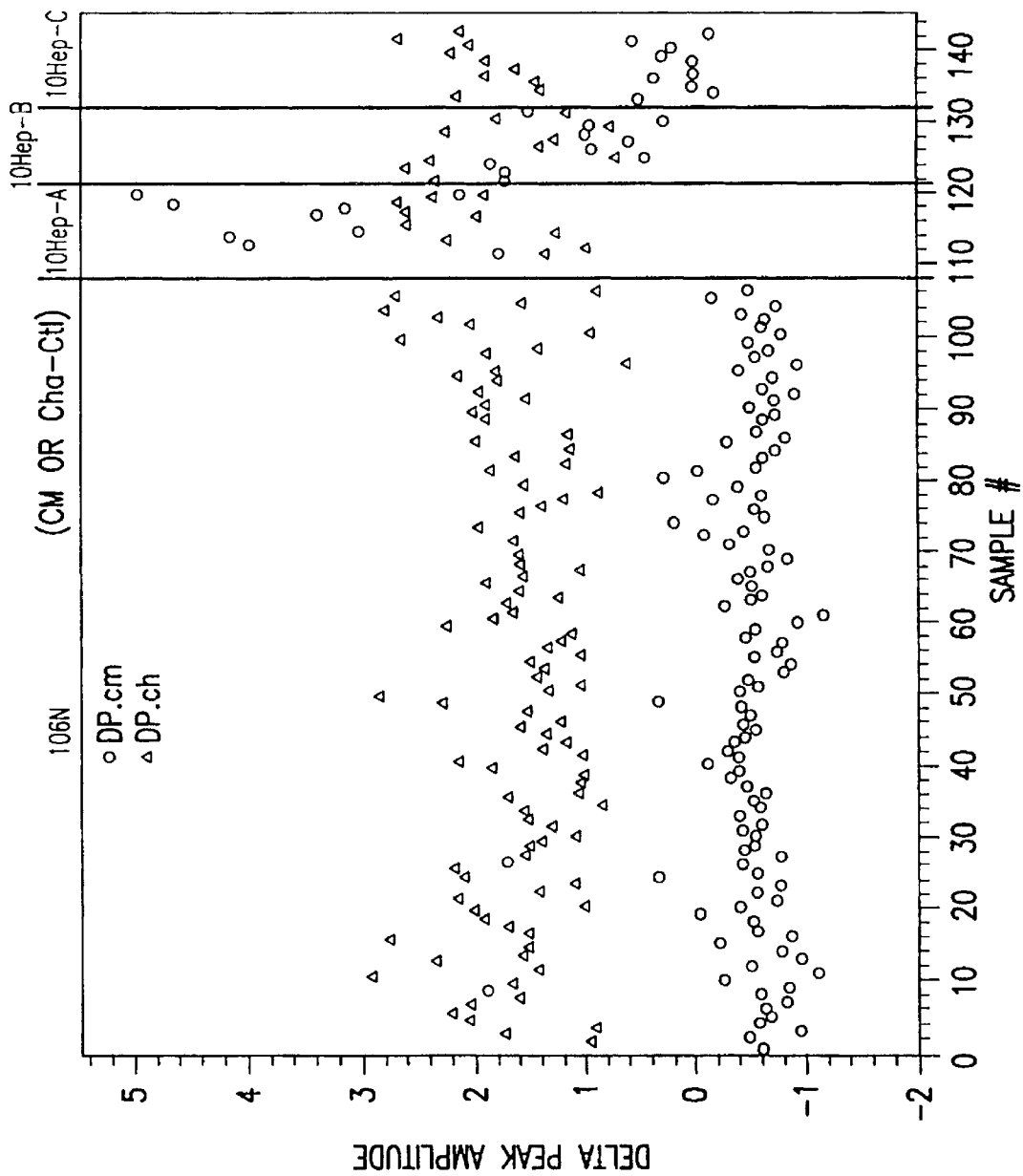
FIG. 40 shows amplitude changes of certain treated samples for Hepatitis detection.

FIG. 40 shows the peak amplitude changes between CM-AGB treated samples and control samples, $(Am_{CM}-Am_{CT})$, represented as small circles in the FIG.; and peak amplitude changes between charcoal treated samples and control samples, $(Am_{CH}-Am_{CT})$, represented as small triangles in the FIG.

Figure 41:
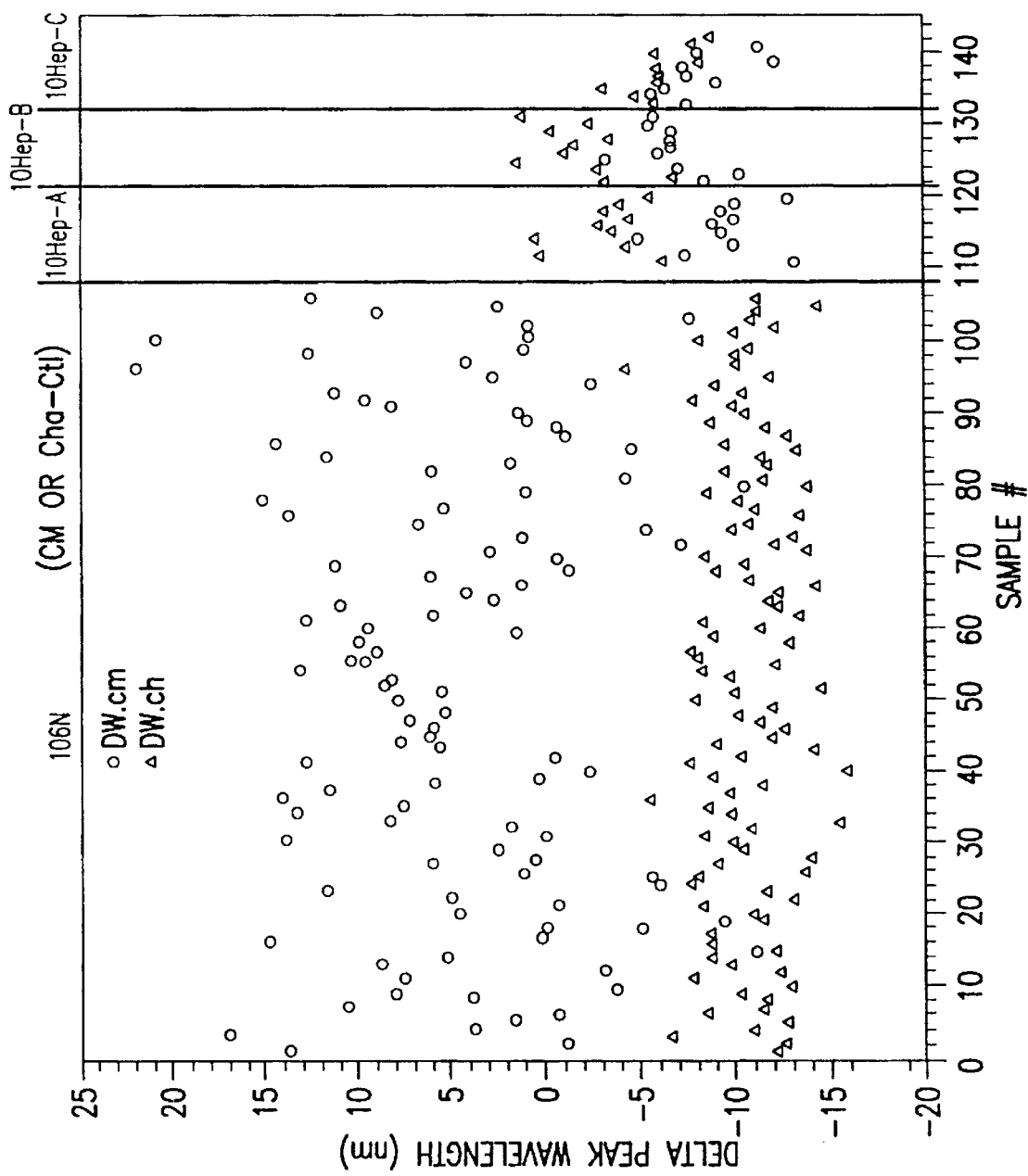
FIG. 41 shows peak wavelength changes of certain treated samples for Hepatitis detection.

FIG. 41 shows the peak wavelength changes between CM-AGB treated samples and control samples, $(\lambda p_{CM}-\lambda p_{CT})$, represented as small circles in the FIG.; and peak wavelength changes between charcoal treated samples and control samples, $(\lambda p_{CH}-\lambda p_{CT})$, represented as small triangles in the FIG.

Figure 42:
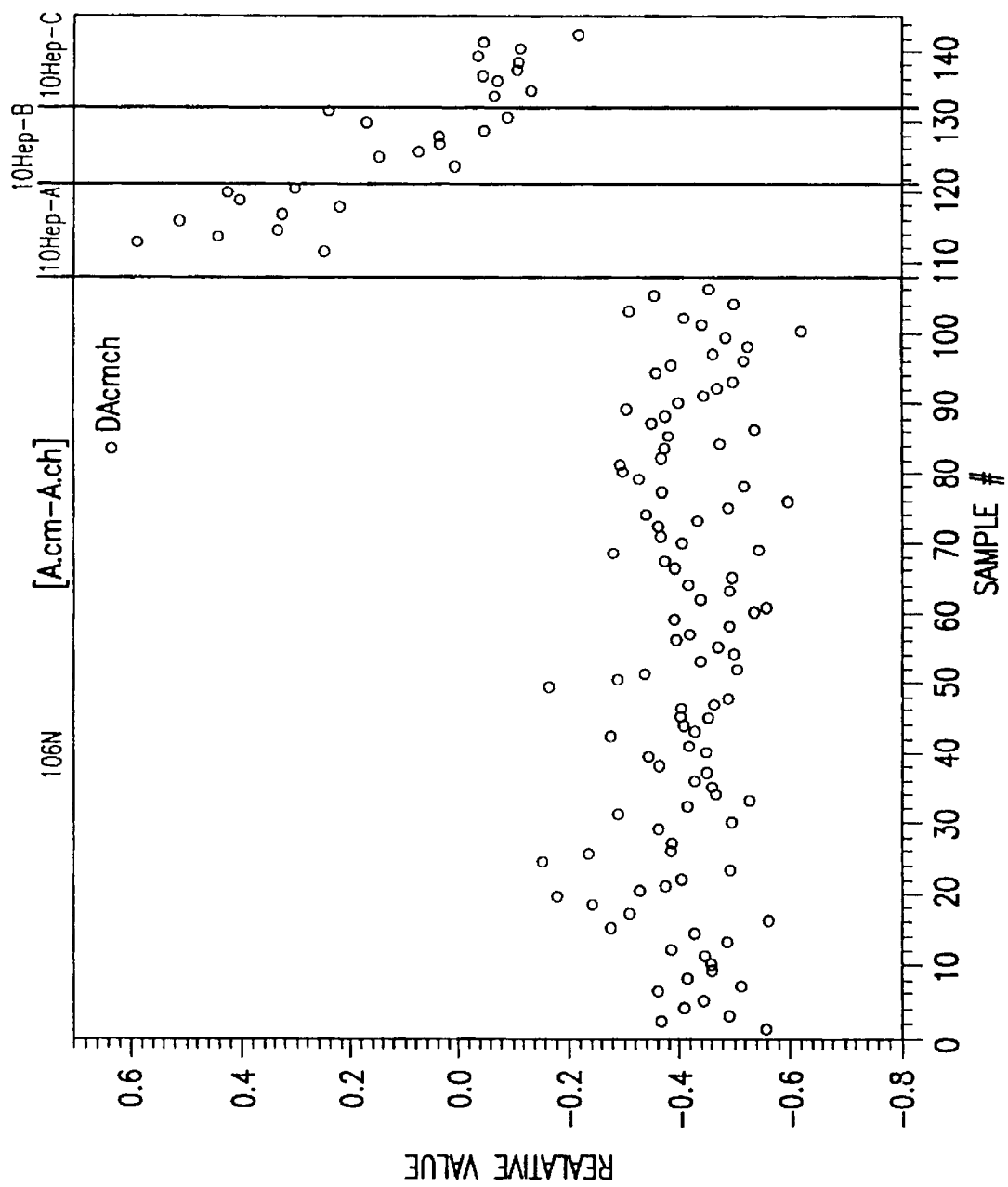
FIG. 42 shows area ratio changes of certain treated samples for Hepatitis detection.

FIG. 42 shows the area ratio changes between CM-AGB treated samples and charcoal-treated samples, $(Ar_{CM}-Ar_{CH})$, represented as small circles in the FIG. It clearly shows that this parameter is a good discriminator for normal samples and the samples containing Hepatitis A, B or C.

Figure 43:
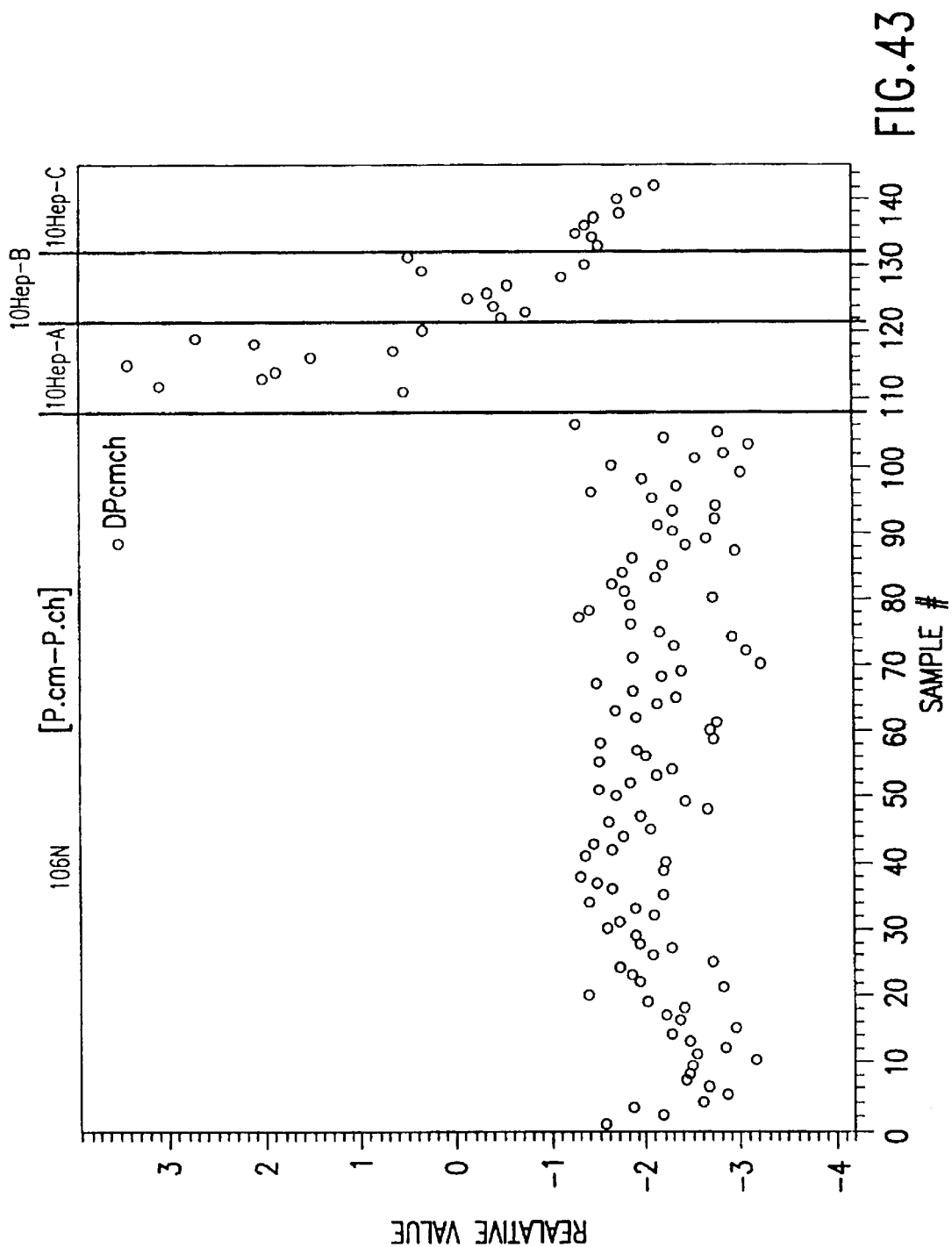
FIG. 43 shows amplitude changes of certain treated samples for Hepatitis detection.

FIG. 43 shows the amplitude changes between CM-AGB treated samples and charcoal-treated samples, ($Am_{CM}$–$Am_{CH}$), represented as small circles in the FIG.

Figure 44:
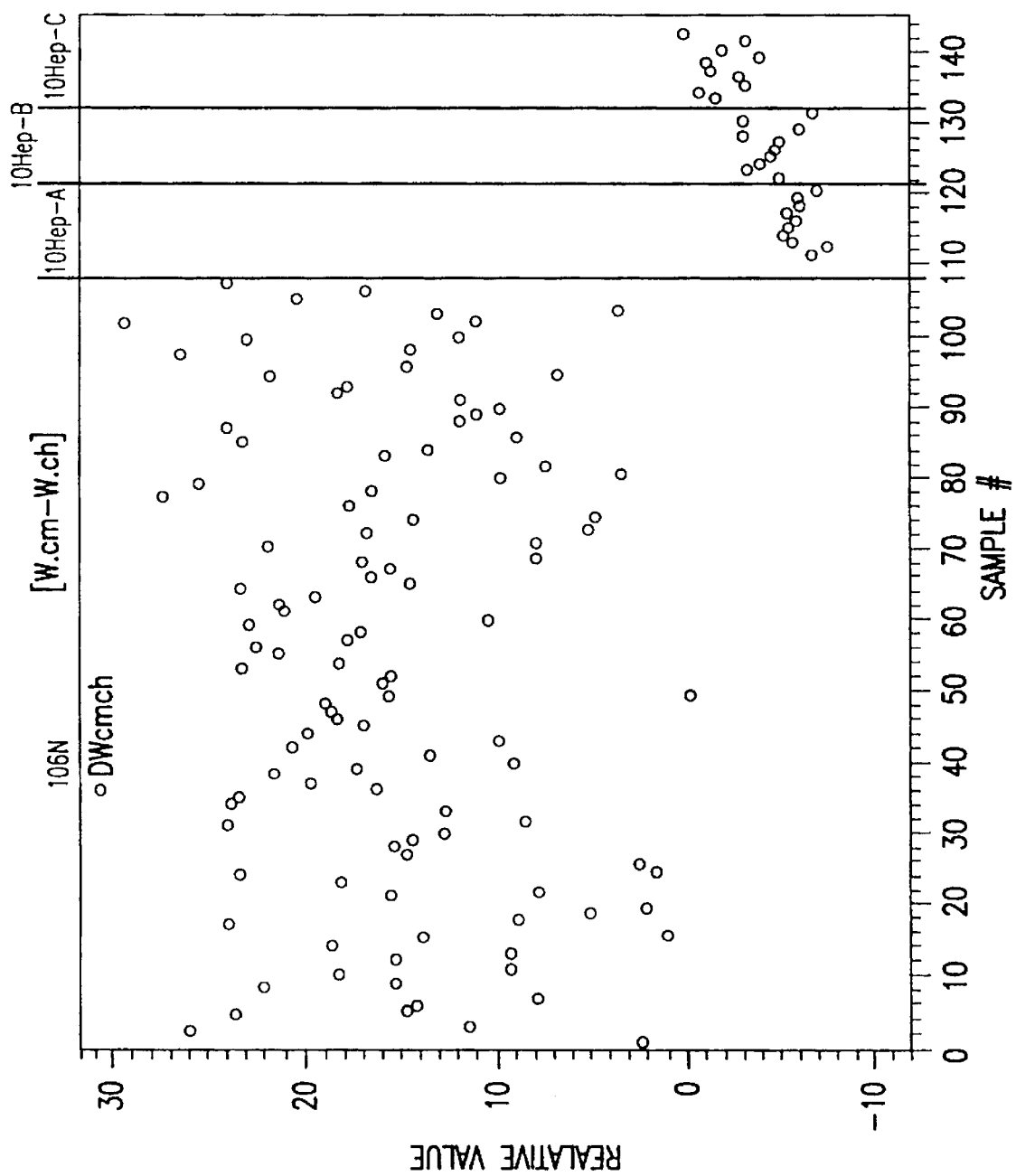
FIG. 44 shows peak wavelength changes of certain treated samples for Hepatitis detection.

FIG. 44 shows the peak wavelength changes between CM-AGB treated samples and charcoal-treated samples, ($\lambda p_{CM}$–$\lambda p_{CH}$), represented as small circles in the FIG. This parameter clearly discriminates the normal samples from those containing Hepatitis A, B or C.

Figure 45:
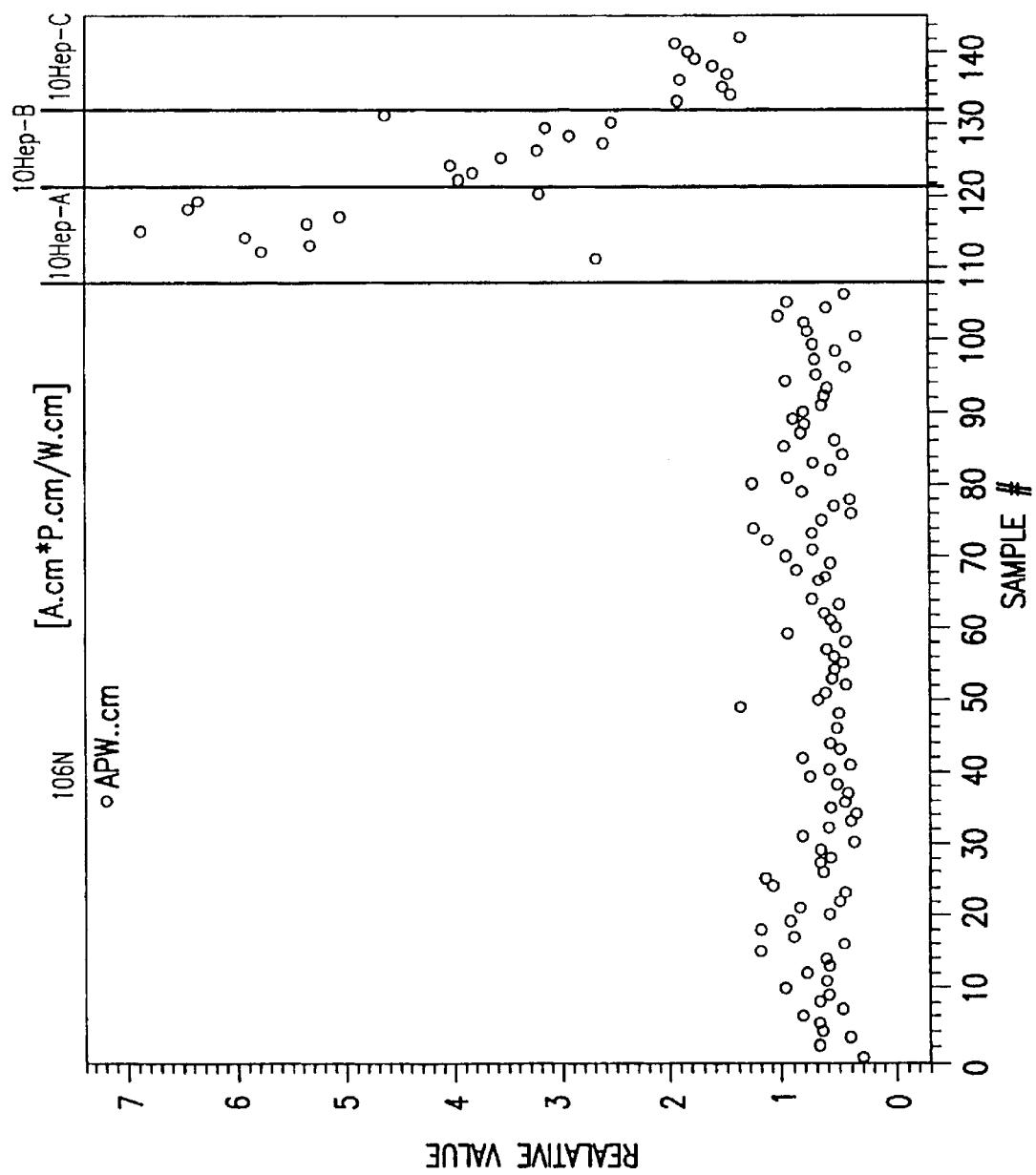
FIG. 45 shows composite parameters of certain samples for Hepatitis detection.

FIG. 45 shows a composite parameter, area ratio times the amplitude divided by the peak wavelength, $Ar_{CM}*Am_{CM}/\lambda p_{CM}$, for samples treated with CM-AGB, represented as small circles in the FIG. This parameter at least differentiates the normal samples from Hepatitis A or B positive samples.

Figure 46:
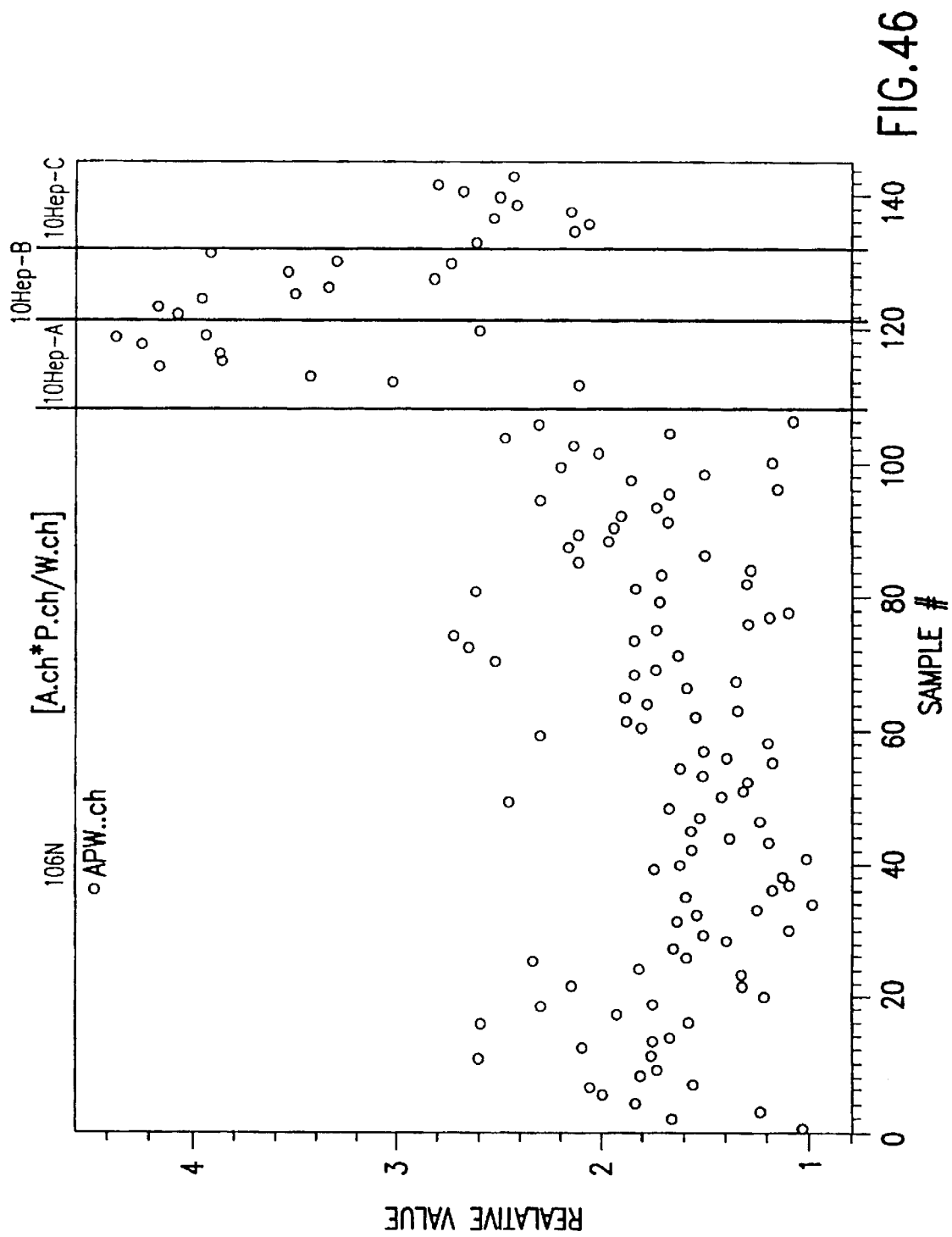
FIG. 46 shows different composite parameters of certain samples for Hepatitis detection.

FIG. 46 shows another composite parameter, area ratio times the amplitude divided by the peak wavelength, $Ar_{CH}*Am_{CH}/\lambda p_{CH}$, for samples treated with charcoal, represented as small circles in the FIG.

The preferred embodiment described above is not intended to limit the applicability of the present invention. Rather, a person skilled in the art would appreciate that various modifications of the arrangements and types of components used in the detection system not mentioned in the specifications of the present invention would fall within the scope and spirit of the claimed invention. For instance, other types of spectrometers may be used in place of a CCD spectrometer.

We claim:

1. A method for detecting presence of at least one of hepatitis C and HIV in a sample that comprises native fluorescent substances, comprising:
   a. obtaining plasma containing albumin;
   b. preparing a sample from the plasma without the addition of fluorophores that are not native fluorescent substances to the plasma, and wherein preparing the sample comprises reducing the amount of albumin in the sample;
   c. directing laser light of a predetermined wavelength onto the sample;
   d. obtaining an emission spectrum from the sample, the emission spectrum having an intensity maximum at a wavelength of at least about 400 nanometers and the emission spectrum resulting from the fluorescent substances that are native to the plasma and not from any fluorescent substances that are not native to the plasma; and
   e. comparing an area ratio within the emission spectrum and a wavelength of peak intensity of the emission spectrum of the native fluorescent substances with an area ratio within a control spectrum and a wavelength of peak intensity, respectively, of a control spectrum to determine the presence of the at least one of hepatitis C and HIV in the sample.

2. The method of claim 1, wherein the laser light has a wavelength between about 310 and about 400 nanometers.

3. The method of claim 1, further comprising comparing an intensity of the emission spectrum of the native fluorescent substances with an intensity of a control spectrum to determine the presence of the at least one of hepatitis C and HIV in the sample.

4. A method for determining presence of at least one of hepatitis C and HIV in a sample that includes native fluorescent substances, comprising:
   a. obtaining the plasma;
   b. preparing a sample from the plasma without the addition of fluorophores that are not native fluorescent substances to the plasma;
   c. directing laser light of a wavelength between about 310 and about 400 nanometers onto the sample;
   d. obtaining an emission spectrum from the sample, the emission spectrum having a maximum of at least about 400 nanometers, and the emission spectrum resulting from the native fluorescent substances of the sample and not from any fluorescent substances that are not native to the plasma; and
   e. comparing at least one spectral parameter of the emission spectrum of the native fluorescent substances with a corresponding spectral parameter of a control spectrum to determine the presence of the at least one of hepatitis C and HIV in the sample, wherein the spectral parameter includes at least one of an area ratio within a control spectrum and a wavelength of peak intensity.

5. The method of claim 4, wherein at least two of the spectral parameters of the native fluorescent substances are compared with the corresponding spectral parameters of the control spectrum.

6. The method of claim 4, wherein the spectral parameter further includes an intensity.

7. The method of claim 6, wherein at least three of the spectral parameters of the native fluorescent substances are compared with the corresponding spectral parameters of the control spectrum.

8. The method of claim 4, wherein the plasma further comprises albumin, and further wherein preparing the sample comprises reducing the amount of albumin in the sample.

9. A method for detecting the presence of at least one of hepatitis C and HIV in a sample that comprises native fluorescent substances, comprising:
   a. obtaining plasma;
   b. preparing a sample from the plasma;
   c. irradiating the sample with light of a predetermined wavelength;
   d. obtaining an emission spectrum from the sample, the emission spectrum having a maximum of at least about 400 nanometers, and the emission spectrum being free of emission from added fluorophores that are not native fluorescent substances to the sample; and
   e. comparing at least one spectral parameter of the emission spectrum of the native fluorescent substances with a corresponding spectral parameter of a control spectrum to determine the presence of the at least one of hepatitis C and HIV in the sample, wherein the spectral parameter includes at least one of an area ratio within a control spectrum and a wavelength of peak intensity.

10. The method of claim 9, wherein at least two of the spectral parameters of the native fluorescent substances are compared with the corresponding spectral parameters of the control spectrum.

11. The method of claim 9, wherein the spectral parameter further includes an intensity.

12. The method of claim 11, wherein at least three of the spectral parameters of the native fluorescent substances are compared with the corresponding spectral parameters of the control spectrum.

13. The method of claim 9, wherein the plasma further comprises albumin, and further wherein preparing the sample comprises reducing the amount of albumin in the sample.

14. A method for detecting presence of at least one of hepatitis C and HIV in plasma, comprising:
   a. obtaining plasma;
   b. obtaining a first emission spectrum from the plasma;

c. subjecting a portion of the plasma to at least one of contacting the plasma with an adsorbent and contacting the plasma with a denaturant, to obtain a treated plasma;

f. obtaining a second emission spectrum from the treated plasma; and e. determining the presence of the at least one of hepatitis C and HIV in the plasma based on a change in at least one spectral parameter of the first and second emission spectra, wherein the at least one spectral parameter includes at least one of an area ratio within a control spectrum and a wavelength of peak intensity.

15. The method of claim 14, wherein determining the presence of the at least one of hepatitis C and HIV comprises determining a difference between the change in the at least one spectral parameter and a change in a corresponding spectral parameter of a control spectrum.

16. The method of claim 14, wherein determining the presence of the at least one of hepatitis C and HIV comprises determining a change in the wavelength of peak intensity of the first and second emission spectra.

17. The method of claim 16, wherein determining the presence of the at least one of hepatitis C and HIV comprises determining a change in an area ratio within a control spectrum and a wavelength of peak intensity of the first and second emission spectra.

18. The method of claim 17, wherein determining the presence of the at least one of hepatitis C and HIV comprises determining a change in an area ratio within a control spectrum, a wavelength of peak intensity, and an intensity of the first and second spectra.

19. The method of claim 14, wherein the first emission spectrum and the second emission spectrum result from fluorescent substances that are native to the plasma and not from fluorescent substances that are not native to the plasma.

20. The method of claim 14, wherein the first and second emission spectra have a peak wavelength of greater than about 400 nanometers.

21. The method of claim 14, wherein the obtaining an first emission spectrum and obtaining a second emission spectrum steps comprise directing laser light of a wavelength between about 310 and about 400 nanometers onto the plasma and treated plasma, respectively.

* * * * *